(12) United States Patent
Jha et al.

(10) Patent No.: US 12,395,429 B2
(45) Date of Patent: *Aug. 19, 2025

(54) MEDICAL DEVICE COMMUNICATION METHOD

(71) Applicant: ICU Medical, Inc., San Clemente, CA (US)

(72) Inventors: Prakash Kumar Arvind Jha, San Diego, CA (US); James Cudney, Santee, CA (US); Benjamin Herr, Kelso, WA (US); Mark I. Lee, Poway, CA (US); Matteo D. Picinich, Temecula, CA (US)

(73) Assignee: ICU Medical, Inc., San Clemente, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/743,658

(22) Filed: Jun. 14, 2024

(65) Prior Publication Data
US 2025/0016093 A1   Jan. 9, 2025

Related U.S. Application Data

(63) Continuation of application No. 18/045,061, filed on Oct. 7, 2022, now Pat. No. 12,047,292, which is a
(Continued)

(51) Int. Cl.
H04L 45/74 (2022.01)
G16H 20/17 (2018.01)
(Continued)

(52) U.S. Cl.
CPC ............ H04L 45/74 (2013.01); G16H 20/17 (2018.01); G16H 40/63 (2018.01); G16H 40/67 (2018.01);
(Continued)

(58) Field of Classification Search
CPC ..... H04L 69/32; H04L 69/165; H04L 69/162; H04L 69/16; H04L 45/74; H04L 45/302; G16H 40/67; G16H 40/63; G16H 20/17
(Continued)

(56) References Cited

U.S. PATENT DOCUMENTS 4,024,864 A    5/1977   Davies et al.
4,055,175 A   10/1977   Clemens et al.
(Continued)

FOREIGN PATENT DOCUMENTS

AU   2004226440   10/2004
AU   2004305087    7/2005
(Continued)

OTHER PUBLICATIONS

Sethia et al., "Security Framework for Portable NFC Mobile Based Health Record System", Oct. 2016, IEEE 12th International Conference on Wireless and Mobile Computing, Networking and Communications, pp. 1-8.
(Continued)

Primary Examiner — Gbemileke J Onamuti
(74) Attorney, Agent, or Firm — Knobbe, Martens, Olson & Bear, LLP

(57) ABSTRACT

A medical device communication method that may be implemented within a variety of medical devices including but not limited to infusion pumps. The method may be implemented with a protocol stack for at least intra-device communication. Embodiments provide connection-oriented, connectionless-oriented, broadcast and multicast data exchange with priority handling of data, fragmentation, and reassembly of data, unique static and dynamic address assignment and hot swap capability for connected peripherals or subsystems.

17 Claims, 19 Drawing Sheets

Related U.S. Application Data continuation of application No. 17/074,268, filed on Oct. 19, 2020, now Pat. No. 11,470,000, which is a continuation of application No. 16/446,381, filed on Jun. 19, 2019, now Pat. No. 10,812,380, which is a continuation of application No. 15/581,442, filed on Apr. 28, 2017, now Pat. No. 10,333,843, which is a continuation of application No. 14/198,807, filed on Mar. 6, 2014, now Pat. No. 9,641,432.

(60) Provisional application No. 61/773,647, filed on Mar. 6, 2013.

(51) Int. Cl.
   *G16H 40/63*       (2018.01)
   *G16H 40/67*       (2018.01)
   *H04L 45/302*      (2022.01)
   *H04L 69/16*       (2022.01)
   *H04L 69/165*      (2022.01)
   *H04L 69/32*       (2022.01)

(52) U.S. Cl.
   CPC ............ *H04L 45/302* (2013.01); *H04L 69/16* (2013.01); *H04L 69/162* (2013.01); *H04L 69/165* (2013.01); *H04L 69/32* (2013.01)

(58) Field of Classification Search
   USPC .......................................................... 370/392
   See application file for complete search history.

(56) References Cited

U.S. PATENT DOCUMENTS

| | | |
|---|---|---|
| 4,151,845 A | 5/1979 | Clemens |
| 4,213,454 A | 7/1980 | Shim |
| 4,240,438 A | 12/1980 | Updike et al. |
| 4,280,494 A | 7/1981 | Cosgrove et al. |
| 4,308,866 A | 1/1982 | Jeliffe |
| 4,370,983 A | 2/1983 | Lichtenstein et al. |
| 4,373,527 A | 2/1983 | Fischell |
| 4,392,849 A | 7/1983 | Petre et al. |
| 4,395,259 A | 7/1983 | Prestele et al. |
| 4,457,751 A | 7/1984 | Rodler |
| 4,464,170 A | 8/1984 | Clemens |
| 4,469,481 A | 9/1984 | Kobayashi |
| 4,475,901 A | 10/1984 | Kraegen et al. |
| 4,494,950 A | 1/1985 | Fischell |
| 4,498,843 A | 2/1985 | Schneider et al. |
| 4,515,584 A | 5/1985 | Abe et al. |
| 4,526,568 A | 7/1985 | Clemens et al. |
| 4,529,401 A | 7/1985 | Leslie et al. |
| 4,543,955 A | 10/1985 | Schroeppel |
| 4,551,133 A | 11/1985 | Zegers de Beyl et al. |
| 4,553,958 A | 11/1985 | LeCocq |
| 4,559,037 A | 12/1985 | Franetzki et al. |
| 4,613,937 A | 9/1986 | Batty |
| 4,624,661 A | 11/1986 | Arimond |
| 4,633,878 A | 1/1987 | Bombardieri |
| 4,634,426 A | 1/1987 | Kamen |
| 4,634,427 A | 1/1987 | Hannula et al. |
| 4,674,652 A | 6/1987 | Aten et al. |
| 4,676,776 A | 6/1987 | Howson et al. |
| 4,679,562 A | 7/1987 | Luksha |
| 4,685,903 A | 8/1987 | Cable et al. |
| 4,695,954 A | 9/1987 | Rose |
| 4,696,671 A | 9/1987 | Epstein et al. |
| 4,714,462 A | 12/1987 | DiDomenico |
| 4,722,734 A | 2/1988 | Kolin |
| 4,730,849 A | 3/1988 | Siegel |
| 4,731,051 A | 3/1988 | Fischell |
| 4,741,732 A | 5/1988 | Crankshaw et al. |
| 4,756,706 A | 7/1988 | Kerns et al. |
| 4,776,842 A | 10/1988 | Franetzki et al. |
| 4,785,969 A | 11/1988 | McLaughlin |
| 4,803,625 A | 2/1989 | Fu et al. |
| 4,835,372 A | 5/1989 | Gombrich et al. |
| 4,838,275 A | 6/1989 | Lee |
| 4,838,856 A | 6/1989 | Mulreany et al. |
| 4,838,857 A | 6/1989 | Strowe et al. |
| 4,854,324 A | 8/1989 | Hirschman et al. |
| 4,857,716 A | 8/1989 | Gombrich et al. |
| 4,858,154 A | 8/1989 | Anderson et al. |
| 4,898,578 A | 2/1990 | Rubalcaba, Jr. |
| 4,908,017 A | 3/1990 | Howson et al. |
| 4,933,873 A | 6/1990 | Kaufman et al. |
| 4,943,279 A | 7/1990 | Samiotes et al. |
| 4,946,439 A | 8/1990 | Eggers |
| 4,953,745 A | 9/1990 | Rowlett |
| 4,978,335 A | 12/1990 | Arthur, III |
| 5,000,739 A | 3/1991 | Kulisz et al. |
| 5,010,473 A | 4/1991 | Jacobs |
| 5,014,698 A | 5/1991 | Cohen |
| 5,016,172 A | 5/1991 | Dessertine |
| 5,026,084 A | 6/1991 | Paisfield |
| 5,034,004 A | 7/1991 | Crankshaw |
| 5,041,086 A | 8/1991 | Koenig et al. |
| 5,058,161 A | 10/1991 | Weiss |
| 5,078,683 A | 1/1992 | Sancoff et al. |
| 5,084,828 A | 1/1992 | Kaufman et al. |
| 5,088,981 A | 2/1992 | Howson et al. |
| 5,097,505 A | 3/1992 | Weiss |
| 5,100,380 A | 3/1992 | Epstein et al. |
| 5,102,392 A | 4/1992 | Sakai et al. |
| 5,104,374 A | 4/1992 | Bishko et al. |
| 5,109,850 A | 5/1992 | Blanco et al. |
| 5,131,816 A | 7/1992 | Brown |
| 5,142,484 A | 8/1992 | Kaufman et al. |
| 5,153,827 A | 10/1992 | Coutre et al. |
| 5,157,640 A | 10/1992 | Backner |
| 5,161,222 A | 11/1992 | Montejo et al. |
| 5,177,993 A | 1/1993 | Beckman et al. |
| 5,181,910 A | 1/1993 | Scanlon |
| 5,190,522 A | 3/1993 | Wocicki et al. |
| 5,199,439 A | 4/1993 | Zimmerman et al. |
| 5,200,891 A | 4/1993 | Kehr et al. |
| 5,216,597 A | 6/1993 | Beckers |
| 5,221,268 A | 6/1993 | Barton et al. |
| 5,230,061 A | 7/1993 | Welch |
| 5,243,982 A | 9/1993 | Möstl et al. |
| 5,244,463 A | 9/1993 | Cordner, Jr. et al. |
| 5,249,260 A | 9/1993 | Nigawara et al. |
| 5,254,096 A | 10/1993 | Rondelet et al. |
| 5,256,156 A | 10/1993 | Kern et al. |
| 5,256,157 A | 10/1993 | Samiotes et al. |
| 5,261,702 A | 11/1993 | Mayfield |
| 5,317,506 A | 5/1994 | Coutre et al. |
| 5,319,355 A | 6/1994 | Russek |
| 5,319,363 A | 6/1994 | Welch et al. |
| 5,330,634 A | 7/1994 | Wong et al. |
| 5,338,157 A | 8/1994 | Blomquist |
| 5,341,476 A | 8/1994 | Lowell |
| 5,364,346 A | 11/1994 | Schrezenmeir |
| 5,366,346 A | 11/1994 | Danby |
| 5,368,562 A | 11/1994 | Blomquist et al. |
| 5,373,454 A | 12/1994 | Kanda et al. |
| 5,376,070 A | 12/1994 | Purvis et al. |
| 5,378,231 A | 1/1995 | Johnson et al. |
| 5,389,071 A | 2/1995 | Kawahara et al. |
| 5,389,078 A | 2/1995 | Zalesky et al. |
| 5,417,222 A | 5/1995 | Dempsey et al. |
| 5,423,748 A | 6/1995 | Uhala |
| 5,429,602 A | 7/1995 | Hauser |
| 5,431,627 A | 7/1995 | Pastrone et al. |
| 5,432,777 A | 7/1995 | Le Boudec et al. |
| 5,445,621 A | 8/1995 | Poli et al. |
| 5,447,164 A | 9/1995 | Shaya et al. |
| 5,455,851 A | 10/1995 | Chaco et al. |
| 5,461,365 A | 10/1995 | Schlager et al. |
| 5,464,392 A | 11/1995 | Epstein et al. |
| 5,465,082 A | 11/1995 | Chaco |
| 5,485,408 A | 1/1996 | Blomquist |
| 5,486,286 A | 1/1996 | Peterson et al. |
| 5,493,430 A | 2/1996 | Lu et al. |

(56) References Cited

U.S. PATENT DOCUMENTS

| | | |
|---|---|---|
| 5,496,273 A | 3/1996 | Pastrone et al. |
| 5,505,828 A | 4/1996 | Wong et al. |
| 5,507,288 A | 4/1996 | Bocker et al. |
| 5,507,786 A | 4/1996 | Morgan et al. |
| 5,508,499 A | 4/1996 | Ferrario |
| 5,515,713 A | 5/1996 | Saugues et al. |
| 5,520,637 A | 5/1996 | Pager et al. |
| 5,522,798 A | 6/1996 | Johnson et al. |
| 5,547,470 A | 8/1996 | Johnson et al. |
| 5,554,013 A | 9/1996 | Owens et al. |
| 5,562,615 A | 10/1996 | Nassif |
| 5,577,169 A | 11/1996 | Prezioso |
| 5,582,323 A | 12/1996 | Kurtenbach |
| 5,582,593 A | 12/1996 | Hultman |
| 5,594,786 A | 1/1997 | Chaco et al. |
| 5,598,519 A | 1/1997 | Narayanan |
| 5,620,608 A | 4/1997 | Rosa et al. |
| 5,630,710 A | 5/1997 | Tune et al. |
| 5,636,044 A | 6/1997 | Yuan et al. |
| 5,643,212 A | 7/1997 | Coutre et al. |
| 5,651,775 A | 7/1997 | Walker et al. |
| 5,658,131 A | 8/1997 | Aoki et al. |
| 5,658,250 A | 8/1997 | Blomquist et al. |
| 5,665,065 A | 9/1997 | Colman et al. |
| 5,669,877 A | 9/1997 | Blomquist |
| 5,672,154 A | 9/1997 | Sillén et al. |
| 5,681,285 A | 10/1997 | Ford et al. |
| 5,685,844 A | 11/1997 | Marttila |
| 5,687,717 A | 11/1997 | Halpern et al. |
| 5,689,229 A | 11/1997 | Chaco et al. |
| 5,697,899 A | 12/1997 | Hillman et al. |
| 5,699,509 A | 12/1997 | Gary et al. |
| 5,708,714 A | 1/1998 | Lopez et al. |
| 5,713,350 A | 2/1998 | Yokota et al. |
| 5,713,856 A | 2/1998 | Eggers et al. |
| 5,718,562 A | 2/1998 | Lawless et al. |
| 5,719,761 A | 2/1998 | Gatti et al. |
| 5,733,259 A | 3/1998 | Valcke et al. |
| 5,738,102 A | 4/1998 | Lemelson |
| 5,744,027 A | 4/1998 | Connell et al. |
| 5,752,621 A | 5/1998 | Passamante |
| 5,754,111 A | 5/1998 | Garcia |
| 5,764,034 A | 6/1998 | Bowman et al. |
| 5,764,159 A | 6/1998 | Neftel et al. |
| 5,772,635 A | 6/1998 | Dastur et al. |
| 5,774,865 A | 6/1998 | Glynn |
| 5,778,256 A | 7/1998 | Darbee |
| 5,778,345 A | 7/1998 | McCartney |
| 5,781,442 A | 7/1998 | Engleson et al. |
| 5,782,805 A | 7/1998 | Meinzer et al. |
| 5,788,669 A | 8/1998 | Peterson |
| 5,797,515 A | 8/1998 | Liff et al. |
| 5,800,387 A | 9/1998 | Duffy et al. |
| 5,814,015 A | 9/1998 | Gargano et al. |
| 5,822,544 A | 10/1998 | Chaco et al. |
| 5,822,715 A | 10/1998 | Worthington et al. |
| 5,827,179 A | 10/1998 | Lichter et al. |
| 5,832,448 A | 11/1998 | Brown |
| 5,836,910 A | 11/1998 | Duffy et al. |
| 5,850,344 A | 12/1998 | Conkright |
| 5,867,821 A | 2/1999 | Ballantyne et al. |
| 5,870,733 A | 2/1999 | Bass et al. |
| 5,871,465 A | 2/1999 | Vasko |
| 5,873,731 A | 2/1999 | Predergast |
| 5,885,245 A | 3/1999 | Lynch et al. |
| 5,897,493 A | 4/1999 | Brown |
| 5,897,498 A | 4/1999 | Canfield, II et al. |
| 5,910,252 A | 6/1999 | Truitt et al. |
| 5,912,818 A | 6/1999 | McGrady et al. |
| 5,915,240 A | 6/1999 | Karpf |
| 5,920,054 A | 7/1999 | Uber, III |
| 5,920,263 A | 7/1999 | Huttenhoff et al. |
| 5,924,074 A | 7/1999 | Evans |
| 5,931,764 A | 8/1999 | Freeman et al. |
| 5,935,099 A | 8/1999 | Peterson et al. |
| 5,935,106 A | 8/1999 | Olsen |
| 5,941,846 A | 8/1999 | Duffy et al. |
| 5,956,501 A | 9/1999 | Brown |
| 5,957,885 A | 9/1999 | Bollish et al. |
| 5,960,085 A | 9/1999 | de la Huerga |
| 5,961,448 A | 10/1999 | Swenson et al. |
| 5,967,559 A | 10/1999 | Abramowitz |
| 5,971,594 A | 10/1999 | Sahai et al. |
| 5,975,081 A | 11/1999 | Hood et al. |
| 5,990,838 A | 11/1999 | Burns et al. |
| 5,997,476 A | 12/1999 | Brown |
| 6,000,828 A | 12/1999 | Leet |
| 6,003,006 A | 12/1999 | Colella et al. |
| 6,012,034 A | 1/2000 | Hamparian et al. |
| 6,017,318 A | 1/2000 | Gauthier et al. |
| 6,021,392 A | 2/2000 | Lester et al. |
| 6,024,539 A | 2/2000 | Blomquist |
| 6,024,699 A | 2/2000 | Surwit et al. |
| 6,032,155 A | 2/2000 | de la Huerga |
| 6,032,676 A | 3/2000 | Moore |
| 6,039,251 A | 3/2000 | Holowko et al. |
| 6,070,761 A | 6/2000 | Bloom et al. |
| 6,073,106 A | 6/2000 | Rozen et al. |
| 6,104,295 A | 8/2000 | Gaisser et al. |
| 6,112,182 A | 8/2000 | Akers et al. |
| 6,112,323 A | 8/2000 | Meizlik et al. |
| RE36,871 E | 9/2000 | Epstein et al. |
| 6,115,365 A | 9/2000 | Newberg |
| 6,115,390 A | 9/2000 | Chuah |
| 6,122,536 A | 9/2000 | Sun et al. |
| 6,126,637 A | 10/2000 | Kriesel et al. |
| 6,135,949 A | 10/2000 | Russo et al. |
| 6,150,942 A | 11/2000 | O'Brien |
| 6,151,643 A | 11/2000 | Cheng et al. |
| 6,157,914 A | 12/2000 | Seto et al. |
| 6,159,147 A | 12/2000 | Lichter et al. |
| 6,167,567 A | 12/2000 | Chiles et al. |
| 6,182,667 B1 | 2/2001 | Hanks et al. |
| 6,189,105 B1 | 2/2001 | Lopes |
| 6,195,589 B1 | 2/2001 | Ketcham |
| 6,208,974 B1 | 3/2001 | Campbell et al. |
| 6,222,323 B1 | 4/2001 | Yamashita et al. |
| 6,223,440 B1 | 5/2001 | Rashman |
| 6,226,277 B1 | 5/2001 | Chuah |
| 6,227,371 B1 | 5/2001 | Song |
| 6,234,176 B1 | 5/2001 | Domae et al. |
| 6,241,704 B1 | 6/2001 | Peterson et al. |
| 6,248,067 B1 | 6/2001 | Causey, III et al. |
| 6,249,705 B1 | 6/2001 | Snell |
| 6,257,265 B1 | 7/2001 | Brunner et al. |
| 6,259,355 B1 | 7/2001 | Chaco et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,280,380 B1 | 8/2001 | Bardy |
| 6,283,761 B1 | 9/2001 | Joao |
| 6,285,665 B1 | 9/2001 | Chuah |
| 6,292,860 B1 | 9/2001 | Cochcroft, Jr. |
| 6,312,378 B1 | 11/2001 | Bardy |
| 6,327,254 B1 | 12/2001 | Chuah |
| 6,330,008 B1 | 12/2001 | Razdow et al. |
| 6,339,718 B1 | 1/2002 | Zatezalo et al. |
| 6,346,886 B1 | 2/2002 | de la Huerga |
| 6,363,282 B1 | 3/2002 | Nichols et al. |
| 6,371,719 B1 | 4/2002 | Hildebrandt |
| 6,377,548 B1 | 4/2002 | Chuah |
| 6,388,951 B1 | 5/2002 | Matsumoto et al. |
| 6,406,426 B1 | 6/2002 | Reuss et al. |
| 6,408,330 B1 | 6/2002 | Huerga |
| 6,418,334 B1 | 7/2002 | Unger et al. |
| 6,427,088 B1 | 7/2002 | Bowman et al. |
| 6,428,483 B1 | 8/2002 | Carlebach |
| 6,442,432 B2 | 8/2002 | Lee |
| 6,469,991 B1 | 10/2002 | Chuah |
| 6,475,180 B2 | 11/2002 | Peterson et al. |
| 6,482,158 B2 | 11/2002 | Mault |
| 6,485,418 B2 | 11/2002 | Yasushi et al. |
| 6,494,694 B2 | 12/2002 | Lawless et al. |

(56) References Cited

U.S. PATENT DOCUMENTS

| | | |
|---|---|---|
| 6,494,831 B1 | 12/2002 | Koritzinsky |
| 6,497,680 B1 | 12/2002 | Holst et al. |
| 6,514,460 B1 | 2/2003 | Fendrock |
| 6,517,482 B1 | 2/2003 | Eiden et al. |
| 6,519,569 B1 | 2/2003 | White et al. |
| 6,520,930 B2 | 2/2003 | Critchlow et al. |
| 6,540,672 B1 | 4/2003 | Simonsen et al. |
| 6,542,902 B2 | 4/2003 | Dulong et al. |
| 6,544,212 B2 | 4/2003 | Galley et al. |
| 6,544,228 B1 | 4/2003 | Heitmeier |
| 6,546,350 B1 | 4/2003 | Hartmann et al. |
| 6,551,276 B1 | 4/2003 | Mann et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,565,509 B1 | 5/2003 | Say et al. |
| 6,567,416 B1 | 5/2003 | Chuah |
| 6,571,294 B2 | 5/2003 | Simmon et al. |
| 6,572,542 B1 | 6/2003 | Houben et al. |
| 6,572,545 B2 | 6/2003 | Knobbe et al. |
| 6,578,002 B1 | 6/2003 | Derzay et al. |
| 6,581,117 B1 | 6/2003 | Klein et al. |
| 6,587,034 B1 | 7/2003 | Heiman et al. |
| 6,589,229 B1 | 7/2003 | Connelly et al. |
| 6,599,281 B1 | 7/2003 | Struys et al. |
| 6,602,191 B2 | 8/2003 | Quy |
| 6,605,072 B2 | 8/2003 | Struys et al. |
| 6,628,809 B1 | 9/2003 | Rowe et al. |
| 6,631,353 B1 | 10/2003 | Davis et al. |
| 6,640,246 B1 | 10/2003 | Gardy, Jr. et al. |
| 6,641,533 B2 | 11/2003 | Causey, III et al. |
| 6,647,299 B2 | 11/2003 | Bourget |
| 6,652,455 B1 | 11/2003 | Kocher |
| 6,653,937 B2 | 11/2003 | Nelson et al. |
| 6,659,947 B1 | 12/2003 | Carter et al. |
| 6,669,630 B1 | 12/2003 | Joliat et al. |
| 6,671,563 B1 | 12/2003 | Engleson et al. |
| 6,673,033 B1 | 1/2004 | Sciulli et al. |
| 6,674,403 B2 | 1/2004 | Gray et al. |
| 6,681,003 B2 | 1/2004 | Linder et al. |
| 6,689,091 B2 | 2/2004 | Bui et al. |
| 6,692,241 B2 | 2/2004 | Watanabe et al. |
| 6,694,191 B2 | 2/2004 | Starkweather et al. |
| 6,694,334 B2 | 2/2004 | DuLong et al. |
| 6,721,286 B1 | 4/2004 | Williams et al. |
| 6,721,582 B2 | 4/2004 | Trepagnier et al. |
| 6,725,200 B1 | 4/2004 | Rost |
| 6,731,989 B2 | 5/2004 | Engleson et al. |
| 6,740,072 B2 | 5/2004 | Starkweather et al. |
| 6,751,651 B2 | 6/2004 | Crockett |
| 6,752,787 B1 | 6/2004 | Causey, III et al. |
| 6,753,830 B2 | 6/2004 | Gelbman |
| 6,758,810 B2 | 7/2004 | Lebel et al. |
| 6,773,396 B2 | 8/2004 | Flach et al. |
| 6,774,786 B1 | 8/2004 | Havekost et al. |
| 6,775,577 B2 | 8/2004 | Cmkovich et al. |
| 6,780,156 B2 | 8/2004 | Haueter et al. |
| 6,790,198 B1 | 9/2004 | White et al. |
| 6,792,470 B2 | 9/2004 | Hakenberg et al. |
| 6,796,956 B2 | 9/2004 | Hartlaub et al. |
| 6,799,149 B2 | 9/2004 | Hartlaub |
| 6,809,653 B1 | 10/2004 | Mann et al. |
| 6,811,534 B2 | 11/2004 | Bowman, IV et al. |
| 6,816,605 B2 | 11/2004 | Rowe et al. |
| 6,839,753 B2 | 1/2005 | Biondi et al. |
| 6,852,104 B2 | 2/2005 | Blomquist |
| 6,859,134 B1 | 2/2005 | Heiman et al. |
| 6,871,211 B2 | 3/2005 | Labounty et al. |
| 6,873,268 B2 | 3/2005 | Lebel et al. |
| 6,876,303 B2 | 4/2005 | Reeder et al. |
| 6,885,881 B2 | 4/2005 | Leonhardt |
| 6,891,525 B2 | 5/2005 | Ogoro |
| 6,892,278 B2 | 5/2005 | Ebergen |
| 6,899,695 B2 | 5/2005 | Herrera |
| 6,915,170 B2 | 7/2005 | Engleson et al. |
| 6,923,763 B1 | 8/2005 | Kovatchev et al. |
| 6,924,781 B1 | 8/2005 | Gelbman |
| 6,928,338 B1 | 8/2005 | Buchser et al. |
| 6,928,490 B1 | 8/2005 | Bucholz et al. |
| 6,936,029 B2 | 8/2005 | Mann et al. |
| 6,945,954 B2 | 9/2005 | Hochman et al. |
| 6,948,492 B2 | 9/2005 | Wemeling et al. |
| 6,958,677 B1 | 10/2005 | Carter |
| 6,958,691 B1 | 10/2005 | Anderson et al. |
| 6,958,705 B2 | 10/2005 | Lebel et al. |
| 6,961,448 B2 | 11/2005 | Nichols et al. |
| 6,969,352 B2 | 11/2005 | Chiang et al. |
| 6,969,865 B2 | 11/2005 | Duchon et al. |
| 6,974,437 B2 | 12/2005 | Lebel et al. |
| 6,979,326 B2 | 12/2005 | Mann et al. |
| 6,980,958 B1 | 12/2005 | Surwit et al. |
| 6,985,870 B2 | 1/2006 | Martucci et al. |
| 6,986,347 B2 | 1/2006 | Hickle |
| 6,997,880 B2 | 2/2006 | Carlebach et al. |
| 6,997,920 B2 | 2/2006 | Mann et al. |
| 6,998,984 B1 | 2/2006 | Zittrain |
| 7,016,752 B1 | 3/2006 | Ruben et al. |
| 7,017,293 B2 | 3/2006 | Riley |
| 7,025,743 B2 | 4/2006 | Mann et al. |
| 7,029,455 B2 | 4/2006 | Flaherty |
| 7,038,584 B2 | 5/2006 | Carter |
| 7,060,031 B2 | 6/2006 | Webb et al. |
| 7,060,059 B2 | 6/2006 | Keith et al. |
| 7,069,552 B2 | 6/2006 | Lindberg et al. |
| 7,072,725 B2 | 7/2006 | Bristol et al. |
| 7,079,035 B2 | 7/2006 | Bock et al. |
| 7,092,943 B2 | 8/2006 | Roese et al. |
| 7,096,072 B2 | 8/2006 | Engleson et al. |
| 7,099,809 B2 | 8/2006 | Dori |
| 7,103,419 B2 | 9/2006 | Engleson et al. |
| 7,103,578 B2 | 9/2006 | Beck et al. |
| 7,107,106 B2 | 9/2006 | Engleson et al. |
| 7,108,680 B2 | 9/2006 | Rohr et al. |
| 7,109,878 B2 | 9/2006 | Mann et al. |
| 7,114,002 B1 | 9/2006 | Okumura et al. |
| 7,117,041 B2 | 10/2006 | Engleson et al. |
| 7,136,645 B2 | 11/2006 | Hanson et al. |
| 7,137,964 B2 | 11/2006 | Flaherty |
| 7,142,190 B2 | 11/2006 | Martinez |
| 7,150,741 B2 | 12/2006 | Erickson et al. |
| 7,153,289 B2 | 12/2006 | Vasko |
| 7,154,397 B2 | 12/2006 | Zerhusen et al. |
| 7,156,807 B2 | 1/2007 | Carter et al. |
| 7,158,030 B2 | 1/2007 | Chung |
| 7,161,484 B2 | 1/2007 | Tsoukalis et al. |
| 7,167,755 B2 | 1/2007 | Seeberger et al. |
| 7,167,920 B2 | 1/2007 | Traversat |
| 7,171,277 B2 | 1/2007 | Engleson et al. |
| 7,171,492 B1 | 1/2007 | Borella et al. |
| 7,181,493 B2 | 2/2007 | English et al. |
| 7,185,288 B2 | 2/2007 | McKeever |
| 7,193,514 B2 | 3/2007 | Ritson |
| 7,197,025 B2 | 3/2007 | Chuah |
| 7,201,734 B2 | 4/2007 | Hickle |
| 7,204,823 B2 | 4/2007 | Estes et al. |
| 7,213,009 B2 | 5/2007 | Pestotnik |
| 7,216,802 B1 | 5/2007 | de la Huerga |
| 7,220,240 B2 | 5/2007 | Struys et al. |
| 7,224,979 B2 | 5/2007 | Singhal et al. |
| 7,229,430 B2 | 6/2007 | Hickle et al. |
| 7,230,529 B2 | 6/2007 | Ketcherside |
| 7,236,936 B2 | 6/2007 | White et al. |
| 7,238,164 B2 | 7/2007 | Childers et al. |
| 7,247,154 B2 | 7/2007 | Hickle |
| 7,248,239 B2 | 7/2007 | Dowling |
| 7,250,856 B2 | 7/2007 | Havekost et al. |
| 7,255,683 B2 | 8/2007 | Vanderveen et al. |
| 7,256,888 B2 | 8/2007 | Staehr et al. |
| 7,258,534 B2 | 8/2007 | Fathallah et al. |
| 7,263,213 B2 | 8/2007 | Rowe |
| 7,267,664 B2 | 9/2007 | Rizzo |
| 7,267,665 B2 | 9/2007 | Steil et al. |
| 7,275,156 B2 | 9/2007 | Balfanz et al. |
| 7,278,983 B2 | 10/2007 | Ireland et al. |

(56) References Cited

U.S. PATENT DOCUMENTS

| | | |
|---|---|---|
| 7,289,815 B2 | 10/2007 | Gfeller et al. |
| 7,289,948 B1 | 10/2007 | Mohri |
| 7,293,107 B1 | 11/2007 | Hanson et al. |
| 7,295,119 B2 | 11/2007 | Rappaport et al. |
| 7,295,556 B2 | 11/2007 | Roese et al. |
| 7,301,451 B2 | 11/2007 | Hastings |
| 7,308,300 B2 | 12/2007 | Toews et al. |
| 7,315,825 B2 | 1/2008 | Rosenfeld et al. |
| 7,319,386 B2 | 1/2008 | Collins, Jr. et al. |
| 7,324,000 B2 | 1/2008 | Zittrain et al. |
| 7,327,705 B2 | 2/2008 | Fletcher et al. |
| 7,343,224 B2 | 3/2008 | DiGianfilippo et al. |
| 7,346,025 B2 | 3/2008 | Bryson |
| 7,347,836 B2 | 3/2008 | Peterson et al. |
| 7,354,420 B2 | 4/2008 | Steil et al. |
| 7,369,897 B2 | 5/2008 | Boveja et al. |
| 7,369,948 B1 | 5/2008 | Ferenczi et al. |
| 7,383,088 B2 | 6/2008 | Spinelli et al. |
| 7,384,410 B2 | 6/2008 | Eggers et al. |
| 7,398,183 B2 | 7/2008 | Holland et al. |
| 7,398,279 B2 | 7/2008 | Muno, Jr. et al. |
| 7,399,277 B2 | 7/2008 | Saidara et al. |
| 7,402,153 B2 | 7/2008 | Steil et al. |
| 7,420,472 B2 | 9/2008 | Tran |
| 7,432,807 B2 | 10/2008 | Schmitt |
| 7,436,454 B2 | 10/2008 | Yamaguchi et al. |
| 7,447,643 B1 | 11/2008 | Olson |
| 7,454,314 B2 | 11/2008 | Holland et al. |
| 7,457,804 B2 | 11/2008 | Uber, III et al. |
| 7,464,040 B2 | 12/2008 | Joao |
| 7,469,213 B1 | 12/2008 | Rao |
| 7,471,994 B2 | 12/2008 | Ford et al. |
| 7,483,756 B2 | 1/2009 | Engleson et al. |
| 7,489,808 B2 | 2/2009 | Gerder |
| 7,490,021 B2 | 2/2009 | Holland et al. |
| 7,490,048 B2 | 2/2009 | Joao |
| 7,491,187 B2 | 2/2009 | Van Den Berghe et al. |
| 7,519,905 B2 | 4/2009 | Kougiouris et al. |
| 7,523,401 B1 | 4/2009 | Aldridge |
| 7,524,304 B2 | 4/2009 | Genosar |
| 7,551,078 B2 | 6/2009 | Carlson |
| 7,559,321 B2 | 7/2009 | Wermeling et al. |
| 7,565,197 B2 | 7/2009 | Haulbrich et al. |
| 7,572,230 B2 | 8/2009 | Neumann et al. |
| 7,578,802 B2 | 8/2009 | Hickle |
| 7,621,009 B2 | 11/2009 | Elhabashy |
| D606,533 S | 12/2009 | De Jong et al. |
| 7,636,718 B1 | 12/2009 | Steen et al. |
| 7,640,172 B2 | 12/2009 | Kuth |
| 7,645,258 B2 | 1/2010 | White et al. |
| 7,647,237 B2 | 1/2010 | Malave et al. |
| 7,662,124 B2 | 2/2010 | Duchon et al. |
| 7,668,731 B2 | 2/2010 | Martucci et al. |
| 7,671,733 B2 | 3/2010 | McNeal et al. |
| 7,678,071 B2 | 3/2010 | Lebel et al. |
| 7,687,678 B2 | 3/2010 | Jacobs |
| 7,697,994 B2 | 4/2010 | VanDanacker et al. |
| 7,698,239 B2 | 4/2010 | Lieuallen |
| 7,705,727 B2 | 4/2010 | Pestotnik |
| 7,724,147 B2 | 5/2010 | Brown et al. |
| 7,739,126 B1 | 6/2010 | Cave |
| 7,746,218 B2 | 6/2010 | Collins, Jr. |
| 7,766,873 B2 | 8/2010 | Moberg et al. |
| 7,776,029 B2 | 8/2010 | Whitehurst et al. |
| 7,776,031 B2 | 8/2010 | Hartlaub et al. |
| 7,785,313 B2 | 8/2010 | Mastrototaro |
| 7,788,369 B2 | 8/2010 | McAllen et al. |
| 7,806,852 B1 | 10/2010 | Jurson |
| 7,806,886 B2 | 10/2010 | Kanderian, Jr. et al. |
| 7,826,981 B2 | 11/2010 | Goode, Jr. et al. |
| 7,835,927 B2 | 11/2010 | Schlotterbeck et al. |
| 7,836,314 B2 | 11/2010 | Chieu |
| 7,856,276 B2 | 12/2010 | Ripart et al. |
| 7,860,583 B2 | 12/2010 | Condurso et al. |
| 7,864,771 B2 | 1/2011 | Tavares et al. |
| 7,868,754 B2 | 1/2011 | Salvat, Jr. |
| 7,871,394 B2 | 1/2011 | Halbert et al. |
| 7,886,231 B2 | 2/2011 | Hopermann et al. |
| 7,895,053 B2 | 2/2011 | Holland et al. |
| 7,896,842 B2 | 3/2011 | Palmroos et al. |
| 7,899,546 B2 | 3/2011 | Sieracki et al. |
| 7,905,710 B2 | 3/2011 | Wang et al. |
| 7,920,061 B2 | 4/2011 | Klein et al. |
| 7,933,780 B2 | 4/2011 | de la Huerga |
| 7,938,796 B2 | 5/2011 | Moubayed |
| 7,945,452 B2 | 5/2011 | Fathallah et al. |
| 7,974,714 B2 | 7/2011 | Hoffberg |
| 7,976,508 B2 | 7/2011 | Hoag |
| 7,996,241 B2 | 8/2011 | Zak |
| 8,034,026 B2 | 10/2011 | Grant |
| 8,038,593 B2 | 10/2011 | Friedman et al. |
| 8,048,040 B2 | 11/2011 | Kiani |
| 8,060,576 B2 | 11/2011 | Chan et al. |
| 8,065,161 B2 | 11/2011 | Howard et al. |
| 8,066,672 B2 | 11/2011 | Mandro |
| 8,075,514 B2 | 12/2011 | Butterfield et al. |
| 8,078,983 B2 | 12/2011 | Davis et al. |
| 8,082,018 B2 | 12/2011 | Duchon et al. |
| 8,082,312 B2 | 12/2011 | Chan et al. |
| 8,095,692 B2 | 1/2012 | Mehta et al. |
| 8,126,730 B2 | 2/2012 | Dicks et al. |
| 8,147,448 B2 | 4/2012 | Sundar et al. |
| 8,149,131 B2 | 4/2012 | Blomquist |
| 8,169,914 B2 | 5/2012 | Bajpai |
| 8,171,094 B2 | 5/2012 | Chan et al. |
| 8,172,798 B2 | 5/2012 | Hungerford et al. |
| 8,185,322 B2 | 5/2012 | Schroeder et al. |
| 8,195,478 B2 | 6/2012 | Petersen et al. |
| 8,206,350 B2 | 6/2012 | Mann et al. |
| 8,219,413 B2 | 7/2012 | Martinez et al. |
| 8,231,578 B2 | 7/2012 | Fathallah et al. |
| 8,234,128 B2 | 7/2012 | Martucci et al. |
| 8,267,892 B2 | 9/2012 | Spencer et al. |
| 8,271,106 B2 | 9/2012 | Wehba et al. |
| 8,287,495 B2 | 10/2012 | Michaud et al. |
| 8,291,337 B2 | 10/2012 | Gannin et al. |
| 8,298,184 B2 | 10/2012 | DiPerna et al. |
| 8,312,272 B1 | 11/2012 | Serenyl et al. |
| 8,352,290 B2 | 1/2013 | Bartz et al. |
| 8,359,338 B2 | 1/2013 | Butterfield et al. |
| 8,380,536 B2 | 2/2013 | Howard et al. |
| 8,387,112 B1 | 2/2013 | Ranjan et al. |
| 8,394,077 B2 | 3/2013 | Jacobson et al. |
| 8,398,592 B2 | 3/2013 | Leibner-Druska |
| 8,403,908 B2 | 3/2013 | Jacobson et al. |
| 8,435,206 B2 | 5/2013 | Evans et al. |
| 8,449,523 B2 | 5/2013 | Brukalo et al. |
| 8,452,953 B2 | 5/2013 | Buck et al. |
| 8,453,645 B2 | 6/2013 | Figueiredo et al. |
| 8,472,630 B2 | 6/2013 | Konrad et al. |
| 8,480,648 B2 | 7/2013 | Burnett et al. |
| 8,486,019 B2 | 7/2013 | White et al. |
| 8,489,427 B2 | 7/2013 | Simpson et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,543,416 B2 | 9/2013 | Palmroos et al. |
| 8,551,038 B2 | 10/2013 | Tsoukalis et al. |
| 8,560,345 B2 | 10/2013 | Wehba et al. |
| 8,567,681 B2 | 10/2013 | Borges et al. |
| 8,577,692 B2 | 11/2013 | Silkaitis et al. |
| 8,579,884 B2 | 11/2013 | Lanier et al. |
| 8,626,530 B1 | 1/2014 | Tran et al. |
| 8,655,676 B2 | 2/2014 | Wehba et al. |
| 8,660,860 B2 | 2/2014 | Wehba et al. |
| 8,662,388 B2 | 3/2014 | Belkin |
| 8,666,769 B2 | 3/2014 | Butler et al. |
| 8,667,293 B2 | 3/2014 | Birtwhistle et al. |
| 8,687,811 B2 | 4/2014 | Nierzwick et al. |
| 8,700,421 B2 | 4/2014 | Feng et al. |
| 8,731,960 B2 | 5/2014 | Butler et al. |
| 8,768,719 B2 | 7/2014 | Wehba et al. |
| 8,771,251 B2 | 7/2014 | Ruchti et al. |

(56) References Cited

U.S. PATENT DOCUMENTS

| | | |
|---|---|---|
| 8,777,894 B2 | 7/2014 | Butterfield et al. |
| 8,777,895 B2 | 7/2014 | Hsu et al. |
| 8,799,012 B2 | 8/2014 | Butler et al. |
| 8,876,793 B2 | 11/2014 | Ledford et al. |
| 8,886,316 B1 | 11/2014 | Juels |
| 8,922,330 B2 | 12/2014 | Moberg et al. |
| 8,936,565 B2 | 1/2015 | Chawla |
| 8,945,043 B2 | 2/2015 | Lee et al. |
| 8,952,794 B2 | 2/2015 | Blomquist et al. |
| 8,959,617 B2 | 2/2015 | Newlin et al. |
| 8,998,100 B2 | 4/2015 | Halbert et al. |
| 9,026,370 B2 | 5/2015 | Rubalcaba et al. |
| 9,069,887 B2 | 6/2015 | Gupta et al. |
| 9,077,544 B2 | 7/2015 | Baker et al. |
| 9,089,642 B2 | 7/2015 | Murphy et al. |
| 9,114,217 B2 | 8/2015 | Sur et al. |
| 9,123,077 B2 | 9/2015 | Silkaitis et al. |
| 9,192,712 B2 | 11/2015 | DeBelser et al. |
| 9,240,002 B2 | 1/2016 | Hume et al. |
| 9,292,692 B2 | 3/2016 | Wallrabenstein |
| 9,302,035 B2 | 4/2016 | Marseille et al. |
| 9,313,154 B1 | 4/2016 | Son |
| 9,381,296 B2 | 7/2016 | Arrizza et al. |
| 9,393,362 B2 | 7/2016 | Cozmi et al. |
| 9,430,655 B1 | 8/2016 | Stockton et al. |
| 9,438,580 B2 | 9/2016 | Kupper |
| 9,483,615 B2 | 11/2016 | Roberts |
| 9,498,583 B2 | 11/2016 | Sur et al. |
| 9,539,383 B2 | 1/2017 | Kohlbrecher |
| 9,572,923 B2 | 2/2017 | Howard et al. |
| 9,594,875 B2 | 3/2017 | Arrizza et al. |
| 9,604,000 B2 | 3/2017 | Wehba et al. |
| 9,641,432 B2 | 5/2017 | Jha et al. |
| 9,649,431 B2 | 5/2017 | Gray et al. |
| 9,662,436 B2 | 5/2017 | Belkin et al. |
| 9,690,909 B2 | 6/2017 | Stewart et al. |
| 9,707,341 B2 | 7/2017 | Dumas, III et al. |
| 9,717,845 B2 | 8/2017 | Istoc |
| 9,724,470 B2 | 8/2017 | Day et al. |
| 9,764,082 B2 | 9/2017 | Day et al. |
| 9,886,550 B2 | 2/2018 | Lee et al. |
| 9,943,269 B2 | 4/2018 | Muhsin et al. |
| 9,967,739 B2 | 5/2018 | Proennecke et al. |
| 9,971,871 B2 | 5/2018 | Arrizza et al. |
| 9,995,611 B2 | 6/2018 | Ruchti et al. |
| 10,022,498 B2 | 7/2018 | Ruchti et al. |
| 10,042,986 B2 | 8/2018 | Ruchti et al. |
| 10,046,112 B2 | 8/2018 | Oruklu et al. |
| 10,166,328 B2 | 1/2019 | Oruklu et al. |
| 10,173,008 B2 | 1/2019 | Simpson et al. |
| 10,188,849 B2 | 1/2019 | Fangrow |
| 10,233,179 B2 | 3/2019 | Ng et al. |
| 10,238,799 B2 | 3/2019 | Kohlbrecher |
| 10,238,801 B2 | 3/2019 | Wehba et al. |
| 10,242,060 B2 | 3/2019 | Butler et al. |
| 10,300,194 B2 | 5/2019 | Day et al. |
| 10,311,972 B2 | 6/2019 | Kohlbrecher et al. |
| 10,314,974 B2 | 6/2019 | Day et al. |
| 10,333,843 B2 | 6/2019 | Jha et al. |
| 10,341,866 B1 | 7/2019 | Spencer et al. |
| 10,409,995 B1 | 9/2019 | Wasiq |
| 10,430,761 B2 | 10/2019 | Hume et al. |
| 10,434,246 B2 | 10/2019 | Silkaitis et al. |
| 10,438,001 B1 | 10/2019 | Hariprasad |
| 10,452,842 B2 | 10/2019 | Dhondse |
| 10,453,157 B2 | 10/2019 | Kamen et al. |
| 10,463,788 B2 | 11/2019 | Day |
| 10,516,536 B2 | 12/2019 | Rommel |
| 10,617,815 B2 | 4/2020 | Day et al. |
| 10,646,651 B2 | 5/2020 | Day et al. |
| 10,681,207 B1 | 6/2020 | Johnson et al. |
| 10,692,595 B2 | 6/2020 | Xavier et al. |
| 10,728,262 B1 | 7/2020 | Vaswani |
| 10,740,436 B2 | 8/2020 | Moskal et al. |
| 10,741,280 B2 | 8/2020 | Xavier et al. |
| 10,757,219 B2 | 8/2020 | Moskal |
| 10,765,799 B2 | 9/2020 | Belkin et al. |
| 10,799,632 B2 | 10/2020 | Kohlbrecher |
| 10,812,380 B2 | 10/2020 | Jha et al. |
| 10,861,592 B2 | 12/2020 | Xavier et al. |
| 10,898,641 B2 | 1/2021 | Day et al. |
| 10,950,339 B2 | 3/2021 | Xavier et al. |
| 10,964,428 B2 | 3/2021 | Xavier et al. |
| 11,013,861 B2 | 5/2021 | Wehba et al. |
| 11,037,668 B2 | 6/2021 | Ruchti et al. |
| 11,052,193 B2 | 7/2021 | Day et al. |
| 11,139,058 B2 | 10/2021 | Xavier et al. |
| 11,151,290 B2 | 10/2021 | Karakoyunlu et al. |
| 11,152,108 B2 | 10/2021 | Xavier et al. |
| 11,152,109 B2 | 10/2021 | Xavier et al. |
| 11,152,110 B2 | 10/2021 | Xavier et al. |
| 11,194,810 B2 | 12/2021 | Butler et al. |
| 11,235,100 B2 | 2/2022 | Howard et al. |
| 11,289,183 B2 | 3/2022 | Kohlbrecher |
| 11,309,070 B2 | 4/2022 | Xavier et al. |
| 11,328,804 B2 | 5/2022 | Xavier et al. |
| 11,328,805 B2 | 5/2022 | Xavier et al. |
| 11,373,753 B2 | 6/2022 | Xavier et al. |
| 11,437,132 B2 | 9/2022 | Xavier et al. |
| 11,470,000 B2 | 10/2022 | Jha et al. |
| 11,483,402 B2 | 10/2022 | Xavier et al. |
| 11,483,403 B2 | 10/2022 | Xavier et al. |
| 11,501,877 B2 | 11/2022 | Kohlbrecher et al. |
| 11,571,508 B2 | 2/2023 | Jacobson et al. |
| 11,574,721 B2 | 2/2023 | Kohlbrecher |
| 11,574,737 B2 | 2/2023 | Dharwad et al. |
| 11,587,669 B2 | 2/2023 | Xavier et al. |
| 11,590,057 B2 | 2/2023 | Tagliamento et al. |
| 11,594,326 B2 | 2/2023 | Xavier et al. |
| 11,605,468 B2 | 3/2023 | Jacobson et al. |
| 11,626,205 B2 | 4/2023 | Arrizza et al. |
| 11,628,246 B2 | 4/2023 | Day et al. |
| 11,628,254 B2 | 4/2023 | Day et al. |
| 11,654,237 B2 | 5/2023 | Wehba et al. |
| 11,670,416 B2 | 6/2023 | Xavier et al. |
| 11,763,927 B2 | 9/2023 | Ruchti et al. |
| 11,783,935 B2 | 10/2023 | Xavier et al. |
| 11,881,297 B2 | 1/2024 | Xavier et al. |
| 11,923,076 B2 | 3/2024 | Xavier et al. |
| 11,986,623 B2 | 5/2024 | Jacobson et al. |
| 11,996,188 B2 | 5/2024 | Arrizza et al. |
| 12,002,562 B2 | 6/2024 | Kohlbrecher |
| 12,036,390 B2 | 7/2024 | Wehba et al. |
| 12,040,068 B2 | 7/2024 | Xavier et al. |
| 12,042,623 B2 | 7/2024 | Day et al. |
| 12,042,631 B2 | 7/2024 | Day et al. |
| 12,046,361 B2 | 7/2024 | Xavier et al. |
| 12,047,292 B2 | 7/2024 | Jha et al. |
| 12,097,351 B2 | 9/2024 | Belkin et al. |
| 2001/0016056 A1 | 8/2001 | Westphal et al. |
| 2001/0029178 A1 | 10/2001 | Criss et al. |
| 2001/0031944 A1 | 10/2001 | Peterson et al. |
| 2001/0032099 A1 | 10/2001 | Joao |
| 2001/0037060 A1 | 11/2001 | Thompson et al. |
| 2001/0044731 A1 | 11/2001 | Coffman et al. |
| 2001/0048027 A1 | 12/2001 | Walsh |
| 2001/0051787 A1 | 12/2001 | Haller et al. |
| 2001/0056358 A1 | 12/2001 | Dulong et al. |
| 2002/0010595 A1 | 1/2002 | Kapp |
| 2002/0013551 A1 | 1/2002 | Zaitsu et al. |
| 2002/0013723 A1 | 1/2002 | Mise |
| 2002/0015018 A1 | 2/2002 | Shimazu et al. |
| 2002/0019584 A1 | 2/2002 | Schulze et al. |
| 2002/0021700 A1 | 2/2002 | Hata et al. |
| 2002/0026103 A1 | 2/2002 | Norris et al. |
| 2002/0029776 A1 | 3/2002 | Blomquist |
| 2002/0032583 A1 | 3/2002 | Joao |
| 2002/0040208 A1 | 4/2002 | Flaherty et al. |
| 2002/0040282 A1 | 4/2002 | Bailey et al. |
| 2002/0044043 A1 | 4/2002 | Chaco et al. |
| 2002/0044059 A1 | 4/2002 | Reeder et al. |
| 2002/0082728 A1 | 6/2002 | Mueller et al. |
| 2002/0087115 A1 | 7/2002 | Hartlaub |
| 2002/0087116 A1 | 7/2002 | Hartlaub |

(56) References Cited

U.S. PATENT DOCUMENTS

| | | |
|---|---|---|
| 2002/0095486 A1 | 7/2002 | Bahl |
| 2002/0103675 A1 | 8/2002 | Vanelli |
| 2002/0123905 A1 | 9/2002 | Goodroe et al. |
| 2002/0143580 A1 | 10/2002 | Bristol et al. |
| 2002/0152239 A1 | 10/2002 | Bautista-Lloyd et al. |
| 2002/0154600 A1 | 10/2002 | Ido et al. |
| 2002/0173702 A1 | 11/2002 | Lebel et al. |
| 2002/0173875 A1 | 11/2002 | Wallace et al. |
| 2002/0193679 A1 | 12/2002 | Malave et al. |
| 2002/0194329 A1 | 12/2002 | Alling |
| 2003/0009244 A1 | 1/2003 | Engleson |
| 2003/0013959 A1 | 1/2003 | Grunwald et al. |
| 2003/0014222 A1 | 1/2003 | Klass et al. |
| 2003/0014817 A1 | 1/2003 | Gallant et al. |
| 2003/0025602 A1 | 2/2003 | Medema et al. |
| 2003/0028082 A1 | 2/2003 | Thompson |
| 2003/0036683 A1 | 2/2003 | Kehr et al. |
| 2003/0036744 A1 | 2/2003 | Struys et al. |
| 2003/0047126 A1 | 3/2003 | Tomaschko |
| 2003/0047600 A1 | 3/2003 | Nakanishi et al. |
| 2003/0050621 A1 | 3/2003 | Lebel et al. |
| 2003/0059750 A1 | 3/2003 | Bindler et al. |
| 2003/0060688 A1 | 3/2003 | Ciarniello et al. |
| 2003/0069963 A1 | 4/2003 | Jayant et al. |
| 2003/0079746 A1 | 5/2003 | Hickle |
| 2003/0097529 A1 | 5/2003 | Arimilli et al. |
| 2003/0104982 A1 | 6/2003 | Wittmann et al. |
| 2003/0105389 A1 | 6/2003 | Noonan et al. |
| 2003/0106553 A1 | 6/2003 | Vanderveen |
| 2003/0115358 A1 | 6/2003 | Yun |
| 2003/0120384 A1 | 6/2003 | Haitin et al. |
| 2003/0125662 A1 | 7/2003 | Bui |
| 2003/0130616 A1 | 7/2003 | Steil |
| 2003/0135087 A1 | 7/2003 | Hickle et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158749 A1 | 8/2003 | Olchanski et al. |
| 2003/0187338 A1 | 10/2003 | Say et al. |
| 2003/0200116 A1 | 10/2003 | Forrester |
| 2003/0204416 A1 | 10/2003 | Acharya |
| 2003/0204781 A1 | 10/2003 | Peebles et al. |
| 2003/0212364 A1 | 11/2003 | Mann et al. |
| 2003/0212379 A1 | 11/2003 | Bylund et al. |
| 2003/0212821 A1 | 11/2003 | Gillies et al. |
| 2003/0216831 A1 | 11/2003 | Hart et al. |
| 2003/0217962 A1 | 11/2003 | Childers et al. |
| 2004/0008123 A1 | 1/2004 | Carrender et al. |
| 2004/0010786 A1 | 1/2004 | Cool et al. |
| 2004/0015132 A1 | 1/2004 | Brown |
| 2004/0019464 A1 | 1/2004 | Martucci et al. |
| 2004/0019607 A1 | 1/2004 | Moubayed et al. |
| 2004/0030323 A1 | 2/2004 | Ullestad et al. |
| 2004/0039257 A1 | 2/2004 | Hickle |
| 2004/0057226 A1 | 3/2004 | Berthou et al. |
| 2004/0064341 A1 | 4/2004 | Langan et al. |
| 2004/0064342 A1 | 4/2004 | Browne et al. |
| 2004/0064435 A1 | 4/2004 | Moubayed et al. |
| 2004/0073161 A1 | 4/2004 | Tachibana |
| 2004/0073811 A1 | 4/2004 | Sanin |
| 2004/0077934 A1 | 4/2004 | Massad |
| 2004/0078231 A1 | 4/2004 | Wilkes et al. |
| 2004/0078236 A1 | 4/2004 | Stoodley et al. |
| 2004/0085186 A1 | 5/2004 | Eveland et al. |
| 2004/0104271 A1 | 6/2004 | Martucci et al. |
| 2004/0122530 A1 | 6/2004 | Hansen |
| 2004/0128162 A1 | 7/2004 | Schlotterbeck et al. |
| 2004/0128163 A1 | 7/2004 | Goodman et al. |
| 2004/0133441 A1 | 7/2004 | Brady et al. |
| 2004/0139004 A1 | 7/2004 | Cohen et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox, Jr. et al. |
| 2005/0086072 A1 | 4/2005 | Fox |
| 2005/0088704 A1 | 4/2005 | Vaschillo et al. |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102165 A1 | 5/2005 | Oshita et al. |
| 2005/0102167 A1 | 5/2005 | Kapoor |
| 2005/0102669 A1 | 5/2005 | Marney et al. |
| 2005/0107923 A1 | 5/2005 | Vanderveen |
| 2005/0108057 A1 | 5/2005 | Cohen et al. |
| 2005/0117529 A1 | 6/2005 | Ramos-Escano |
| 2005/0119788 A1 | 6/2005 | Engleson et al. |
| 2005/0119914 A1 | 6/2005 | Batch |
| 2005/0131739 A1 | 6/2005 | Rabinowitz et al. |
| 2005/0135306 A1 | 6/2005 | McAllen et al. |
| 2005/0137522 A1 | 6/2005 | Aoki |
| 2005/0137573 A1 | 6/2005 | Mclaughlin |
| 2005/0138428 A1 | 6/2005 | McAllen et al. |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox et al. |

(56) References Cited

U.S. PATENT DOCUMENTS

| | | |
|---|---|---|
| 2005/0261660 A1 | 11/2005 | Choi |
| 2005/0273059 A1 | 12/2005 | Mernoe et al. |
| 2005/0273367 A1 | 12/2005 | Nourie et al. |
| 2005/0277873 A1 | 12/2005 | Stewart et al. |
| 2005/0277890 A1 | 12/2005 | Stewart et al. |
| 2005/0277911 A1 | 12/2005 | Stewart et al. |
| 2005/0278194 A1 | 12/2005 | Holland et al. |
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0042139 A1 | 3/2006 | Mendes |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0074633 A1 | 4/2006 | Mahesh et al. |
| 2006/0074920 A1 | 4/2006 | Wefers et al. |
| 2006/0079831 A1 | 4/2006 | Gilbert |
| 2006/0089539 A1 | 4/2006 | Miodownik et al. |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122481 A1 | 6/2006 | Sievenpiper et al. |
| 2006/0122867 A1 | 6/2006 | Eggers et al. |
| 2006/0129140 A1 | 6/2006 | Todd et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0173715 A1 | 8/2006 | Wang et al. |
| 2006/0173927 A1 | 8/2006 | Beyer et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229918 A1 | 10/2006 | Fotsch et al. |
| 2006/0236373 A1 | 10/2006 | Graves et al. |
| 2006/0247606 A1 | 11/2006 | Batch |
| 2006/0253554 A1 | 11/2006 | Uwais |
| 2006/0258985 A1 | 11/2006 | Russell |
| 2006/0259327 A1 | 11/2006 | Hoag |
| 2006/0264895 A1 | 11/2006 | Flanders |
| 2006/0265246 A1 | 11/2006 | Hoag |
| 2006/0267753 A1 | 11/2006 | Hussey et al. |
| 2006/0268710 A1 | 11/2006 | Appanna et al. |
| 2006/0270971 A1 | 11/2006 | Gelfand et al. |
| 2006/0277206 A1 | 12/2006 | Bailey et al. |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0021715 A1 | 1/2007 | Kohlbrenner et al. |
| 2007/0027506 A1 | 2/2007 | Stender et al. |
| 2007/0060796 A1 | 3/2007 | Kim |
| 2007/0060870 A1 | 3/2007 | Tolle et al. |
| 2007/0060871 A1 | 3/2007 | Istoc |
| 2007/0061393 A1 | 3/2007 | Moore |
| 2007/0065363 A1 | 3/2007 | Dalal et al. |
| 2007/0073419 A1 | 3/2007 | Sesay |
| 2007/0073822 A1 | 3/2007 | Bennett et al. |
| 2007/0078314 A1 | 4/2007 | Grounsell |
| 2007/0083870 A1 | 4/2007 | Kanakogi |
| 2007/0088333 A1 | 4/2007 | Levin et al. |
| 2007/0093786 A1 | 4/2007 | Goldsmith et al. |
| 2007/0100665 A1 | 5/2007 | Brown |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |
| 2007/0135866 A1 | 6/2007 | Baker et al. |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213657 A1 | 9/2007 | Jennewine et al. |
| 2007/0213684 A1 | 9/2007 | Hickle et al. |
| 2007/0214003 A1 | 9/2007 | Holland et al. |
| 2007/0215545 A1 | 9/2007 | Bissler et al. |
| 2007/0229249 A1 | 10/2007 | McNeal et al. |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0233520 A1 | 10/2007 | Wehba et al. |
| 2007/0240215 A1 | 10/2007 | Flores |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299687 A1 | 12/2007 | Palmer et al. |
| 2007/0299695 A1 | 12/2007 | Jung et al. |
| 2008/0001771 A1 | 1/2008 | Faoro et al. |
| 2008/0004904 A1 | 1/2008 | Tran |
| 2008/0009684 A1 | 1/2008 | Corsetti et al. |
| 2008/0033361 A1 | 2/2008 | Evans et al. |
| 2008/0033966 A1 | 2/2008 | Wahl |
| 2008/0034323 A1 | 2/2008 | Blomquist |
| 2008/0041942 A1 | 2/2008 | Aissa |
| 2008/0052704 A1 | 2/2008 | Wysocki |
| 2008/0065007 A1 | 3/2008 | Peterson et al. |
| 2008/0065417 A1 | 3/2008 | Jung et al. |
| 2008/0071217 A1 | 3/2008 | Moubayed et al. |
| 2008/0071251 A1 | 3/2008 | Moubayed et al. |
| 2008/0086088 A1 | 4/2008 | Malcolm |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0097552 A1 | 4/2008 | Dicks et al. |
| 2008/0126969 A1 | 5/2008 | Blomquist |
| 2008/0139907 A1 | 6/2008 | Rao et al. |
| 2008/0148047 A1 | 6/2008 | Appenzeller et al. |
| 2008/0149117 A1 | 6/2008 | Raghuram |
| 2008/0154177 A1 | 6/2008 | Moubayed et al. |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0214919 A1 | 9/2008 | Harmon et al. |
| 2008/0246748 A1 | 10/2008 | Cassidy et al. |
| 2008/0256305 A1 | 10/2008 | Kwon |
| 2008/0259926 A1 | 10/2008 | Tavares et al. |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2008/0301298 A1 | 12/2008 | Bernardi et al. |
| 2008/0320387 A1 | 12/2008 | Sasaki et al. |
| 2008/0320466 A1 | 12/2008 | Dias |
| 2009/0003554 A1 | 1/2009 | Katis et al. |
| 2009/0005703 A1 | 1/2009 | Fasciano |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0036750 A1 | 2/2009 | Weinstein et al. |

(56) References Cited

U.S. PATENT DOCUMENTS

| | | |
|---|---|---|
| 2009/0051560 A1 | 2/2009 | Manning et al. |
| 2009/0054743 A1 | 2/2009 | Stewart |
| 2009/0054754 A1 | 2/2009 | McMahon et al. |
| 2009/0057399 A1 | 3/2009 | Sajkowsky |
| 2009/0063187 A1 | 3/2009 | Johnson et al. |
| 2009/0069785 A1 | 3/2009 | Miller et al. |
| 2009/0099867 A1 | 4/2009 | Newman |
| 2009/0135196 A1 | 5/2009 | Holland et al. |
| 2009/0143662 A1 | 6/2009 | Estes et al. |
| 2009/0149743 A1 | 6/2009 | Barron et al. |
| 2009/0150174 A1 | 6/2009 | Buck et al. |
| 2009/0150439 A1 | 6/2009 | Gejdos et al. |
| 2009/0150878 A1 | 6/2009 | Pathak et al. |
| 2009/0156991 A1 | 6/2009 | Roberts |
| 2009/0157695 A1 | 6/2009 | Roberts |
| 2009/0158274 A1 | 6/2009 | Roberts |
| 2009/0177146 A1 | 7/2009 | Nesbitt et al. |
| 2009/0177769 A1 | 7/2009 | Roberts |
| 2009/0177992 A1 | 7/2009 | Rubalcaba et al. |
| 2009/0183147 A1 | 7/2009 | Davis et al. |
| 2009/0209938 A1 | 8/2009 | Aalto-Setala |
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Blomquist et al. |
| 2009/0275896 A1 | 11/2009 | Kamen et al. |
| 2009/0284691 A1 | 11/2009 | Marhefka et al. |
| 2009/0292340 A1 | 11/2009 | Mass et al. |
| 2009/0306573 A1 | 12/2009 | Gagner et al. |
| 2009/0326340 A1 | 12/2009 | Wang |
| 2009/0326516 A1 | 12/2009 | Bangera et al. |
| 2010/0008377 A1 | 1/2010 | Hasti et al. |
| 2010/0022988 A1 | 1/2010 | Wochner |
| 2010/0036310 A1 | 2/2010 | Hillman |
| 2010/0056992 A1 | 3/2010 | Hayter |
| 2010/0083060 A1 | 4/2010 | Rahman |
| 2010/0095229 A1 | 4/2010 | Dixon et al. |
| 2010/0121170 A1 | 5/2010 | Rule |
| 2010/0121246 A1 | 5/2010 | Peters et al. |
| 2010/0121415 A1 | 5/2010 | Skelton et al. |
| 2010/0121654 A1 | 5/2010 | Portnoy et al. |
| 2010/0121752 A1 | 5/2010 | Banigan et al. |
| 2010/0130933 A1 | 5/2010 | Holland et al. |
| 2010/0131434 A1 | 5/2010 | Magent et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0174266 A1 | 7/2010 | Estes |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0209268 A1 | 8/2010 | Davis |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1 | 9/2010 | Bucknell |
| 2010/0271479 A1 | 10/2010 | Heydlauf |
| 2010/0273738 A1 | 10/2010 | Valcke et al. |
| 2010/0274218 A1 | 10/2010 | Yodfat et al. |
| 2010/0280486 A1 | 11/2010 | Khair et al. |
| 2010/0292634 A1 | 11/2010 | Kircher |
| 2010/0298765 A1 | 11/2010 | Budiman et al. |
| 2010/0318025 A1 | 12/2010 | John |
| 2011/0001605 A1 | 1/2011 | Kiani et al. |
| 2011/0021898 A1 | 1/2011 | Wei et al. |
| 2011/0028885 A1 | 2/2011 | Eggers et al. |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0072379 A1 | 3/2011 | Gannon |
| 2011/0078253 A1 | 3/2011 | Chan et al. |
| 2011/0078608 A1 | 3/2011 | Gannon et al. |
| 2011/0093284 A1 | 4/2011 | Dicks et al. |
| 2011/0099313 A1 | 4/2011 | Bolanowski |
| 2011/0106318 A1 | 5/2011 | Ledford et al. |
| 2011/0125095 A1 | 5/2011 | Lebel et al. |
| 2011/0138185 A1 | 6/2011 | Ju et al. |
| 2011/0166628 A1 | 7/2011 | Jain |
| 2011/0175728 A1 | 7/2011 | Baker, Jr. |
| 2011/0178462 A1 | 7/2011 | Moberg et al. |
| 2011/0185010 A1 | 7/2011 | Shatsky et al. |
| 2011/0196748 A1 | 8/2011 | Caron et al. |
| 2011/0231216 A1 | 9/2011 | Fyke et al. |
| 2011/0252230 A1 | 10/2011 | Segre et al. |
| 2011/0257496 A1 | 10/2011 | Terashima et al. |
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289162 A1 | 11/2011 | Furlong |
| 2011/0289314 A1 | 11/2011 | Whitcomb |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0005680 A1 | 1/2012 | Dolby et al. |
| 2012/0011253 A1 | 1/2012 | Friedman et al. |
| 2012/0016305 A1 | 1/2012 | Jollota |
| 2012/0029941 A1 | 2/2012 | Malave et al. |
| 2012/0036102 A1 | 2/2012 | Fletcher et al. |
| 2012/0036550 A1 | 2/2012 | Rodriguez |
| 2012/0066501 A1 | 3/2012 | Xiong |
| 2012/0070045 A1 | 3/2012 | Vesper et al. |
| 2012/0079084 A1 | 3/2012 | Forssell et al. |
| 2012/0095437 A1 | 4/2012 | Hemmerling |
| 2012/0112903 A1 | 5/2012 | Kaib et al. |
| 2012/0130198 A1 | 5/2012 | Beaule |
| 2012/0143116 A1 | 6/2012 | Ware et al. |
| 2012/0150556 A1 | 6/2012 | Galasso et al. |
| 2012/0157920 A1 | 6/2012 | Flachbart et al. |
| 2012/0179135 A1 | 7/2012 | Rinehart et al. |
| 2012/0179136 A1 | 7/2012 | Rinehart et al. |
| 2012/0185267 A1 | 7/2012 | Kamen et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0260012 A1 | 10/2012 | Gao-Saari et al. |
| 2012/0277716 A1 | 11/2012 | Ali et al. |
| 2012/0283630 A1 | 11/2012 | Lee et al. |
| 2012/0284734 A1 | 11/2012 | McQuaid et al. |
| 2012/0323212 A1 | 12/2012 | Murphy |
| 2012/0330380 A1 | 12/2012 | Corndorf |
| 2013/0006666 A1 | 1/2013 | Schneider |
| 2013/0006702 A1 | 1/2013 | Wu |
| 2013/0012877 A1 | 1/2013 | Debelser et al. |
| 2013/0012879 A1 | 1/2013 | Debelser et al. |
| 2013/0012880 A1 | 1/2013 | Blomquist |
| 2013/0015980 A1 | 1/2013 | Evans et al. |
| 2013/0036403 A1 | 2/2013 | Geist |
| 2013/0036412 A1 | 2/2013 | Birtwhistle et al. |
| 2013/0066265 A1 | 3/2013 | Grant |
| 2013/0072872 A1 | 3/2013 | Yodfat et al. |
| 2013/0091350 A1 | 4/2013 | Gluck |
| 2013/0096444 A1 | 4/2013 | Condurso et al. |
| 2013/0096648 A1 | 4/2013 | Benson |
| 2013/0102963 A1 | 4/2013 | Marsh et al. |
| 2013/0114594 A1 | 5/2013 | Van Zijst |
| 2013/0116578 A1 | 5/2013 | An |
| 2013/0133083 A1 | 5/2013 | Kurumai |
| 2013/0138452 A1 | 5/2013 | Cork et al. |
| 2013/0144206 A1 | 6/2013 | Lee et al. |
| 2013/0150824 A1 | 6/2013 | Estes et al. |

(56) References Cited

U.S. PATENT DOCUMENTS

| | | |
|---|---|---|
| 2013/0158504 A1 | 6/2013 | Ruchti et al. |
| 2013/0167245 A1 | 6/2013 | Birtwhistle et al. |
| 2013/0173473 A1 | 7/2013 | Birtwhistle et al. |
| 2013/0191770 A1 | 7/2013 | Bartz et al. |
| 2013/0204188 A1 | 8/2013 | Kamen et al. |
| 2013/0218080 A1 | 8/2013 | Peterfreund et al. |
| 2013/0261993 A1 | 10/2013 | Ruchti et al. |
| 2013/0274669 A1 | 10/2013 | Stempfle et al. |
| 2013/0275539 A1 | 10/2013 | Gross et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0317753 A1 | 11/2013 | Kamen et al. |
| 2013/0346108 A1 | 12/2013 | Kamen et al. |
| 2014/0025392 A1 | 1/2014 | Chandrasenan |
| 2014/0039446 A1 | 2/2014 | Day |
| 2014/0108783 A1 | 4/2014 | Suzuki |
| 2014/0142540 A1 | 5/2014 | Imhof |
| 2014/0142963 A1 | 5/2014 | Hill et al. |
| 2014/0163517 A1 | 6/2014 | Finan et al. |
| 2014/0172994 A1 | 6/2014 | Raumann et al. |
| 2014/0180711 A1 | 6/2014 | Kamen et al. |
| 2014/0197950 A1 | 7/2014 | Shupp et al. |
| 2014/0215490 A1 | 7/2014 | Mathur et al. |
| 2014/0257251 A1 | 9/2014 | Bush et al. |
| 2014/0266790 A1 | 9/2014 | Al-Ali et al. |
| 2014/0266794 A1 | 9/2014 | Brown et al. |
| 2014/0269643 A1 | 9/2014 | Sun |
| 2014/0276571 A1 | 9/2014 | Ludolph |
| 2014/0280522 A1 | 9/2014 | Watte |
| 2014/0294177 A1 | 10/2014 | Shastry et al. |
| 2014/0297329 A1 | 10/2014 | Rock |
| 2014/0316819 A1 | 10/2014 | Dunsirn et al. |
| 2014/0318639 A1 | 10/2014 | Peret et al. |
| 2014/0350513 A1 | 11/2014 | Oruklu et al. |
| 2014/0358077 A1 | 12/2014 | Oruklu et al. |
| 2014/0366878 A1 | 12/2014 | Baron |
| 2014/0371543 A1 | 12/2014 | Steinhauer et al. |
| 2015/0005935 A1 | 1/2015 | Bae et al. |
| 2015/0006907 A1 | 1/2015 | Brouwer et al. |
| 2015/0045729 A1 | 2/2015 | Denzer et al. |
| 2015/0058044 A1 | 2/2015 | Butler et al. |
| 2015/0058960 A1 | 2/2015 | Schmoyer et al. |
| 2015/0066531 A1 | 3/2015 | Jacobson et al. |
| 2015/0081894 A1 | 3/2015 | Blomquist |
| 2015/0100038 A1 | 4/2015 | McCann et al. |
| 2015/0100787 A1 | 4/2015 | Westin et al. |
| 2015/0117234 A1 | 4/2015 | Raman et al. |
| 2015/0134265 A1 | 5/2015 | Kohlbrecher et al. |
| 2015/0141955 A1 | 5/2015 | Ruchti et al. |
| 2015/0151051 A1 | 6/2015 | Tsoukalis |
| 2015/0161354 A1 | 6/2015 | Blomquist |
| 2015/0199192 A1 | 7/2015 | Borges et al. |
| 2015/0199485 A1 | 7/2015 | Borges et al. |
| 2015/0207626 A1 | 7/2015 | Neftel et al. |
| 2015/0220890 A1 | 8/2015 | Seshadri et al. |
| 2015/0230760 A1 | 8/2015 | Schneider |
| 2015/0281128 A1 | 10/2015 | Sindhu |
| 2015/0325064 A1 | 11/2015 | Downey |
| 2015/0328396 A1 | 11/2015 | Adams et al. |
| 2015/0352301 A1 | 12/2015 | Stedman et al. |
| 2015/0371004 A1 | 12/2015 | Jones |
| 2015/0379237 A1 | 12/2015 | Mills et al. |
| 2016/0001003 A1 | 1/2016 | Perazzo et al. |
| 2016/0006695 A1 | 1/2016 | Prodoehl et al. |
| 2016/0015885 A1 | 1/2016 | Pananen et al. |
| 2016/0034655 A1 | 2/2016 | Gray et al. |
| 2016/0045661 A1 | 2/2016 | Gray et al. |
| 2016/0051749 A1 | 2/2016 | Istoc |
| 2016/0051751 A1 | 2/2016 | Silkaitis et al. |
| 2016/0063471 A1 | 3/2016 | Kobres et al. |
| 2016/0103960 A1 | 4/2016 | Hume et al. |
| 2016/0158437 A1 | 6/2016 | Biasi et al. |
| 2016/0228633 A1 | 8/2016 | Welsch et al. |
| 2016/0241391 A1 | 8/2016 | Fenster |
| 2016/0277152 A1 | 9/2016 | Xiang et al. |
| 2016/0285876 A1 | 9/2016 | Perez et al. |
| 2016/0317742 A1 | 11/2016 | Gannon et al. |
| 2016/0350513 A1 | 12/2016 | Jacobson et al. |
| 2016/0378618 A1 | 12/2016 | Cmielowski |
| 2017/0024534 A1 | 1/2017 | Arrizza et al. |
| 2017/0034277 A1 | 2/2017 | Jackson et al. |
| 2017/0063559 A1 | 3/2017 | Wallrabenstein |
| 2017/0099148 A1 | 4/2017 | Ochmanski et al. |
| 2017/0104645 A1 | 4/2017 | Wooton et al. |
| 2017/0111301 A1 | 4/2017 | Robinson |
| 2017/0140134 A1 | 5/2017 | Brough et al. |
| 2017/0146381 A1 | 5/2017 | Eckel et al. |
| 2017/0149567 A1 | 5/2017 | Moskal |
| 2017/0149929 A1 | 5/2017 | Moskal |
| 2017/0214762 A1 | 7/2017 | Swain et al. |
| 2017/0246388 A1 | 8/2017 | Kohlbrecher |
| 2017/0258401 A1 | 9/2017 | Volpe |
| 2017/0258986 A1 | 9/2017 | Tsoiukalis |
| 2017/0262590 A1 | 9/2017 | Karakosta et al. |
| 2017/0274140 A1 | 9/2017 | Howard et al. |
| 2017/0286637 A1 | 10/2017 | Arrizza et al. |
| 2017/0319780 A1 | 11/2017 | Belkin et al. |
| 2017/0325091 A1 | 11/2017 | Freeman et al. |
| 2017/0331804 A1 | 11/2017 | Jellison et al. |
| 2017/0351841 A1 | 12/2017 | Moskal |
| 2018/0008772 A1 | 1/2018 | Wehba et al. |
| 2018/0028742 A1 | 2/2018 | Day et al. |
| 2018/0043094 A1 | 2/2018 | Day et al. |
| 2018/0063724 A1 | 3/2018 | Zhang et al. |
| 2018/0121613 A1 | 5/2018 | Connely, IV et al. |
| 2018/0122502 A1 | 5/2018 | Jones et al. |
| 2018/0126067 A1 | 5/2018 | Ledford et al. |
| 2018/0157821 A1 | 6/2018 | Fan |
| 2018/0181712 A1 | 6/2018 | Ensey et al. |
| 2018/0247712 A1 | 8/2018 | Muhsin et al. |
| 2018/0272117 A1 | 9/2018 | Fangrow |
| 2018/0278594 A1 | 9/2018 | Schiffman et al. |
| 2018/0317826 A1 | 11/2018 | Muhsin et al. |
| 2018/0322948 A1 | 11/2018 | Drost et al. |
| 2018/0359085 A1 | 12/2018 | Dervyn |
| 2019/0006044 A1 | 1/2019 | Brask |
| 2019/0030329 A1 | 1/2019 | Hannaman et al. |
| 2019/0036688 A1 | 1/2019 | Wasily et al. |
| 2019/0096518 A1 | 3/2019 | Pace |
| 2019/0132196 A1 | 5/2019 | Trivedi et al. |
| 2019/0147998 A1 | 5/2019 | Ruchti et al. |
| 2019/0166501 A1 | 5/2019 | Debates et al. |
| 2019/0172590 A1 | 6/2019 | Vesto et al. |
| 2019/0207965 A1 | 7/2019 | Espinosa |
| 2019/0228863 A1 | 7/2019 | Dharwad et al. |
| 2019/0229982 A1 | 7/2019 | Ikuta et al. |
| 2019/0240405 A1 | 8/2019 | Wehba et al. |
| 2019/0243829 A1 | 8/2019 | Butler et al. |
| 2019/0244689 A1 | 8/2019 | Atkin |
| 2019/0245942 A1 | 8/2019 | Moskal |
| 2019/0269852 A1 | 9/2019 | Kohlbrecher |
| 2019/0311803 A1 | 10/2019 | Kohlbrecher et al. |
| 2019/0348160 A1 | 11/2019 | Heavelyn et al. |
| 2019/0392929 A1 | 12/2019 | Gassman |
| 2020/0023127 A1 | 1/2020 | Simpson et al. |
| 2020/0027541 A1 | 1/2020 | Xavier et al. |
| 2020/0027548 A1 | 1/2020 | Xavier et al. |
| 2020/0027550 A1 | 1/2020 | Xavier et al. |
| 2020/0027551 A1 | 1/2020 | Xavier et al. |
| 2020/0035355 A1 | 1/2020 | Xavier et al. |
| 2020/0054825 A1 | 2/2020 | Kamen et al. |
| 2020/0118692 A1 | 4/2020 | Booker et al. |
| 2020/0153627 A1 | 5/2020 | Wentz |
| 2020/0206413 A1 | 7/2020 | Silkaitis et al. |
| 2020/0220865 A1 | 7/2020 | Finger et al. |
| 2020/0282139 A1 | 9/2020 | Susi |
| 2020/0334497 A1 | 10/2020 | Barrett et al. |
| 2020/0335194 A1 | 10/2020 | Jacobson et al. |
| 2020/0351376 A1 | 11/2020 | Moskal |
| 2020/0353167 A1 | 11/2020 | Vivek et al. |
| 2020/0353168 A1 | 11/2020 | Keenan et al. |
| 2021/0014259 A1 | 1/2021 | Harris et al. |
| 2021/0043296 A1 | 2/2021 | Xavier et al. |

(56) References Cited

U.S. PATENT DOCUMENTS

| | | |
|---|---|---|
| 2021/0045640 A1 | 2/2021 | Poltorak |
| 2021/0085855 A1 | 3/2021 | Belkin et al. |
| 2021/0098106 A1 | 4/2021 | Kohlbrecher et al. |
| 2021/0098107 A1 | 4/2021 | Xavier et al. |
| 2021/0252210 A1 | 8/2021 | Day et al. |
| 2021/0358603 A1 | 11/2021 | Xavier et al. |
| 2021/0375421 A1 | 12/2021 | Ruchti et al. |
| 2021/0375438 A1 | 12/2021 | Xavier et al. |
| 2021/0409362 A1 | 12/2021 | Katis et al. |
| 2022/0023535 A1 | 1/2022 | Day |
| 2022/0037011 A1 | 2/2022 | Fryman |
| 2022/0037012 A1 | 2/2022 | Fryman |
| 2022/0051777 A1 | 2/2022 | Xavier et al. |
| 2022/0062541 A1 | 3/2022 | Kamen et al. |
| 2022/0129452 A1 | 4/2022 | Butler et al. |
| 2022/0139536 A1 | 5/2022 | Xavier et al. |
| 2022/0139537 A1 | 5/2022 | Xavier et al. |
| 2022/0139538 A1 | 5/2022 | Xavier et al. |
| 2022/0150307 A1 | 5/2022 | Walsh et al. |
| 2022/0165404 A1 | 5/2022 | Vivek et al. |
| 2022/0189605 A1 | 6/2022 | Kelly et al. |
| 2022/0223283 A1 | 7/2022 | Biasi et al. |
| 2022/0270736 A1 | 8/2022 | Kohlbrecher |
| 2022/0328175 A1 | 10/2022 | Arrizza et al. |
| 2022/0331513 A1 | 10/2022 | Howard et al. |
| 2022/0344023 A1 | 10/2022 | Xavier et al. |
| 2022/0375565 A1 | 11/2022 | Xavier et al. |
| 2022/0384059 A1 | 12/2022 | Xavier et al. |
| 2023/0009405 A1 | 1/2023 | Xavier et al. |
| 2023/0009417 A1 | 1/2023 | Xavier et al. |
| 2023/0139360 A1 | 5/2023 | Kohlbrecher et al. |
| 2023/0145267 A1 | 5/2023 | Xavier et al. |
| 2023/0147762 A1 | 5/2023 | Xavier et al. |
| 2023/0166026 A1 | 6/2023 | Jacobson et al. |
| 2023/0253108 A1 | 8/2023 | Dharwad et al. |
| 2023/0285660 A1 | 9/2023 | Day et al. |
| 2023/0298768 A1 | 9/2023 | Jacobson et al. |
| 2023/0320935 A1 | 10/2023 | Tagliamento |
| 2023/0321350 A1 | 10/2023 | Day et al. |
| 2023/0321351 A1 | 10/2023 | Wehba et al. |
| 2023/0326570 A1 | 10/2023 | Kohlbrecher |
| 2023/0410989 A1 | 12/2023 | Xavier et al. |
| 2024/0038358 A1 | 2/2024 | Xavier et al. |
| 2024/0047035 A1 | 2/2024 | Ruchti et al. |
| 2024/0071609 A1 | 2/2024 | Rohlwing |

FOREIGN PATENT DOCUMENTS

| | | |
|---|---|---|
| CA | 2 060 151 | 8/1997 |
| CA | 2 125 300 | 10/1999 |
| CA | 2 630 102 | 10/2008 |
| CA | 2 687 587 | 12/2008 |
| CA | 2 897 897 | 7/2014 |
| CA | 2 898 825 | 7/2014 |
| CA | 2 900 564 | 10/2014 |
| CA | 2 606 968 | 1/2020 |
| CN | 1759398 | 4/2006 |
| CN | 102521474 | 6/2012 |
| CN | 103816582 | 5/2014 |
| CN | 103920206 | 7/2014 |
| CN | 102300501 | 4/2015 |
| CN | 104487976 | 4/2015 |
| CN | 107810536 | 1/2023 |
| CO | 01110843 | 8/2003 |
| DE | 31 12 762 | 1/1983 |
| DE | 34 35 647 | 7/1985 |
| DE | 198 44 252 | 3/2000 |
| DE | 199 32 147 | 1/2001 |
| DE | 103 52 456 | 7/2005 |
| EP | 0 319 267 | 6/1989 |
| EP | 0 380 061 | 8/1990 |
| EP | 0 384 155 | 8/1990 |
| EP | 0 460 533 | 12/1991 |
| EP | 0 564 127 | 6/1993 |
| EP | 0 633 035 | 1/1995 |
| EP | 0 652 528 | 5/1995 |
| EP | 0 672 427 | 9/1995 |
| EP | 0 683 465 | 11/1995 |
| EP | 0 880 936 | 12/1998 |
| EP | 1 050 993 | 11/2000 |
| EP | 1 157 711 | 11/2001 |
| EP | 1 174 817 | 1/2002 |
| EP | 0 664 102 | 4/2002 |
| EP | 1 197 178 | 4/2002 |
| EP | 0 830 775 | 8/2002 |
| EP | 1 500 025 | 4/2003 |
| EP | 1 487 171 | 7/2007 |
| EP | 1 933 497 | 6/2008 |
| EP | 2 026 223 | 2/2009 |
| EP | 2 113 842 | 11/2009 |
| EP | 2 228 004 | 9/2010 |
| EP | 2 243 506 | 10/2010 |
| EP | 2 410 448 | 1/2012 |
| EP | 2 742 961 | 6/2014 |
| EP | 2 874 087 | 5/2015 |
| ES | 2 371 995 | 1/2012 |
| FR | 2 717 919 | 9/1995 |
| GB | 2 285 135 | 6/1995 |
| JP | 04-161139 | 6/1992 |
| JP | 07-502678 | 3/1995 |
| JP | 11-500643 | 1/1999 |
| JP | 2000-316820 | 11/2000 |
| JP | 2002-531154 | 9/2002 |
| JP | 2003-016183 | 1/2003 |
| JP | 2003-296173 | 10/2003 |
| JP | 2003-308586 | 10/2003 |
| JP | 2005-021463 | 1/2005 |
| JP | 2005-527284 | 9/2005 |
| JP | 2005-284846 | 10/2005 |
| JP | 2006-047319 | 2/2006 |
| JP | 2006-520949 | 9/2006 |
| JP | 2007-518479 | 7/2007 |
| JP | 2007-525256 | 9/2007 |
| JP | 2008-080036 | 4/2008 |
| JP | 2008-516303 | 5/2008 |
| JP | 2008-158622 | 7/2008 |
| JP | 2008-529675 | 8/2008 |
| JP | 2009-163534 | 7/2009 |
| JP | 2010-502361 | 1/2010 |
| JP | 2011-506048 | 3/2011 |
| JP | 2012-011204 | 1/2012 |
| JP | 2012-070991 | 4/2012 |
| JP | 2012-523895 | 10/2012 |
| JP | 2014-068283 | 4/2014 |
| JP | 5647644 | 1/2015 |
| TW | 200426656 | 12/2004 |
| TW | 1631966 | 8/2018 |
| WO | WO 84/001719 | 5/1984 |
| WO | WO 91/016416 | 10/1991 |
| WO | WO 92/010985 | 7/1992 |
| WO | WO 92/013322 | 8/1992 |
| WO | WO 94/005355 | 3/1994 |
| WO | WO 96/008755 | 3/1996 |
| WO | WO 96/025186 | 8/1996 |
| WO | WO 96/025963 | 8/1996 |
| WO | WO 98/012670 | 3/1998 |
| WO | WO 98/019263 | 5/1998 |
| WO | WO 99/051003 | 10/1999 |
| WO | WO 00/013580 | 3/2000 |
| WO | WO 00/053243 | 9/2000 |
| WO | WO 01/014974 | 3/2001 |
| WO | WO 01/033484 | 5/2001 |
| WO | WO 01/045014 | 6/2001 |
| WO | WO 01/083007 | 11/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/023551 | 3/2003 |
| WO | WO 03/050917 | 6/2003 |

(56) References Cited

FOREIGN PATENT DOCUMENTS

| | | |
|---|---|---|
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/050526 | 6/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/059495 | 5/2008 |
| WO | WO 2008/064254 | 5/2008 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/045506 | 4/2013 |
| WO | WO 2014/100736 | 6/2014 |
| WO | WO 2014/131729 | 9/2014 |
| WO | WO 2014/131730 | 9/2014 |
| WO | WO 2015/047595 | 4/2015 |
| WO | WO 2015/124569 | 8/2015 |
| WO | WO 2016/179389 | 11/2016 |
| WO | WO 2017/176928 | 10/2017 |
| WO | WO 2017/200989 | 11/2017 |
| WO | WO 2019/219290 | 11/2019 |
| WO | WO 00/003344 | 1/2020 |
| WO | WO 2020/227403 | 11/2020 |
| WO | WO 2021/201884 | 10/2021 |
| WO | WO 2022/006014 | 1/2022 |
| WO | WO 2022/051230 | 3/2022 |
| WO | WO 2023/159134 | 8/2023 |

OTHER PUBLICATIONS

Ahn et al., "Towards Scalable Authentication in Health Services", Eleventh IEEE International Workshops on Enabling Technologies: Infrastructure for Collaborative Enterprises, Jun. 2002, pp. 83-88.
Akridge, Jeannie, "New Pumps Outsmart User Error", Healthcare Purchasing News, Apr. 2011, pp. 10, <http://web.archive.org/web/20110426122450/http://www.hpnonline.com/inside/2011-04/1104-OR-Pumps.html>.
Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.
Beard et al., "Total Quality Pain Management: History, Background, Resources", Abbott Laboratories, TQPM Survey History, available Feb. 2015 or earlier, pp. 1-3.
Bektas et al., "Bluetooth Communication Employing Antenna Diversity", Proceedings of Eight IEEE International Symposium on Computers and Communication, Jul. 2003, pp. 6.
Bellare et al., "Security Proofs for Identity-Based Identification and Signature Schemes", Lecture Notes in Computer Science, Jan. 2009, vol. 22, No. 1, pp. 18.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Block, Alexander, "Secret Sharing and 1-11 Threshold Signatures with BLS", Jul. 2, 2018, https://blog.dash.org/secret-sharing-and-threshold-signatures-with-bls-954d1587b5f, in 8 pages.
Braun, "Infusomat® Space and Accessories", Instructions for Use, Nov. 2010, pp. 68. <http://corp.bbraun.ee/Extranet/Infusionipumbad/Kasutusjuhendid/Vanad/Kasutusjuhend-Infusomat_Space(vers688J,inglise_k).pdf>.
Brownlee, Seth, "Product Spotlight: The Plum A+ with Hospira MedNet Infusion System", PP&P Magazine, Dec. 2005, vol. 2, No. 7, pp. 2.
Cannon, MD et al., "Automated Heparin-Delivery System to Control Activated Partial Thromboplastin Time", Circulation, Feb. 16, 1999, vol. 99, pp. 751-756.
Cardinal Health, "Alaris® Syringe Pumps" Technical Service Manual, Copyright 2002-2006, Issue 9, pp. 1-88, <http://www.frankshospitalworkshop.com/equipment/documents/infusion_pumps/service_manuals/Cardinal_Alaris_-_Service_Manual.pdf>.
"CareAware® Infusion Management", Cerner Store, as printed May 12, 2011, pp. 3, <https://store.cerner.com/items/7>.
Chen et al., "Enabling Location-Based Services on Wireless LANs", The 11th IEEE International Conference on Networks, ICON 2003, Sep. 28-Oct. 1, 2003, pp. 567-572.
"Computer Dictionary", Microsoft Press, Third Edition, Microsoft Press, 1997, pp. 430 & 506.
"Context-Free Grammar", Wikipedia.org, as last modified Mar. 5, 2010 in 11 pages, <https://en.wikipedia.org/w/index.php/?title=Context-free_grammar&oldid=347915989>.
Crawford, Anne J., MSN, RNC, "Building a Successful Quality Pain Service: Using Patient Satisfaction Data and the Clinical Practice Guideline", USA, 1995, pp. 1-6.
Crocker et al., "Augmented BNF for Syntax Specifications: ABNF", Network Working Group, Standards Track, Jan. 2008, pp. 16.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
Davies, T., "Cordless Data Acquisition in a Hospital Environment", IEE Colloquium on Cordless Computing—Systems and User Experience, 1993, pp. 4.
Dayhoff et al., "Medical Data Capture and Display: The Importance of Clinicians' Workstation Design", AMIA, Inc., 1994, pp. 541-545.

(56) References Cited

OTHER PUBLICATIONS

Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.

Doesburg et al., "Improved Usability of a Multi-Infusion Setup Using a Centralized Control Interface: A Task-Based Usability Test", Aug. 11, 2017, PLoS ONE, vol. 12, No. 8, pp. 10.

"Download", Free On-Line Dictionary of Computing, as archived Jun. 16, 2010 in 1 page, http://web.archive.org/web/20100616010314/https://foldoc.org/download.

East PhD et al., "Digital Electronic Communication Between ICU Ventilators and Computers and Printers", Respiratory Care, Sep. 1992, vol. 37, No. 9, pp. 1113-1122.

Edworthy, Judy, "Medical Audible Alarms: A Review", Journal of the American Medical Informatics Association, vol. 20, No. 3, 2013, pp. 584-589.

Einhorn, George W., "Total Quality Pain Management: A Computerized Quality Assessment Tool for Postoperative Pain Management", Abbott Laboratories, Chicago, IL, Mar. 2, 2000, pp. 1-4.

Eskew et al., "Using Innovative Technologies to Set New Safety Standards for the Infusion of Intravenous Medications", Hospital Pharmacy, 2002, vol. 37, No. 11, pp. 1179-1189.

Felleiter et al., "Data Processing in Prehospital Emergency Medicine", International journal of Clinical Monitoring and Computing, Feb. 1995, vol. 12, No. 1, pp. 37-41.

"File Verification", Wikipedia.org, as last modified Oct. 11, 2011 in 2 pages, <https://en.wikipedia.org/w/index.php?title=File_verification&oldid=455048290>.

Fogt et al., Development and Evaluation of a Glucose Analyzer for a Glucose-Controlled Insulin Infusion System (Biostator®), Clinical Chemistry, 1978, vol. 24, No. 8, pp. 1366-1372.

Gabel et al., "Camp: A Common API for Measuring Performance", 21st Large Installations System Administration Conference (LISA '07), 2007, pp. 49-61.

Gage et al., "Automated Anesthesia Surgery Medical Record System", International Journal of Clinical Monitoring and Computing, Dec. 1990, vol. 7, No. 4, pp. 259-263.

Galt et al., "Personal Digital Assistant-Based Drug Information Sources: Potential to Improve Medication Safety", Journal of Medical Library Association, Apr. 2005, vol. 93, No. 2, pp. 229-236.

Gardner, Ph.D et al., "Real Time Data Acquisition: Recommendations for the Medical Information Bus (MIB)", 1992, pp. 813-817.

"General-Purpose Infusion Pumps", Health Devices, EXRI Institute, Oct. 1, 2002, vol. 31, No. 10, pp. 353-387.

Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.

Glaeser, "A Hierarchical Minicomputer System for Continuous Post-Surgical Monitoring", Computers and Biomedical Research, Aug. 31, 1975, pp. 336-361.

Goldberg et al., "Clinical Results of an Updated Insulin Infusion Protocol in Critically Ill Patients", Diabetes Spectrum, 2005, vol. 18, No. 3, pp. 188-191.

Gomez et al., "CLAM: Connection-Less, Lightweight, and Multiway Communication Support for Distributed Computing", Computer Science, 1997, vol. 1199, pp. 227-240.

"GPS Tracker for Medical Equipment", <http://www.trackingsystem.com/forbusinesses/corporate-trackingsystem/1098-gps-tracker-formedicalequipment.html>, Mar. 15, 2015, pp. 2.

Graseby, "Model 3000/500 and Micro 3100/505: Volumetric Infusion Pump", Technical Service Manual, Graseby Medical Ltd., Apr. 2002, Issue A, pp. 160.

Graseby, "Model 3000/500 and Micro 3100/505: Volumetric Infusion Pump: Illustrated Parts List for Pump Serial Nos. from 3000 to 59,999", Technical Service Manual, Graseby Medical Ltd., Apr. 2002, Issue A, pp. 71.

Gutwin et al., "Gone But Not Forgotten: Designing for Disconnection in Synchronous Groupware", CSCW 2010, Feb. 6-10, 2010, Savannah, Georgia, USA., pp. 179-188.

Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.

Hamann et al., "PUMPSIM: A Software Package for Simulating Computer-Controlled Drug Infusion Pumps", Annual International Conference of the IEEE Engineering in Medicine and Biology Society, 1990, vol. 12, No. 5, pp. 2019-2020.

Hasegawa et al., "On a Portable Memory Device for Physical Activities and Informations of Maternal Perception", Journal of Perinatal Medicine, 1988, vol. 16, No. 4, pp. 349-356.

Hawley et al., "Clinical Implementation of an Automated Medical Information Bus in an Intensive Care Unit", Proceedings of the Annual Symposium on Computer Application in Medical Care, Nov. 9, 1988, pp. 621-624.

Hayes-Roth et al., "Guardian: A Prototype Intelligent Agent for Intensive-Care Monitoring", Artificial Intelligence in Medicine, vol. 4, Dec. 31, 1992, pp. 165-185.

Hospira, GemStar® Pain Management Infusion System 9-084-PR1-2-2, <www.hospira.com/products/gemstar_painmanagement.aspx>, Jan. 28, 2010, pp. 1-2.

Huang et al., "Secure Identity-Based Data Sharing and Profile Matching for Mobile Healthcare Social Networks in Cloud Computing", vol. 6, Jul. 2018, pp. 36584-36594.

Introducing Abbott TQPM (Total Quality Pain Management), Abbott Laboratories, Abbott Park, IL, May 2000, pp. 1-4.

"Infusion Pump", Wikipedia.org, as last modified Mar. 27, 2014, in 3 pages, <https://web.archive.org/web/20140703024932/https://en.wikipedia.org/wiki/Infusion_pump>.

Isaka et al., "Control Strategies for Arterial Blood Pressure Regulation", IEEE Transactions on Biomedical Engineering, Apr. 1993, vol. 40, No. 4, pp. 353-363.

Johnson et al., "Using BCMA Software to Improve Patient Safety in Veterans Administration Medical Centers", Journal of Healthcare Information Management, Dec. 6, 2004, vol. 16, No. 1, pp. 46-51.

Kent Displays, "Reflex™ Electronic Skins", Product Brief 25127B, 2009, pp. 2.

Kent Displays, "Reflex Electronic Skins Engineering Evaluation Kit", 25136A, Mar. 10, 2009.

Lefkowitz et al., "A Trial of the Use of Bar Code Technology to Restructure a Drug Distribution and Administration System", Hospital Pharmacy, Mar. 31, 1991, vol. 26, No. 3, pp. 239-242.

Lenssen et al., "Bright Color Electronic Paper Technology and Applications", IDS '09 Publication EP1-2 (Phillips Research), 2009, pp. 529-532.

Leveson, Nancy, "Medical Devices: The Therac-25", Appendix A, University of Washington, 1995, pp. 49.

Li et al., "Hijacking an Insulin Pump: Security Attacks and Defenses for a Diabetes Therapy System", 2011 IEEE 13th International Conference on e-Health Networking, Applications and Services, 2011, pp. 150-156.

Linkens, D.A. "Computer Control for Patient Care", Computer Control of Real-Time Processes, IEE Control Engineering Series 41, 1990, Ch. 13, pp. 216-238.

Mako Hill et al., "The Official Ubuntu Book", Shoeisha Co., Ltd., 1st Edition, Jun. 11, 2007, pp. 115 to 125.

Marshall, et al., "New Microprocessor-Based Insulin Controller", IEEE Transactions on Biomedical Engineering, Nov. 1983, vol. BME-30, No. 11, pp. 689-695.

Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.

Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.

Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.

(56) References Cited

OTHER PUBLICATIONS

"McKesson Automation and ALARIS Medical Systems Developing Point-of-Care Bar Coding Solution to Improve IV Medication Safety", PR Newswire, NY, Dec. 9, 2002, pp. 4.

Medfusion™, "Medfusion Syringe Infusion Pump Model 4000", Operator's Manual, Software Version V1.1, Sep. 2011, pp. 154. <http://www.medfusionpump.com/assets/literature/manuals/Operators_Manual_4000_40-5760-51A.pdf>.

Metnitz et al., "Computer Assisted Data Analysis in Intensive Care: the ICDEV Project-Development of aScientific Database System for Intensive Care", International Journal of Clinical Monitoring and Computing, Aug. 1995, vol. 12, No. 3, pp. 147-159.

Michienzi, Kelly, "Managing Drug Library Updates", Pharmacy Purchasing Products, https://www.pppmag.com/article/1061, Feb. 2012, vol. 9, pp. 22-23.

Micrel Medical Devices, "MP Daily +" <http://web.archive.org/web/20130803235715/http://www.micrelmed.com/index.aspx?productid=9> as archived Aug. 3, 2013 in 1 page.

Moghissi, Etie, MD, FACP, FACE, "Hyperglycemia in Hospitalized Patients", A Supplement to ACP Hospitalist, Jun. 15, 2008, pp. 32.

Murphy, Robert, "The Design of Safety-Critical Medical Infusion Devices", May 30, 2007, Doctor of Philosophy submission, pp. 317.

Murray, Jr. et al., "Automated Drug Identification System (during surgery)", IEEE Proceedings of Southeastcon '91, Apr. 7-10, 1991, pp. 265.

Nicholson et al., "Smart' Infusion Apparatus for Computation and Automated Delivery of Loading, Tapering, and Maintenance Infusion Regimens of Lidocaine, Procainamide, and Theophylline", Proceedings of the Seventh Annual Symposium on Computer Applications in Medical Care, Oct. 1983, pp. 212-213.

Nojoumian et al., "Social Secret Sharing in Cloud Computing Using a New Trust Function", 2012 Tenth Annual International Conference on Privacy, Security and Trust, pp. 161-167.

Nolan et al., "The P1073 Medical Information Bus Standard: Overview and Benefits for Clinical Users", 1990, pp. 216-219.

Omnilink Systems, Inc., "Portable Medical Equipment Tracking", <http://www.omnilink.com/portablemedicalequipmenttracking/>, Mar. 15, 2015, pp. 2.

O'Shea, Kristen L., "Infusion Management: Working Smarter, Not Harder", Hospital Pharmacy, Apr. 2013, vol. 48, No. 3, pp. S1-S14.

Package Management in Debian GNU/Linux, Debian GNU/Linux Expert Desktop Use Special, Giutsu-Hyohron Co., Ltd., First Edition, Sep. 25, 2004, pp. 183-185.

Passos et al., "Distributed Software Platform for Automation and Control of General Anaesthesia", Eighth International Symposium on Parallel and Distributed Computing, ISPDC '09, Jun. 30-Jul. 4, 2009, pp. 8.

Philips, "IntelliSpace Event Management and IntelliVue Patient Monitoring", Release 10, 2011, <http://incenter.medical.philips.com/doclib/enc/fetch/2000/4504/577242/577243/577247/582646/583147/8359175/Philips_Patient_Monitoring_and_IntelliSpace_Event_Management_Interoperability.pdf%3fnodeid%3d8508574%26vernum%3d-2>, pp. 2.

Pretty et al., "Hypoglycemia Detection in Critical Care Using Continuous Glucose Monitors: An in SilicoProof of Concept Analysis", Journal of Diabetes Science and Technology, Jan. 2010, vol. 4, No. 1, pp. 15-24.

Rahmani et al., "Smart e-Health Gateway: Bringing Intelligence to Internet-of-Things Based Ubiquitous Healthcare Systems", 2015 12th Annual IEEE Consumer Communications and Networking Conference (CCNC), Jul. 2015, pp. 826-834.

Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.

Ritchie et al., "A Microcomputer Based Controller for Neuromuscular Block During Surgery", Annals of Biomedical Engineering, Jan. 1985, vol. 13, No. 1, pp. 3-15.

Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.

Sanders et al., "The Computer in a Programmable Implantable Medication System (PIMS)", Proceedings of the Annual Symposium on Computer Application in Medical Care, Nov. 2, 1982, pp. 682-685.

Schilling et al., "Optimizing Outcomes! Error Prevention and Evidence-Based Practice with IV Medications", A Pro-Ce Publication, Hospira, Inc., Feb. 6, 2012, pp. 56.

Schulze et al., "Advanced Sensors Technology Survey", Final Report, Feb. 10, 1992, pp. 161.

Scott, et al., "Using Bar-Code Technology to Capture Clinical Intervention Data in a Hospital with a Stand- Alone Pharmacy Computer System", Mar. 15, 1996, American Journal of Health-System Pharmacy, vol. 53, No. 6, pp. 651-654.

Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.

Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.

Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.

Sheppard, Louis, Ph.D., "Computer Control of the Infusion of Vasoactive Drugs", Annals of Biomedical Engineering, Jul. 1980, vol. 8, No. 4-6, pp. 431-444.

Sheppard, Louis, Ph.D., "The Application of Computers to the Measurement, Analysis, and Treatment ofPatients Following Cardiac Surgical Procedures", The University of Alabama in Birmingham, Oct. 31, 1977, pp. 297-300.

Sheppard, Louis, Ph.D., "The Computer in the Care of Critically Ill Patients", Proceedings of the IEEE, Sep. 1979, vol. 67, No. 9, pp. 1300-1306.

"Sigma Spectrum: Operator's Manual", May 15, 2008, pp. 63. <https://usme.com/content/manuals/sigma-spectrum-operator-manual.pdf>.

"Sigma Spectrum: Operator's Manual", Oct. 2009, pp. 72. <http://static.medonecapital.com/manuals/userManuals/Sigma-Spectrum-Operator-Manual-October-2009.pdf>.

Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.

Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. <http://www.thomasland.com/hpj4209-832.pdf>.

Slack, W.V., "Information Technologies for Transforming Health Care", <https://www.andrew.cmu.edu/course/90-853/medis.dir/otadocs.dir/03ch2.pdf>, Ch. 2, 1995, pp. 29-78.

Smith, Joe, "Infusion Pump Informatics", CatalyzeCare: Transforming Healthcare, as printed May 12, 2011, pp. 2.

Sodders, Lisa, "VA Center Keeps Medicine in Right Hands", The Capital-Journal, Dec. 4, 1999, pp. 1-2.

"Software Versioning", Wikipedia.org, dated Oct. 16, 2011 in 11 pages, <https://en.wikipedia.org/w/index.php?title=Software_versioning&oldid=455859110>.

Solapurkar et al., "Building Secure Healthcare Services Using OAuth 2.0 and JSON Web Token in IOT Cloud Scenario", Dec. 2016, 2nd International Conference on Contemporary Computing and Informatics, pp. 99-10.

Stitt, F.W., "The Problem-Oriented Medical Synopsis: a Patient-Centered Clinical Information System", Proceedings of the Annual Symposium on Computer Application in Medical Care, 1994, pp. 88-92.

Stokowski, Laura A. RN, MS, "Using Technology to Improve Medication Safety in the Newborn Intensive Care Unit", Advances in Neonatal Care, Dec. 2001, vol. 1, No. 2, pp. 70-83.

Sutton et al., "The Syntax and Semantics of the PROforma Guideline Modeling Language", Journal of the American Medical Informatics Association, Sep./Oct. 2003, vol. 10, No. 5, pp. 433-443.

(56) References Cited

OTHER PUBLICATIONS

Szeinbach et al., "Automated Dispensing Technologies: Effect on Managed Care", Journal of Managed Care Pharmacy (JMCP), Sep./Oct. 1995, vol. 1, No. 2, pp. 121-127.

Szolovits et al., "Guardian Angel: Patient-Centered Health Information Systems", Technical Report MIT/LCS/TR-604, Massachusetts Institute of Technology Laboratory for Computer Science, May 1994, pp. 39.

"TCG TPM v2.0 Provisioning Guidance", Reference, Version 1, Revision 1, Mar. 15, 2017, pp. 1-43.

Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.

Van Den Berghe, M.D., Ph.D., et al., "Intensive Insulin Therapy in the Medical ICU", The New England Journal of Medicine, Feb. 2, 2006, vol. 354, No. 5, pp. 449-461.

Van Der Maas et al., "Requirements for Medical Modeling Languages", Journal of the American Medical Informatics Association, Mar./Apr. 2001, vol. 8, No. 2, pp. 146-162.

Villalobos et al., "Computerized System in Intensive Care medicine", Medical Informatics, vol. 11, No. 3, 1986, pp. 269-275.

Wilkins et al., "A Regular Language: The Annotated Case Report Form", PPD Inc., PharmaSUG2011—Paper CD18, 2011, pp. 1-9.

Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.

Yoo et al., "Code-Based Authentication Scheme for Lightweight Integrity Checking of Smart Vehicles", IEEE Access, 2018, vol. 6, pp. 46731-46741.

Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.

Yurkonis et al., "Computer Simulation of Adaptive Drug Infusion", IEEE Transactions on Biomedical Engineering, vol. BME-34, No. 8, Aug. 1987, pp. 633-635.

Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.

International Search Report and Written Opinion received in PCT Application No. PCT/US2014/021335, dated Jul. 8, 2014 in 13 pages.

International Preliminary Report on Patentability and Written Opinion received in PCT Application No. PCT/US2014/021335, dated Sep. 17, 2015 in 12 pages.

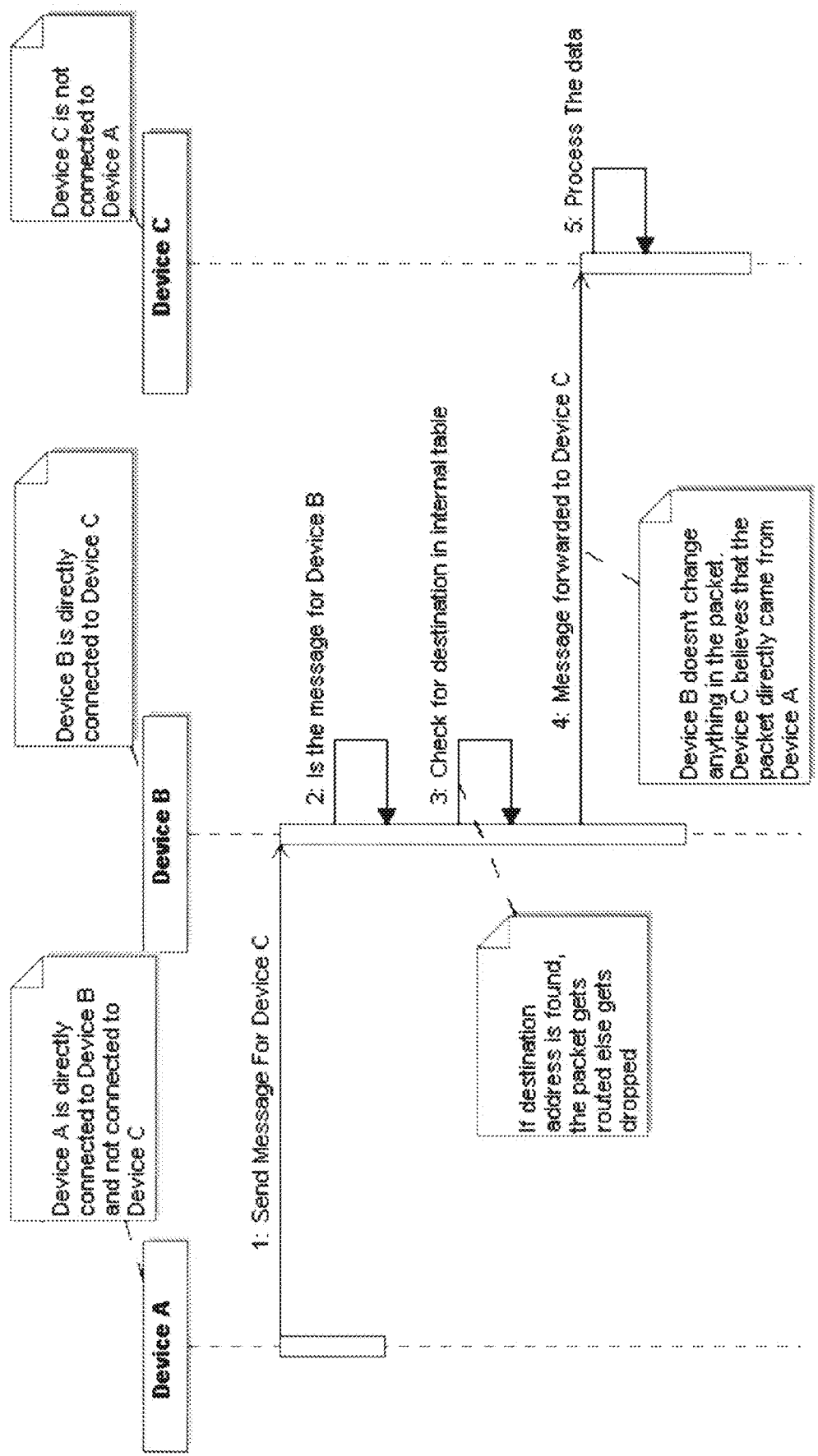

FIG. 10B

Connection Oriented Data Transfer

| Layer Flag [1 bit] | Connection Type [2 bits] | Message Type [4 bits] | CID | Data |
|---|---|---|---|---|
| 0 | Connection Oriented | Data | 1 Byte | N Bytes |

Connectionless Data Transfer

| Layer Flag [1 bit] | Connection Type [2 bits] | Message Type [4 bits] | Source Port | Destination Port | Data |
|---|---|---|---|---|---|
| 0 | Connection Less | Data | 1 Byte | 1 Byte | N Bytes |

Connection Request

| Layer Flag [1 bit] | Connection Type [2 bits] | Message Type [4 bits] | Command [1 Byte] | Source Port | Destination Port |
|---|---|---|---|---|---|
| 1 | Unknown | Connection | Connection Request | 1 Byte | 1 Byte |

Connection Accept

| Layer Flag [1 bit] | Connection Type [2 bits] | Msg. Type [4 bits] | Command [1 Byte] | CID | Destination Port | Source Port |
|---|---|---|---|---|---|---|
| 1 | Unknown | Connection | Connection Accept | 1 Byte | 1 Byte | 1 Byte |

Connection Acknowledgement

| Layer Flag [1 bit] | Connection Type [2 bits] | Message Type [4 bits] | Command [1 Byte] | CID | Source Port |
|---|---|---|---|---|---|
| 1 | Unknown | Connection | Connection Ack. | 1 Byte | 1 Byte |

Connection Disconnect

| Layer Flag [1 bit] | Connection Type [2 bits] | Message Type [4 bits] | Command [1 Byte] | CID | Source Port |
|---|---|---|---|---|---|
| 1 | Unknown | Connection | Connection Disconnect | 1 Byte | 1 Byte |

Connection Disconnect Ack

| Layer Flag [1 bit] | Connection Type [2 bits] | Message Type [4 bits] | Command [1 Byte] | CID | Source Port |
|---|---|---|---|---|---|
| 1 | Unknown | Connection | Connection Disconnect Ack | 1 Byte | 1 Byte |

FIG. 10C

Connection Reject

| Layer Flag [1 bit] | Connection Type [2 bits] | Msg. Type [4 bits] | Command [1 Byte] | Destination Port | Source Port | Reason |
|---|---|---|---|---|---|---|
| 1 | Unknown | Connection | Connection Reject | 1 Byte | 1 Byte | 1 Byte |

CID Info Request

| Layer Flag [1 bit] | Connection Type [2 bits] | Message Type [4 bits] | Command [1 Byte] | CID | Source Port |
|---|---|---|---|---|---|
| 1 | Unknown | CID | CID Info Request | 1 Byte | 1 Byte |

CID Info Response

| Layer Flag [1 bit] | Conn. Type [2 bits] | Msg. Type [4 bits] | Command [1 Byte] | CID | Source Port | Info Length [1 Byte] | CID Info |
|---|---|---|---|---|---|---|---|
| 1 | Unknown | CID | CID Info Response | 1 Byte | 1 Byte | 1 Byte | 1 Byte |

Socket Status Request

| Layer Flag [1 bit] | Conn. Type [2 bits] | Message Type [4 bits] | Command [1 Byte] | CID | Source Port |
|---|---|---|---|---|---|
| 1 | Unknown | Socket | Socket Status Request | 1 Byte | 1 Byte |

Socket Status Response

| Layer Flag [1 bit] | Conn. Type [2 bits] | Msg. Type [4 bits] | Command [1 Byte] | CID | Source Port | Info Length [1 Byte] | Socket Status |
|---|---|---|---|---|---|---|---|
| 1 | Unknown | Socket | Socket Status Res | 1 Byte | 1 Byte | 1 Byte | 1 Byte |

Subscribe To Service

| Layer Flag [1 bit] | Connection Type [2 bits] | Message Type [4 bits] | Command [1 Byte] | Source Port | Destination Port |
|---|---|---|---|---|---|
| 1 | Unknown | Service | Subscription Request | 1 Byte | 1 Byte |

Subscription To Service Ack

| Layer Flag [1 bit] | Connection Type [2 bits] | Msg. Type [4 bits] | Command [1 Byte] | CID | Destination Port | Source Port |
|---|---|---|---|---|---|---|
| 1 | Unknown | Service | Subscription Ack | 1 Byte | 1 Byte | 1 Byte |

FIG. 10D

Subscription Reject

| Layer Flag [1 bit] | Conn. Type [2 bits] | Msg. Type [4 bits] | Command [1 Byte] | Destination Port | Source Port | Reason |
|---|---|---|---|---|---|---|
| 1 | Unknown | Service | Subscription Reject | 1 Byte | 1 Byte | 1 Byte |

Unsubscribe From Service

| Layer Flag [1 bit] | Conn. Type [2 bits] | Msg. Type [4 bits] | Command [1 Byte] | CID | Source Port |
|---|---|---|---|---|---|
| 1 | Unknown | Service | Unsubscribe Request | 1 Byte | 1 Byte |

Unsubscribe From Service Ack

| Layer Flag [1 bit] | Conn. Type [2 bits] | Msg. Type [4 bits] | Command [1 Byte] | CID | Source Port |
|---|---|---|---|---|---|
| 1 | Unknown | Service | Unsubscribe Request Ack | 1 Byte | 1 Byte |

Device Address Request

| Layer Flag [1 bit] | Conn. Type [2 bits] | Msg. Type [4 bits] | Command [1 Byte] | CID | Source Port |
|---|---|---|---|---|---|
| 1 | Unknown | Device Info | Device Address Request | 1 Byte | 1 Byte |

Device Address Response

| Layer Flag [1 bit] | Conn. Type [2 bits] | Msg. Type [4 bits] | Command [1 Byte] | CID | Source Port | Info Length [1 Byte] | Device Address |
|---|---|---|---|---|---|---|---|
| 1 | Unknown | Device Info | Device Addr. Resp. | 1 Byte | 1 Byte | 1 Byte | 1 Byte |

Device Type Request

| Layer Flag [1 bit] | Conn. Type [2 bits] | Msg. Type [4 bits] | Command [1 Byte] | CID | Source Port |
|---|---|---|---|---|---|
| 1 | Unknown | Device Info | Device Type Request | 1 Byte | 1 Byte |

Device Type Response

| Layer Flag [1 bit] | Conn. Type [2 bits] | Msg. Type [4 bits] | Command [1 Byte] | CID | Source Port | Info Length [1 Byte] | Device Name |
|---|---|---|---|---|---|---|---|
| 1 | Unknown | Device Info | Device Type Response | 1 Byte | 1 Byte | 1 Byte | 1 Byte |

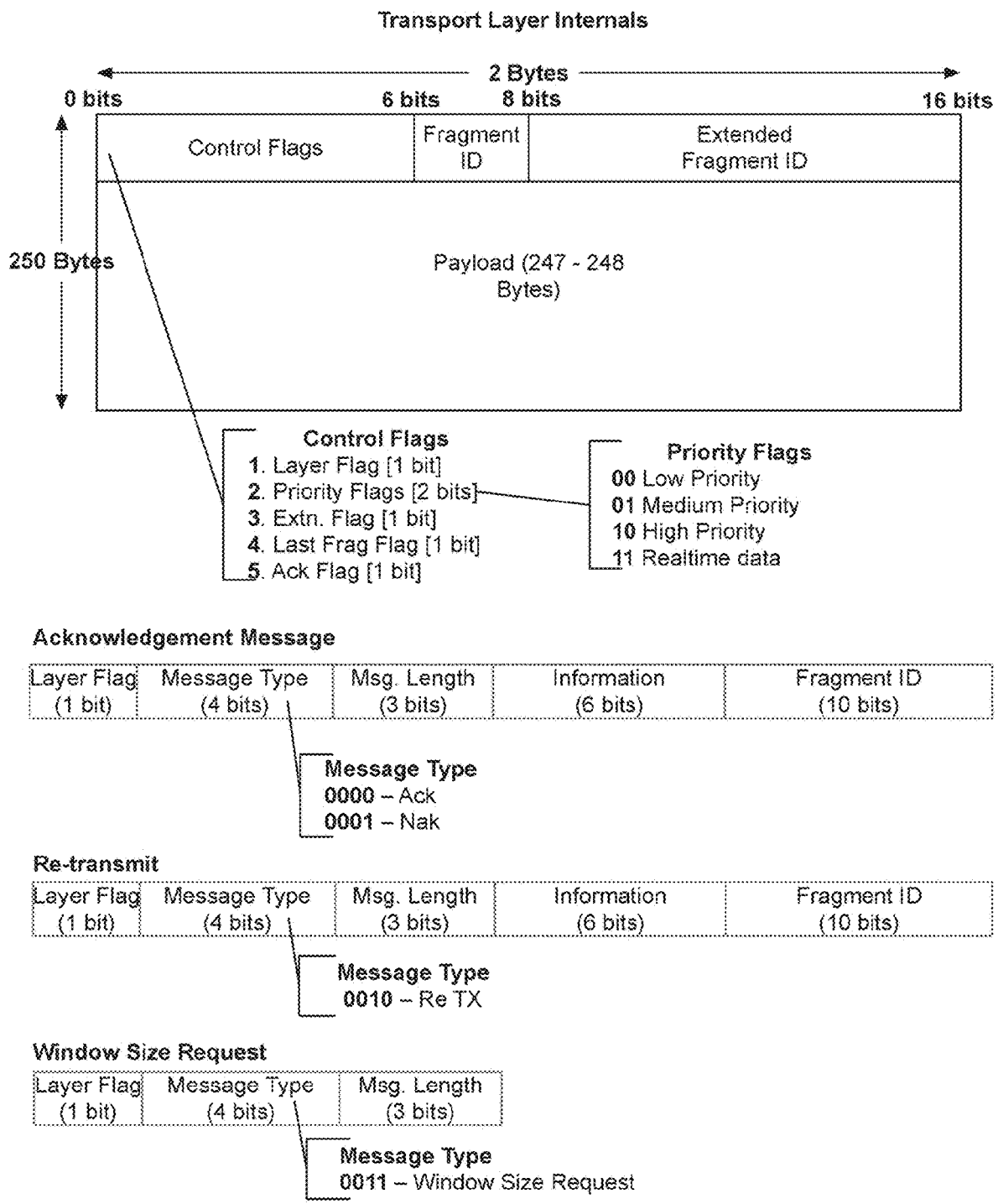

FIG. 11B
Window Size Response
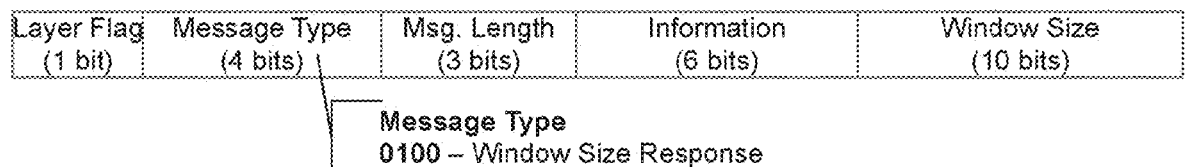
Message Type
0100 – Window Size Response
Ping
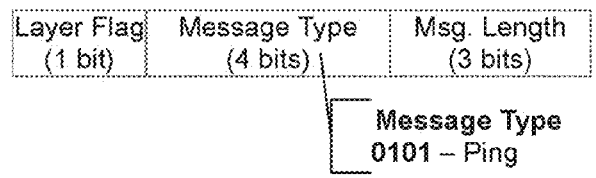
Message Type
0101 – Ping
Ping Response
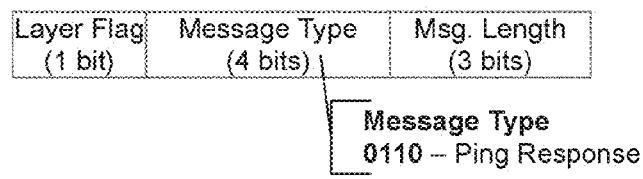
Message Type
0110 – Ping Response
Intent
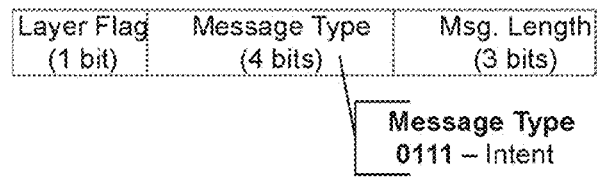
Message Type
0111 – Intent

FIG. 12B

Disassociation Message

| SOF | Destination Address | Source Address | Message Length | Message Type | CRC |
|---|---|---|---|---|---|
| 1 Byte | 01 | 1 Byte | 1 | Disconnect. Request | 2 Bytes |

Request Device Type Message

| SOF | Destination Address | Source Address | Message Length | Message Type | CRC |
|---|---|---|---|---|---|
| 1 Byte | 1 Byte | 1 Byte | 1 | Device Type Request | 2 Bytes |

Device Type Response Message

| SOF | Destination Address | Source Address | Message Length | Message Type | Device Type | CRC |
|---|---|---|---|---|---|---|
| 1 Byte | 1 Byte | 1 Byte | 2 | Device Type Response | 1 Byte | 2 Bytes |

Device Status Request Message

| SOF | Destination Address | Source Address | Message Length | Message Type | CRC |
|---|---|---|---|---|---|
| 1 Byte | 1 Byte | 1 Byte | 1 | Device Status Req. | 2 Bytes |

Device Status Response Message

| SOF | Destination Address | Source Address | Message Length | Message Type | Device Status | CRC |
|---|---|---|---|---|---|---|
| 1 Byte | 1 Byte | 1 Byte | 2 | Device Status Resp. | 1 Byte | 2 Bytes |

Device Status Duration Message

| SOF | Destination Address | Source Address | Message Length | Message Type | Device Status | CRC |
|---|---|---|---|---|---|---|
| 1 Byte | 1 Byte | 1 Byte | 2 | Status Duration | 1 Byte | 2 Bytes |

Data Re-Transmission Request Message

| SOF | Destination Address | Source Address | Message Length | Message Type | CRC |
|---|---|---|---|---|---|
| 1 Byte | 1 Byte | 1 Byte | 1 | Data ReTransmis. | 2 Bytes |

MEDICAL DEVICE COMMUNICATION METHOD

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

One or more embodiments of the invention are related to the field of multiplex communication protocols for medical devices such as, but not limited to, infusion pumps. More particularly, but not by way of limitation, embodiments of the invention enable a medical device communication method for communication between connected peripherals and subsystems that includes connection-oriented, connectionless-oriented, broadcast and multicast data exchange with priority handling of data, fragmentation and reassembly of data, unique static and dynamic address assignment and hot swap capabilities.

Description of the Related Art

Devices that exchange data generally do so using a communication protocol. Communication protocols enable data to be transmitted and received in a controlled manner. Medical devices are example devices that may utilize a communication protocol, for example to exchange data between peripherals or subsystems that generate or utilize data. There are many types of communications protocols that vary in complexity, efficiency and hardware utilization. Current communication protocols utilized within medical devices make use of the operating system and particular bus architecture within the medical device. A problem with this type of architecture is that some implementations may prevent time-multiplexed access of the communication link, thereby starving or otherwise preventing multiple applications from communicating simultaneously. In addition, applications that transfer data using operating system and bus specific software calls must be altered when the operating system or bus architecture changes, specifically to account for differences in operating system calls or with respect to the bus architecture, different data formatting, sequencing and any other protocol specific nuances. In addition, medical devices in general must undergo extensive testing to ensure that they do not fail. Thus, changing bus architectures increases costs associated with applications that make use of the bus architecture, since the application must be retested if the source code for the application is altered.

Known communications protocols are generally targeted at a specific type of communication bus architecture, for example Ethernet, WiFi, Bluetooth, CAN, Serial, I2C, SPI, etc. Known communication protocols in general are not capable of use with more than one type of communication bus since they attempt to provide a solution to a specific communication problem in a coherent manner. Because of the low power requirements, limited processor capabilities and limited memory capacity of medical devices with embedded processors that do specific functions or tasks, such as infusion pumps, existing sophisticated communications protocols are generally not utilized in such medical devices.

In summary, known solutions use communication protocols that are tied to a specific operating system and/or communications bus. Unfortunately, these communication protocols are not agnostic to all communication bus types and do not provide an efficient and lightweight protocol stack for intra-device communication that includes connection-oriented, connectionless-oriented, broadcast and multicast data exchange with priority handling of data, fragmentation, and reassembly of data, unique static and dynamic address assignment for connected subsystems and hot swap capabilities. For at least the limitations described above there is a need for a medical device communication method that provides these features as described and claimed herein.

SUMMARY OF THE INVENTION

Embodiments of the invention enable a medical device communication method for communication between medical peripherals and subsystems that includes connection-oriented, connectionless-oriented, broadcast and multicast data exchange with priority handling of data, fragmentation and reassembly of data, unique static and dynamic address assignment and hot swap capabilities. Example medical devices that may employ an embodiment of the invention include but are not limited to infusion pumps, both present and future. Embodiments of the communication protocol provide an interface that is detached, or otherwise abstracted from the operating system and underlying bus architecture within the medical device, making the behavior and interface of communication protocol consistent across bus architectures and operating systems, which is unknown in the art of infusion pumps for example. Hence, the same application may be utilized on multiple hardware platforms, for example without altering the application itself. Thus, embodiments enable simplified application code, portability thereof and minimize maintenance and testing requirements. Embodiments may utilize any type of physical communication path, for example wireless or hardwired, including but not limited to a data bus. Embodiments for intra-device communications over a data bus generally employ data bus drivers specific to each type of data bus to control reading and writing of data over the bus along with a standard interface to these data bus drivers.

Embodiments may be implemented in separate layers of software configured to execute on one or more computing elements, wherein each layer performs operations to provide data exchange that is generally independent of the other layers. Each layer for example may create, read or update headers associated with data to be exchanged, wherein the headers contain information to support the above-mentioned features. The layers make up what is known as a protocol stack. Embodiments of the protocol stack may include a manager layer, session layer, transport layer, and data link layer or any other architecture as long as the resulting implementation provides the functionality described herein.

Depending on the peripheral or subsystem, data type, priority and desired reliability of data to be exchanged, applications may transmit data using connection-oriented data exchange to provide guaranteed delivery of data or connectionless data exchange for less sensitive data. Embodiments also support one-to-one, as well as one-to-many and many-to-one multicast, and broadcast modes of data exchange between connected peripherals and subsystems. At least one embodiment also supports priority based data exchange and gives preference to high priority data over low priority data to ensure that high priority messages are delivered first. Additionally, at least one embodiment supports data fragmentation and reassembly data to comply with demands of the particular physical communication technology. Embodiments also provide unique static and dynamic address assignment for connected subsystems and hot swap capabilities, which are unknown for example in current infusion pumps.

Specifically, in the case of connection-oriented communication, at least one embodiment utilizes a Communication ID or "CID", as a token to uniquely identify all active connections within a subsystem and route the data between respective applications. In the case of connectionless communications, at least one embodiment uses port numbers, for example source and destination port numbers, to identify the targeted application. At least one embodiment supports subscription services for recipient applications, which enables multicasting of data to all subscribed applications. Multicasting can be both connection-oriented and connectionless. In connection-oriented communication sessions, at least one embodiment guarantees delivery of data, for example using acknowledgements. Alternatively, connectionless communication sessions do not guarantee delivery of data, but are very efficient. At least one embodiment supports broadcasting of data/messages, wherein the broadcast messages are forwarded to all the subsystems connected to the broadcasting subsystem.

Applications may need to exchange data larger in size than an underlying communication technology or data bus can support. In such cases, at least one embodiment breaks or fragments the data into a smaller size, for example that the data bus can actually transfer. At least one embodiment reassembles data into the original data size at the receiving end. At least one embodiment executes on embedded systems that may have limited resources, including memory, processing power, bus utilization, and power. Hence, embodiments efficiently utilize available resources. Example data exchanges that are large enough to warrant fragmentation of messages include drug library downloads and firmware updates.

With respect to fragmentation, at least one embodiment utilizes window that represents a count of fragments that may be sent before receiving an acknowledgement from receiver. In at least one embodiment, the transmitter requests for window size from the receiver before sending the first fragment. The receiver determines the available memory space to accommodate received packets and responds with the window size, for example as an integral multiple of the maximum frame size that fits into the available memory. The transmitter numbers the fragments in sequence and sends them to receiver. After a window size worth of messages have been sent, the transmitter waits for an acknowledgement of the last fragment. The receiver accumulates all the received fragments and verifies that all the received fragments are in sequence. If there is no missing fragment, the receiver sends the fragment number of last fragment as an acknowledgement, or otherwise sends the fragment numbers of missing fragments as part of negative acknowledgement or NAK.

Since medical devices such as infusion pumps in the future may include hot swappable peripherals or subsystems, at least one embodiment supports unique address assignments to connected devices in order to provide conflict free exchange of data, thus reducing complexity in applications. At least one embodiment supports communication over multiple underlying data transfer technologies such as serial, CAN, SPI, SDIO, USB, or any other type of physical medium or data bus. At least one embodiment also keeps track of devices connected on each bus and routes data onto the respective bus.

BRIEF DESCRIPTION OF THE DRAWINGS

The above and other aspects, features and advantages of the invention will be more apparent from the following more particular description thereof, presented in conjunction with the following drawings wherein:

FIG. 9 illustrates an activity diagram showing routing between various devices.

FIGS. 10A-D illustrate the structure of the messages of the Session Layer.

FIGS. 11A-B illustrate the structure of the messages of the Transport Layer.

FIGS. 12A-B illustrate the structure of the messages of the Data Link/Physical Layer.

DETAILED DESCRIPTION OF THE PREFERRED EMBODIMENT

A medical device communication method will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
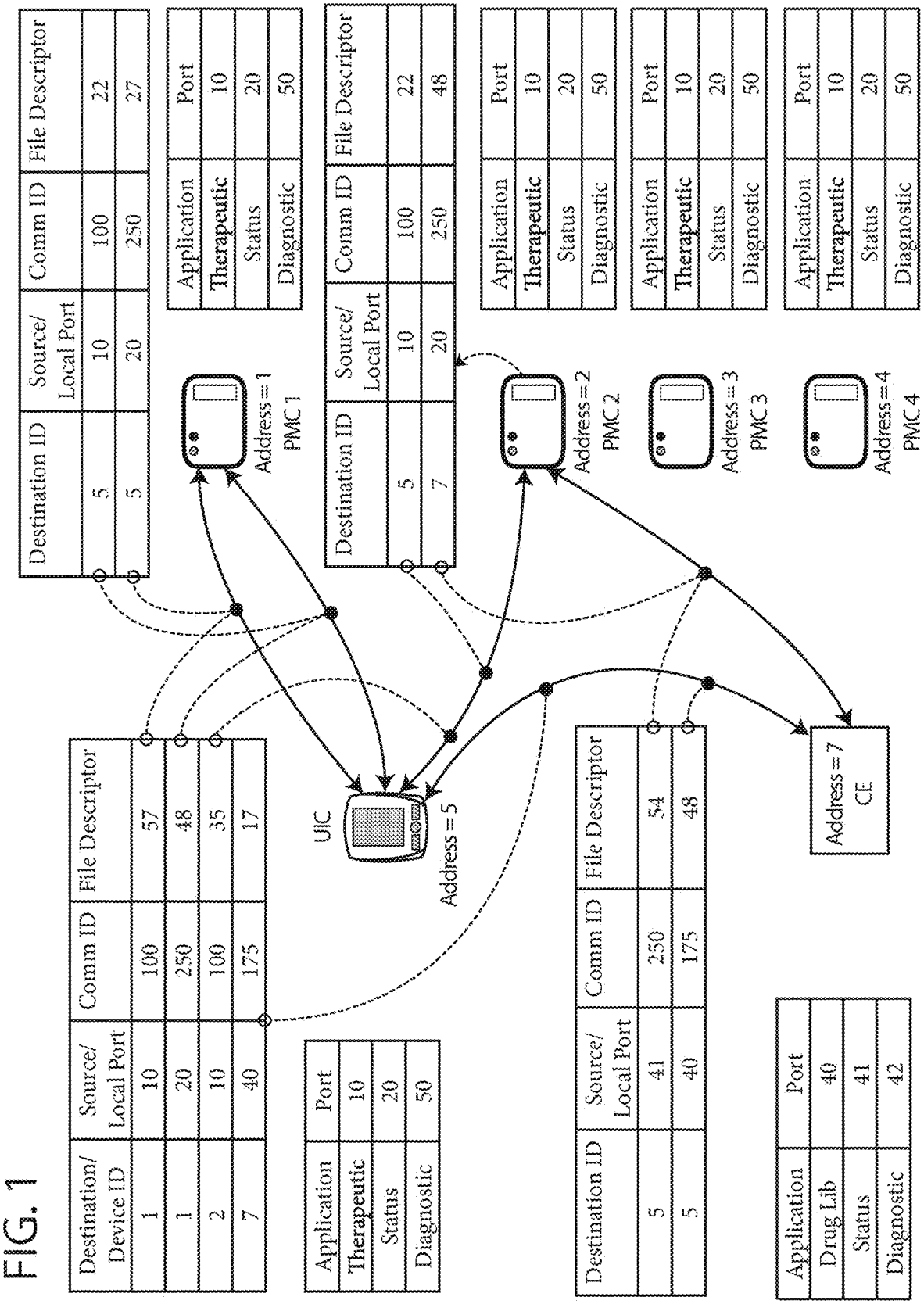
FIG. 1 illustrates an architectural view of a system having a user interface controller, and multiple peripherals that communicate with one another using an embodiment of the invention.

FIG. 1 illustrates an architectural view of a system having user interface controller or "UIC", and multiple peripherals that communicate with one another using an embodiment of the invention. As shown user interface controller UIC communicates with peripherals Pump Motor Control or "PMC", PMC 1 and PMC 2 as well as communication engine or "CE" for various applications including but not limited to drug library, status and diagnostic message handling. For exemplary purposes, UIC has a destination/device ID, e.g., an address of 5 and messages from UIC to the other devices travel over pathways uniquely defined by the tuples defined in the table, for example on a per device and communication ID defined channel. These channels are shown in the table above UIC, namely between UIC and PMC 1, at ports 10 and 20, i.e., the therapeutic and status ports, via Communication ID or "CID" 100 and CID 250 respectively followed by a channel used between UIC and PMC 2 at port 10, the therapeutic port, via Communication ID 100, along with a channel between UIC and CE at port 40, via Communication ID 175. The CE, whose address is 7, shows channels in the table above CE to PMC 2 and the UIC, namely devices 2 and 5 via Communication ID's 250 and 175 respectively. PMC 1 is illustrated as having channels to the UIC, via Communication ID's 100 and 250. PMC 2 is illustrated as having channels to the UIC and CE through ports 10 and 20, via Communication ID's 100 and 250. PMC 3 and 4 may be hot swapped into the system or otherwise commanded or queried on the fly. Embodiments of the invention are generally configured to utilize minimal memory and processing to enable execution on devices having limited memory and limited processing power, which is generally unknown in the art with respect to sophisticated communications protocols for example. In one or more embodiments, the stack utilizes one kernel thread to execute the Data Link layer and Transport lower layer, whereas remaining layers are part of application process and execute in the context of application. Minimum thread implementation supports blocking access, for example read and write operations block until the operation is completed. Embodiments may also support asynchronous callbacks, and in such cases, the stack may utilize two threads, one for write operations and one for read operation, hence total number of threads utilized is 2*N+1, where N is the number of applications using the stack.

Figure 2:
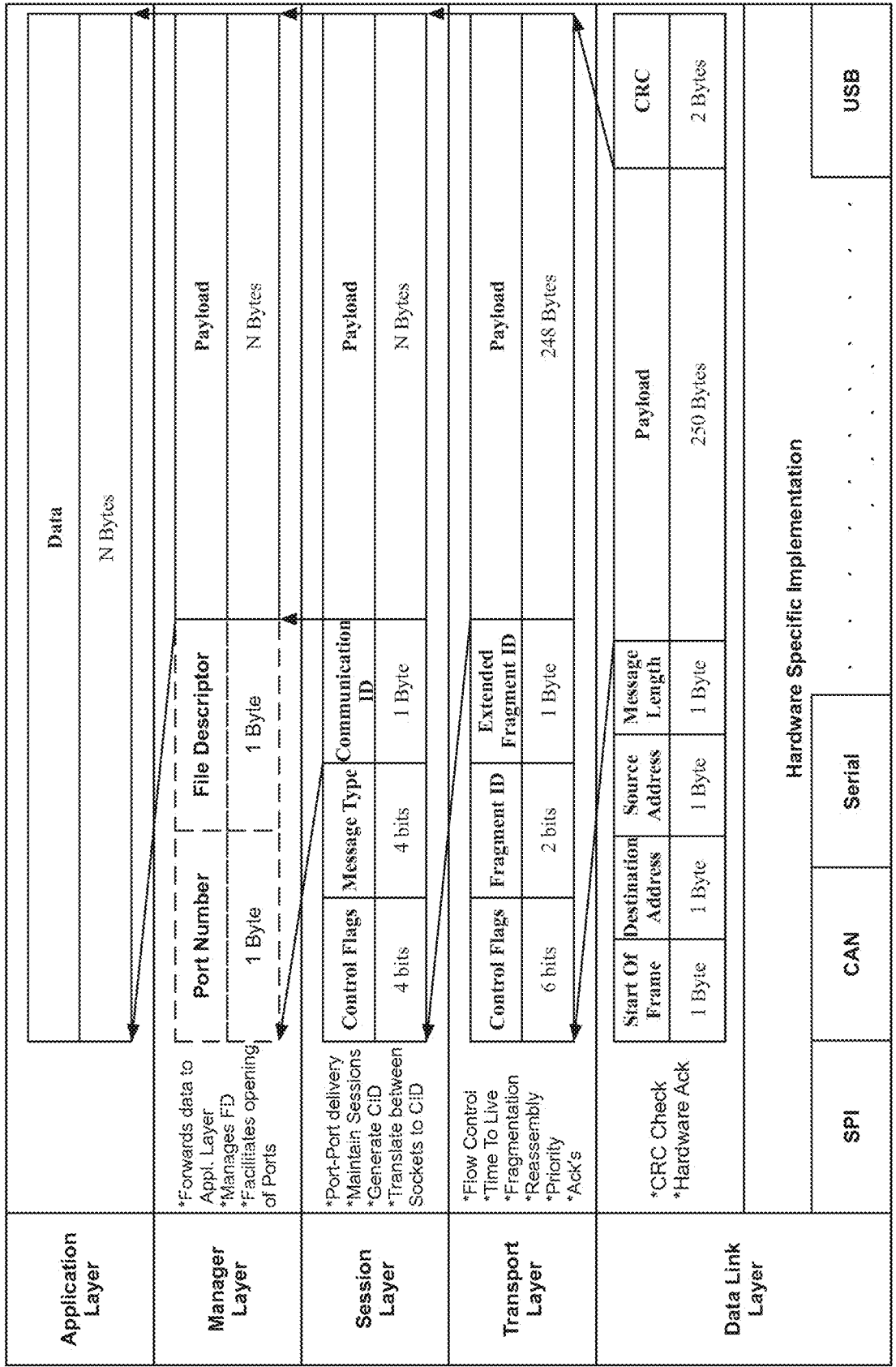
FIG. 2 illustrates a hierarchical layered embodiment of the invention implemented as a protocol stack.

FIG. 2 illustrates a hierarchical layered embodiment of the invention implemented as a protocol stack. As shown, a data message in the application layer is N bytes long. The application layer may include any functionality independent of the protocol stack that is implemented in the layers beneath the application layer as shown. When the message is transmitted from one application to another, for example to an application executing on a peripheral or subsystem, control information or headers are appended to the message as the message descends layers. The various headers or other appended information are removed as the message rises through the protocol stack to the respective receiving application.

In one or more embodiments, a manager layer may be utilized to implement the first layer in the protocol stack beneath the application. The manager layer may provide standard interfaces to applications across any desired operating system. The layer provides application programmer interfaces or API's that enables socket-based communications between applications. The manager layer also manages file descriptors and facilitates opening of ports. In at least one embodiment, the manager layer creates and otherwise utilizes a message header having a port number and file descriptor.

Figure 10A:
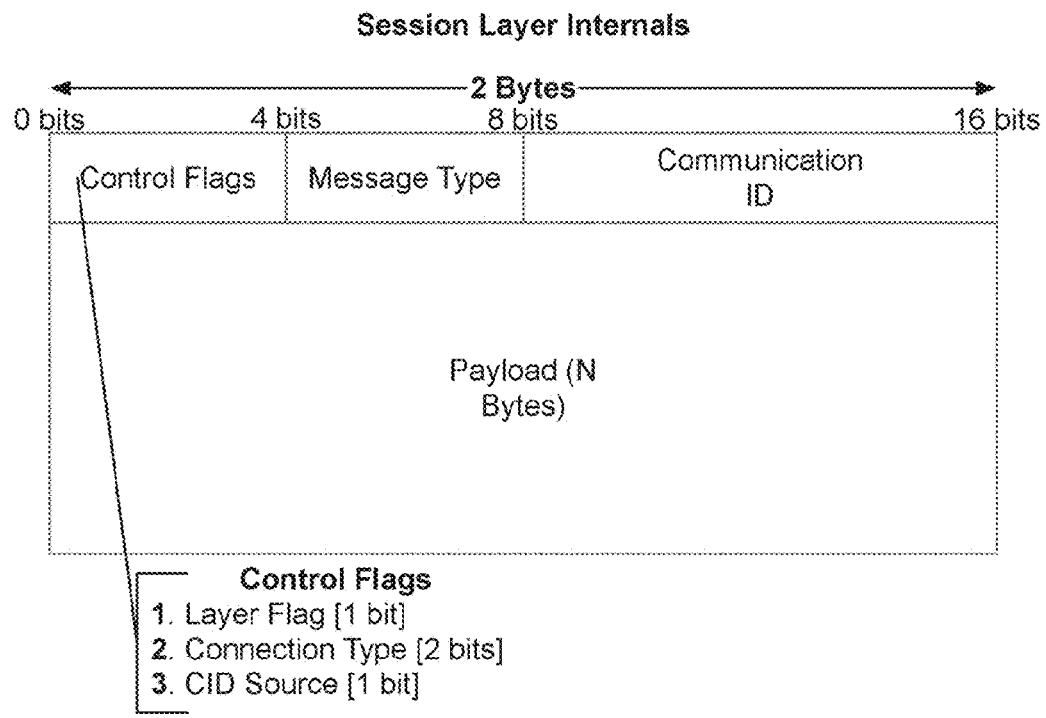

A session layer is another layer in the protocol stack and provides or includes API's to exchange data and control between manager layer and session layer. The session layer may provide guaranteed application-to-application delivery of data and enables connection-oriented and connectionless-oriented modes of communication. This layer also enables one-to-one, one-to-many, many-to-one multicast and broadcasting mode of communication. The layer maintains the translation between CID and an associated socket or virtual port. For connection-oriented communication, the protocol utilizes the CID and otherwise generates and utilizes CID's. As the connection-oriented data exchange utilizes a handshake between applications for data exchange, the session layer handles the handshake and generates a CID for the communication and informs the other participating session layers of application(s) about the CID. After the handshake, data packets utilize the CID for communication. In case of connectionless communication, no CID is utilized and hence both source and destination port addresses are exchanged in each communication packet or payload. In at least one embodiment, the manager layer creates and otherwise utilizes a message header having control flags and a message type along with a communication identifier. This structure along with an exemplary connection table is shown in FIG. 10A, along with exemplary message types in FIGS. 10B-D. The control flags may be implemented with a layer flag of 1 bit, a connection type of 2 bits and a CID source of 1 bit for example. The session layer utilizes some messages that are associated with the session-session communications and are never passed up the stack to the manager layer in one or more embodiments. These messages are generally used for establishing or closing connections, acknowledgements, etc. If the layer flag is set, for example set to True or 1, the message will be consumed at session layer and will not be forwarded up the stack. The connection type flag indicates the type of connection, for example if connection-oriented, set to 01 or if connectionless, set to 00. An example connectionless protocol is User Datagram Protocol or UDP while an example connection-oriented protocol is Transmission Control Protocol or TCP. The CID source bit is used to identify if the data as being sent from the entity that generated CID for the connection in use or from submodules using this CID for communication. The entity that generates CID for communication sets this bit for all the messages generated by it for the respective active connection, while other entities involved in communication reset this flag for messages while using this CID. As the CID is unique within the entity generating CID, there may be duplicate CIDs across other entities. Hence, this layer helps in resolving the source of CID (local or remote) via this flag. The message type field associates messages with categories and lets the session layer know what to expect in the following fields. The message type field is a 4-bit wide field in one or more embodiments. The message type field is used to determine the type of message. Exemplary values include 0000 for data, 0001 for connection, 0010 for CID, 0011 for socket, 0100 for service and 0101 for device information. Any module that provides a service generates a unique CID for communicating with the consumers of the service. Communication ID '0' is reserved for connectionless type of communication in one or more embodiments. Communication ID field is 1 byte wide and is utilized for the data that is passed up the protocol stack. CID can hold any number between 0-255. As state above, CID '0' is for connectionless type communication and is thus not a valid ID for connection-oriented communication. Connection oriented type communications will have a CID in the range of 1-255. Hence, CID '0' is an implicit indication of connectionless communication, any other number between 1-255 suggests connection-oriented. Applications may establish one or more notification filters to select message to receive and process using a desired function. The filtration mechanism may utilize one or more regular expression that specifies the location, length and content of the matching data in the data portion of the packet. This functionality is implemented in the management layer in one embodiment of the invention. Before the management layer forwards the data to application, it may check if any filters are defined on the data. Depending on the filter, the manager layer filters data and forwards the data to respective callback handlers.

Embodiments of the invention enable a single application to maintain connections with more than one device over one or more physical communication layers or bus implementations. This is accomplished by the use of virtual ports. A single application such as the Therapeutic Manager in the UIC may for example maintain open connections with more than one drug pump PMC or other device as would be asserted during a multi-channel infusion. Similarly, many applications may maintain a connection with one application or device, for example, UIC, CE, and other applications may connect to a particular PMC to gather infusion status information.

The one-to-many and/or many-to-one communication relationship can further be classified into three types, unicast, multicast and broadcast. For example, different applications can gather infusion status from a PMC either by requesting, for example via multicasting, or the PMC can broadcast its status on a known port and interested applications can listen to the port. Listening to a known port can be either anonymous or subscription based. In anonymous mode, broadcasting application continuously transmits on a known port and any application can listen to the port. In subscription based mode, the broadcasting application will not transmit until there is at least one recipient, interested application, which will have to request for service and disconnect when done using the service.

Virtual ports can be implemented by enabling a handshake between participating modules/applications. Applications providing the service generally open a port and connect to the port. For every accepted connection request, CID is generated by the service provider and is passed back to requesting entity in an acknowledgement. Subsequent communication is performed using this CID. In general, the CID is unique to the entity that generated it. A disconnection message is used to stop communication and the CID is then returned to the pool, for example to be reused later. If the service provider runs out of CIDs, it may return a NAK to incoming connection requests with appropriate NAK ID. In case of communication failure, for example module shut down, too much waiting time, too many retries, etc., after waiting for sufficient retries to send a message, one or more embodiments may assume that the communication has stopped and CID is then returned to pool. As the CID are generated by the service provider and are unique within the entity, there can be duplicate CIDs on other sub-entities. To avoid the conflict because of duplicate CIDs, two CID tables may be maintained, one for the CID generated by the system, and the other for the CIDs generated by other systems engaged in communication. The creator of CID sets the "CID Source" flag, hence when other involved applications look at this flag, they perform lookup in appropriate CID table. Each entity may therefor maintain a table shared by the applications running on it. This table is maintained at the session layer and serves as a reference table for routing incoming data packets to respective ports/sockets.

As example scenario is illustrated in the following table, and is also shown in the bottom portion of FIG. 10A for illustration purposes and is not intended to limit the invention as claimed. As shown, the connection type may be set to a value indicative of a connection-oriented type of communication, such as TCP as shown, or a connectionless communication type, such as UDP as shown, or a "Service", for example an application that exists to log data for other applications. The destination address, destination port and communication ID generally uniquely identify a row in above-mentioned table. Destination address is the logical address of a device engaged in a communication. Embodiments may support repeated entries with the same destination address, which indicates multiple active connections with the same destination device. The source port field stores the local port number responsible for handling communication(s) with the CID associated therewith. Depending on CID, received messages are routed to the respective port. Multiple repeated entries in the source port column suggest various applications communicating over same port, which may be indicative of one-to-many communication for example. In one or more embodiments, applications may register or otherwise provide a request to a service provider to receive messages. The destination port is the port number on the destination device engaged in a communication. The communication between a destination port and the local port associated therewith takes place over the respective CID. Hence, CID behaves as a key for this communication. Since the CID is a unique number assigned to distinct communication requests, and which may be implemented with a particular data type of a certain size, there may be an upper limit to the number of active connections that can be handled by the system/application. The upper limit is thus an upper numerical limit of the CID. Once the count of unique CID's exceeds the upper limit, one or more embodiments send a NAK to new incoming connection requests. The File Descriptor (FD) functions similar to file handler or file descriptor in standard operating systems as one skilled in the art will recognize. Communication related operations are performed using this descriptor. Repeating entries of FD suggests multiple connections are being served by one application, many-to-one type of communication. See also FIGS. 10B-D for specific message structures utilized in one or more embodiments of the invention.

| Connection Type | Destination Address | Destination Port | Source Port | CID | File Descriptor |
|---|---|---|---|---|---|
| Service | 8 | 50 | 40 | 100 | 55 |
| TCP | 5 | 23 | 60 | 72 | 63 |
| Service | 15 | 68 | 40 | 110 | 87 |
| UDP | 4 | 20 | 55 | 103 | 21 |

The transport layer is another layer in the protocol stack and is responsible for transport layer to transport layer delivery of data. This layer handles flow control, timeouts, acknowledgements and fragmentation and reassembly of data and also resolves the data priority. At least one embodiment of the protocol stack supports two or more priority levels, for example three priority levels, High priority, Medium priority and Low priority and depending on the priority of data, the transport layer puts the data in a respective priority queue. The transport layer may be implemented with two sub-layers namely the transport upper and lower layers. The transport upper layer along with manager and session layers resides in application space, whereas the transport lower layer along with data link layer resides in kernel space. The transport upper layer handles reading and writing to priority queues, fragmentation and reassembly of data and transport-to-transport layer acknowledgements, whereas the transport lower layer may be implemented as a very thin layer and handles reading from priority queues and communication with one or more other stack layers, for example a lower stack layer. This structure along with an exemplary message types in FIGS. 11A-B.

The transport layer generally ensures that manageable sized datagrams are sent over the underlying bus. Hence, this layer looks at the data coming from upper layers and if the size of data exceeds Maximum Transmission Unit (MTU) size, the layer fragments the incoming data to fit within MTU boundary. Thus, embodiments of the invention may utilize any type of bus of any size, e.g., one bit as per a serial bus, or multiple bits as per a parallel bus of any width. The layer adds appropriate information to the data so that it can be reassembled faithfully at the receiving end. If the incoming data can be sent in three fragments, 'Fragment ID' field is used to number the fragments starting from '1' and the 'Extended flag' bit is not used. All zeros in the 'Fragment ID' field indicates an un-fragmented message and hence is treated as a standalone message. If a message requires more than three fragments to be transmitted, 'Extended Flag' is set, which enables an extra of 8 bits (Extended Fragment ID field is 8 bits) to be used for numbering the fragments. With this flag set, there are total of 10 bits available for numbering which can support 1023 ($2^{10}-1$) fragments. At the receiving end, 'Extended flag' is inspected to determine if 'Extended Fragment ID' is used or not. If the flag is set, the receiver assumes the fragments to arrive in sequence, starting from sequence number 1. But, if the flag is not set, the receiver inspects the 'Fragment ID' field. If the 'Fragment ID' field has zero in it, it indicates an independent message, but if it's a non-zero value, the receiver treats the received message as fragmented data (expects a maximum of three packets). Once all of the fragments are received, the receiver will re-assemble all the fragments into one message. To do this, the receiver aligns all the received messages in ascending order of their fragment ID. Then the receiver verifies that no fragment has been missed in the sequence. If all fragments are received successfully, the receiver removes the 'Transport layer' header information from all the related fragments and concatenates them into one message. If Transport layer has limited memory to re-assemble all the fragments, it forwards the fragments up the stack, as they arrive, which gets reassembled in application buffer.

Congestion control is also provided by the transport layer, which may implement messages dedicated specifically for transport layer to layer communication. These specific messages are consumed at transport layer and not passed up the stack. One such message is the window message, which is exchanged to determine window size for data exchange.

Before sending the first fragment from fragmented data, the transmitter requests a window size from receiver. The receiver looks at the available buffer space in the application buffer and computes the number of fragments it can stage before running out of available memory. It responds to transmitters request with this computed number as window size. Then the transmitter sends window size worth of fragments before expecting an acknowledgement. Once the receiver receives all the messages transmitted in a window, it verifies that all the fragments are in desired sequence and sends acknowledgement for last received fragment in the sequence. If the receiver determines that fragment(s) is missing, it sends an NAK for the missing fragment and the transmitter re-transmits the respective fragment(s). The transmitter may check for window size in middle of communication to keep the data exchange optimized, also, if the receiver gets low on resources, it can explicitly send a window response and update the transmitter about the window size.

The transport layer is also responsible for the reliable delivery of data. The transport layer has ability to ensure delivery of data to the receiving end. Transport layer has a field for acknowledgement. The receiver may send an acknowledgement for every received data packet with the acknowledgement flag set. In case of fragmented messages, an acknowledgement is sent when the last fragment in a window has been received or last frame in the message has been received or timer expires before all messages have been received.

Embodiments of the transport layer may also implement a "time to live". For example, after transmitting a message, the transmitter initiates a timer and waits for an acknowledgement. If acknowledgement is received, the timer is reset and next packets are transmitted. But if no acknowledgement is received, the transport layer re-transmits the message and again waits for an acknowledgement. The transmitter will retry to send the message certain number of times and if it fails to get an acknowledgement, it will assume that the receiver is not available and will inform upper layers. In case of fragmentation, the transmitter sends window-sized messages and then waits for an acknowledgement on the last fragment sent. If the timer expires, the transmitter will resend the messages again.

The transport layer also may implement fault detection and recovery. For example, the transport layer at the receiver may request the transmitter to re-transmit selected frames through layer-to-layer messages.

The transport layer may also implement priority for messages. For example, the upper layers may pass the message priority down to this layer and this layer adds the priority to the message header. Header has a two bit fields for message priority and hence there are four priority levels possible in one or more embodiments although any number of bits may be used for priority to implement more levels and this applies to all message partitions and bit numbers described herein. Each priority level has its own queue and depending on message priority, transport layer puts them into respective queues to be processed by other layers. As there are four priority levels in a 2-bit embodiment, there may be a maximum of four priority queues and a minimum of one queue, but the number of priority queue depends on the number of priority levels used.

Figure 12A:
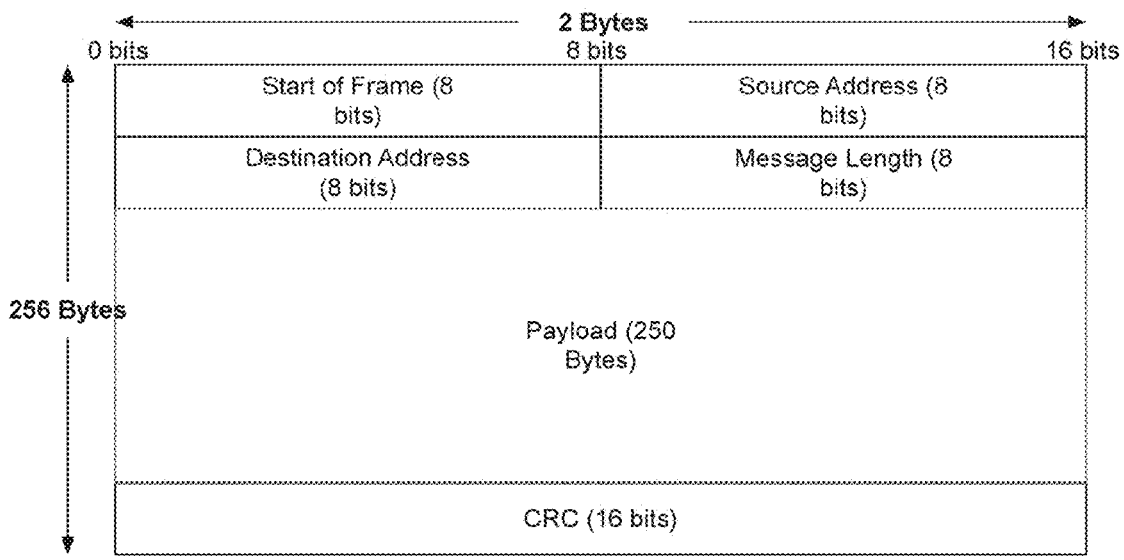

The data link layer is another layer, by way of example and not limitation the bottommost layer, in the communication stack and is responsible for subsystem-to-subsystem delivery of data. This layer completely resides in the kernel space. Data link layer may also be implemented with two sub-layers, for example a Link Layer and Media Access (MAC) layer. The link layer verifies data integrity by calculating/verifying CRC for each outgoing/incoming data frame and also handles any hardware acknowledgements for example. The layer also handles requests for unique logical addresses as well and generates and assigns unique addresses. The MAC layer utilizes driver(s) handling the underlying physical communication channels or bus(es). As the data frames arrive on the buses, the MAC layer copies the received data into a memory pool and passes the pointer to the copied data to Link layer. At least one embodiment supports communication over multiple underlying data transfer technologies or hardware implementations such as serial, CAN, SPI, SDIO, USB, or any other type of communications medium or data bus. This structure along with an exemplary message types in FIGS. 12A-B.

In one or more embodiments, the data link layer is responsible for data integrity, for example through the use of CRC checking or any other type data integrity coding or format desired. Embodiments of the data link layer are also responsible for logical address assignment. For example, this layer is responsible for assigning and managing logical addresses of modules in a device. All the modules like Pump Motor Controller, Power Supply Controller, Communication Engine, User Interface Controller, etc., have a unique ID so that they can be uniquely identified in a pump. The protocol stack can support 254 modules as the address field is 1 Byte field and logical addresses 00, 01, and FF are reserved addresses. If modules are identified according to their unique hardware address (MAC addresses), and as the hardware addresses are more than a Byte in size, this would add overhead to the protocol. To avoid this, each module may be assigned a logical address between 1 to 255 and this layer then maintains the assigned addresses. The application layer does not need to know what the hardware address is or what the logical address is in general, which simplifies logical and API calls.

One of the modules is generally assigned with the task of generating unique logical addresses for other modules in the device, no matter if those modules are connected directly to this special module or not. When the device powers on, all the modules power on as programmed. The module responsible for generating address for devices is called the "root" device. The root device is aware of its special role and assigns itself a logical address of 01. As other modules wake up, they assume their logical address as 00. They know that 00 is not a valid address but also know that there exists a module with address 01 who can provide a unique address to them.

Hence, these modules send address requests to a destination with address 01. On receipt of this message, the root module checks its internal table to verify if the requesting hardware already has a logical address assigned. If a logical address is assigned, the root module sends that same logical address in response; else it generates a unique logical address, updates this address in its internal table against the requester's MAC address and sends this address in response. On receipt of an Address Response, the requester module starts communicating with this logical address.

A module in one or more embodiments may not communicate without a valid logical address. If multiple modules try to request for a logical address, there will be collisions. Due to collisions, no requests ever reach the root module, and thus none of the modules receives a logical address. In this scenario, other modules will retry after a random period of time. Depending on the criticality of device, the amount of random time can be varied, i.e. critical devices may wait for lesser period of time before a retry. The amount of wait time may be part of configuration and the devices may wait with reference to their internal clock for example.

If a device does not desire to use the dynamic addressing mechanism, each module may be programmed with a unique address, for example to implement a static versus dynamic address assignment scheme. Embodiments may still utilize a root module that maintains the addresses of the connected modules.

Embodiments of the data link layer may also implement routing. As mentioned, a module may have multiple bus types or topologies and there may be different type of devices connected on various buses. If a Data Link layer receives a packet that is not addressed to it, it first checks if it has multiple bus architectures and if true, it forwards the message to other buses; else it simply discards the packet.

This kind of addressing mechanism is well suited for star topology for example. Hence if PMC1 wants to send data to PMC2 but there is no direct data path, then it will re-route it through the root module. In this case, the root module can broadcast the message in the network or perform a lookup in its internal table and just forward the packet on a specific line. Hence, in one or more embodiments that implement routing, each module that supports multiple communication buses may maintain a list of all devices directly connected to the module so that they can efficiently route the packets. As stack supports data routing, it seamlessly bridges multiple heterogeneous data buses, thus making communication, bus topology independent. Few examples of possible bus topologies include Ring, Star, Mesh, and Tree topologies or any other topology that may be utilized to transfer data.

Figure 3:
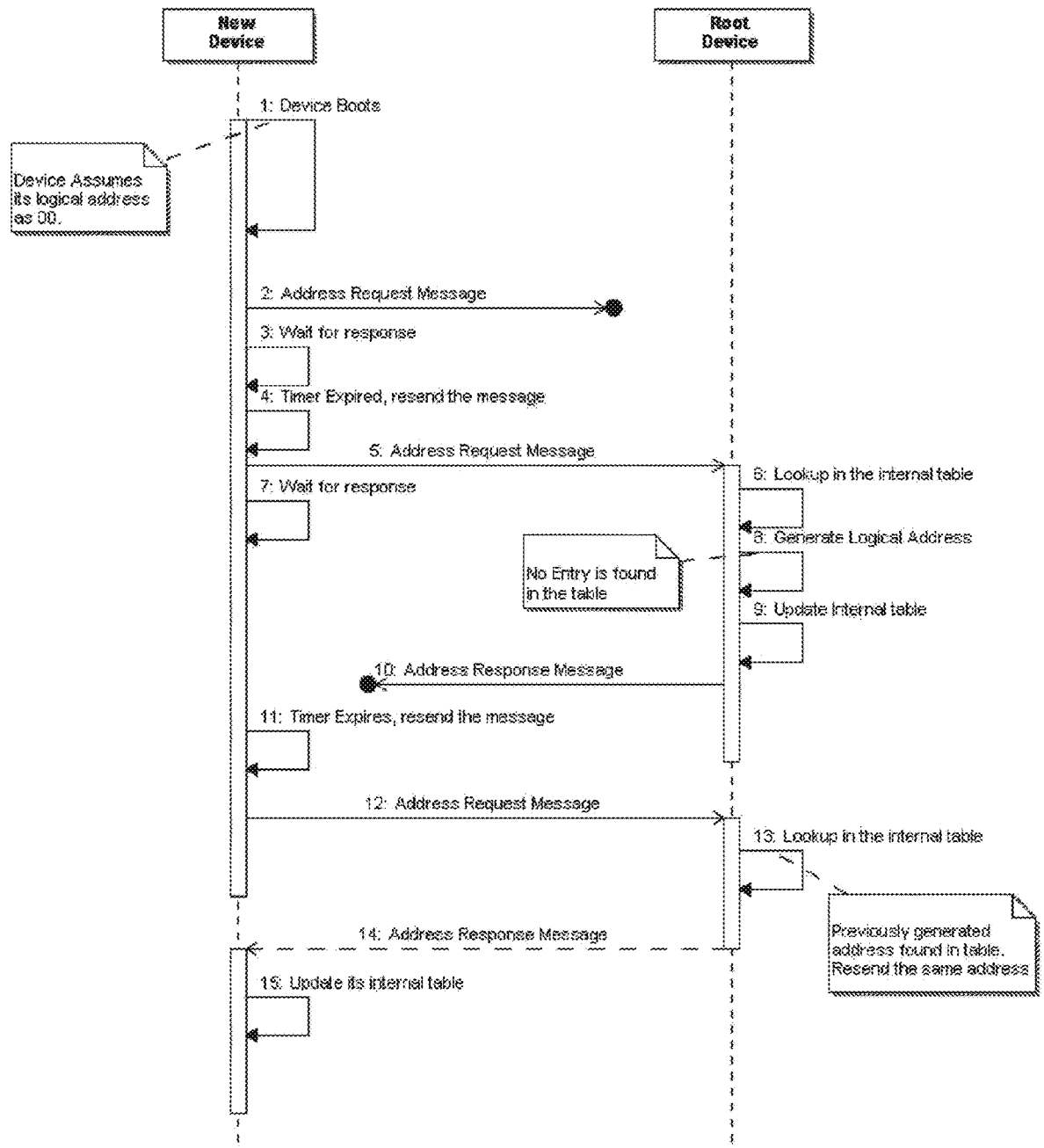
FIG. 3 illustrates an embodiment of an address request method implemented within the manager layer.

FIG. 3 illustrates an embodiment of an address request method implemented within the manager layer. As shown, when a device is added to the system, for example hot-swapped in, the device boots and requests an address from the root device. The new device waits for a response and if a timeout occurs, requests an address again. Once the root device receives the address request message, it looks up an available device number and generates a logical address for the new device and updates the table. Alternatively, if there are no available numbers left a NAK with appropriate error message may be returned to the new device. The root device returns the new device logical address to the new device in an address response message. Any further requests for the address are handled by lookup via the root device. The new device stores the logical address in a local table for further use. This capability generally does not exist in medical devices or infusion pumps since the configurations are generally assumed to be fixed, using a fixed operating system and fixed bus without regard to potential new devices and new types of devices that may communicate with a root device.

Figure 4:
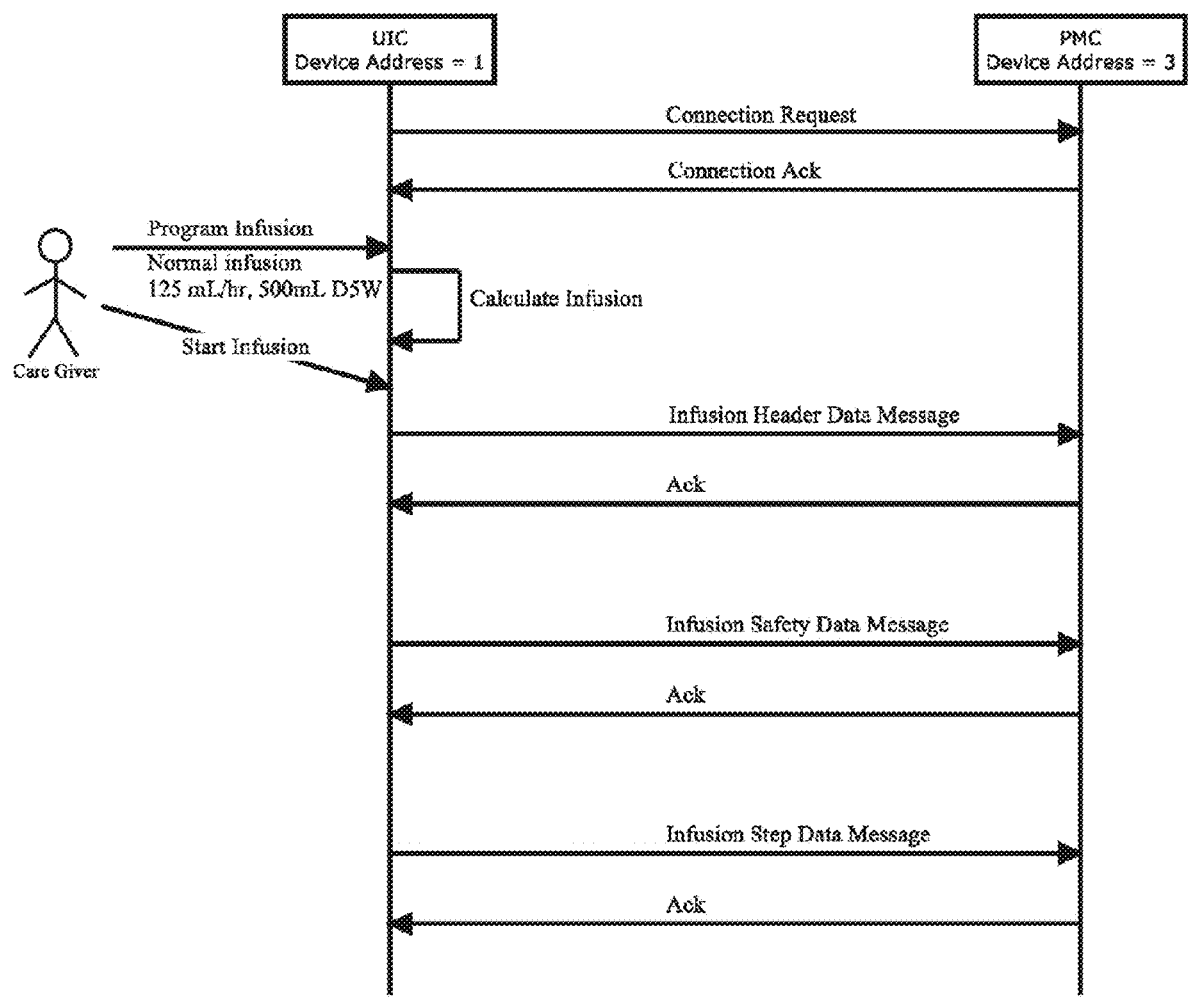
FIG. 4 illustrates an embodiment of a simple infusion sequence utilizing various messages provided by embodiments of the method.

FIG. 4 illustrates an embodiment of a simple infusion sequence utilizing various messages provided by embodiments of the method. Once the address of a new device is obtained, it may communicate with the other components within the system. The figure shows user interface controller UIC having device number 1, initially connecting to a drug infusion pump having device number 3, wherein the logical addresses of the devices, or device numbers are obtained as shown in FIG. 3. The UIC accepts input from a Care Giver that indicates an infusion is to take place. The UIC application calculates the necessary steps to achieve the infusion and sends an infusion header and data message to the drug infusion pump, which acknowledges the message. The UIC then sends an infusion safety data message, which is acknowledged and after the infusion is complete, the UIC sends an infusion stop data message, which is acknowledged. This scenario is a typical scenario that enables any type of drug infusion pump to be added to a system and utilized, for example in a hot swap scenario where an infusion pump may return an error or a different type of drug infusion pump is to be added to the system and utilized for example.

Figure 5:
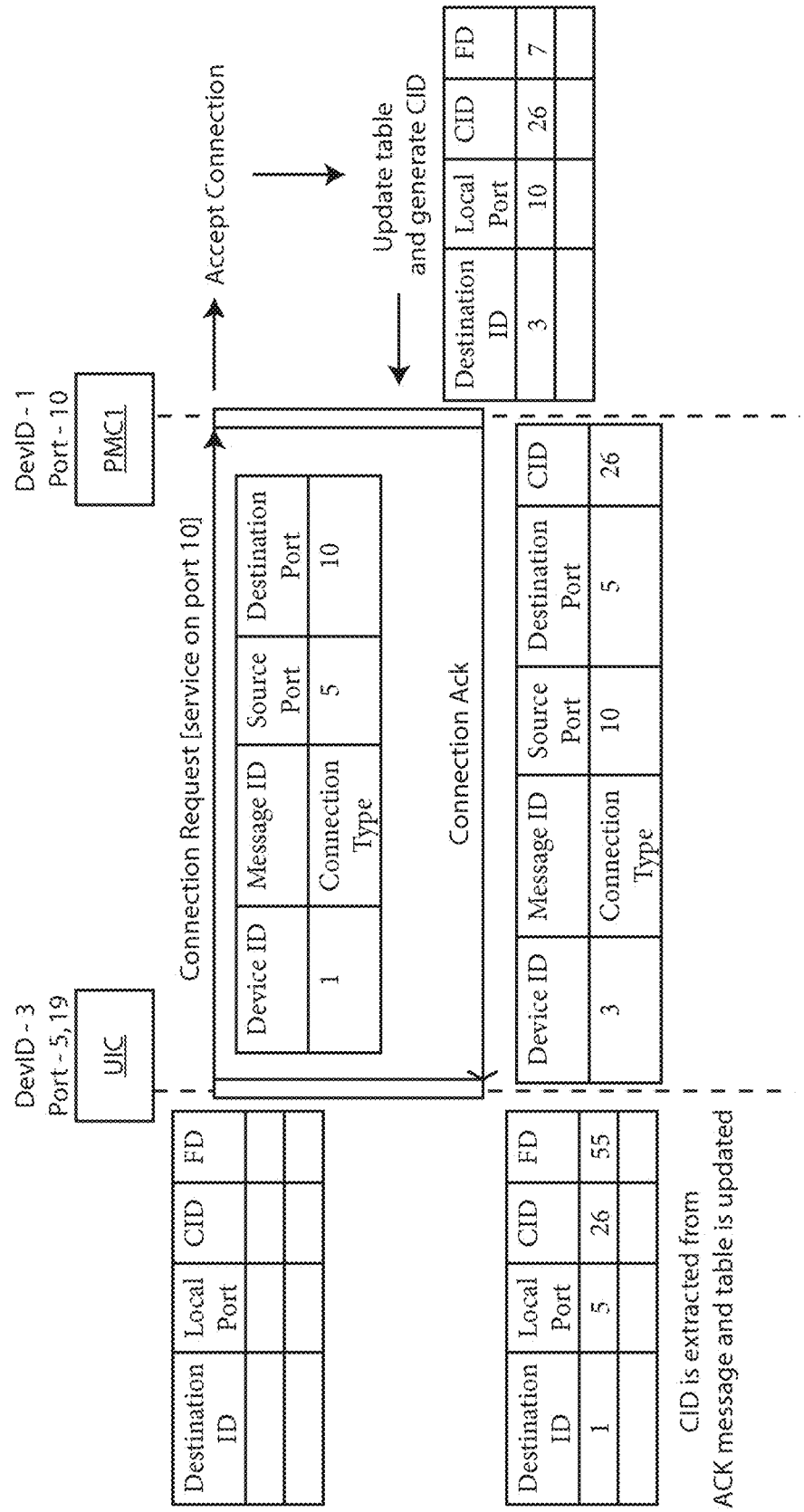
FIG. 5 illustrates an embodiment of a connection method implemented within the session layer.

FIG. 5 illustrates an embodiment of a connection method implemented within the session layer. In the scenario shown, the UIC requests a connection in order to communicate with the PMC to command the PMC and/or for example obtain status updates. In this case, PMC acts as a service provider as the PMC is providing status updates on a known port. UIC sends a connection request to PMC on that port, e.g., port 10, shown as a message passing from left to right. After receipt of the connection request, the PMC accepts the request, generates a unique CID, e.g., 26 for this communication and updates its internal table. The PMC sends the generated CID back to UIC as a part of connection accept message, shown traveling from right to left. On receipt of connection accept message from the PMC, the UIC extracts the CID from the message and updates its internal CID table as shown in the lower left. The UIC then sends an acknowledgement message to the PMC to confirm the successful receipt of CID. If the PMC is not able to process the request from UIC and hence cannot establish communication, the PMC sends a connection reject message to the UIC. On receipt of connection reject message, the UIC may retry to obtain a connection. See also FIGS. 10A-D, 11A-B and 12A-B for an embodiment of the exemplary message structures that may be utilized to form an implementation of various layers, which are described further in detail below.

Figure 6:
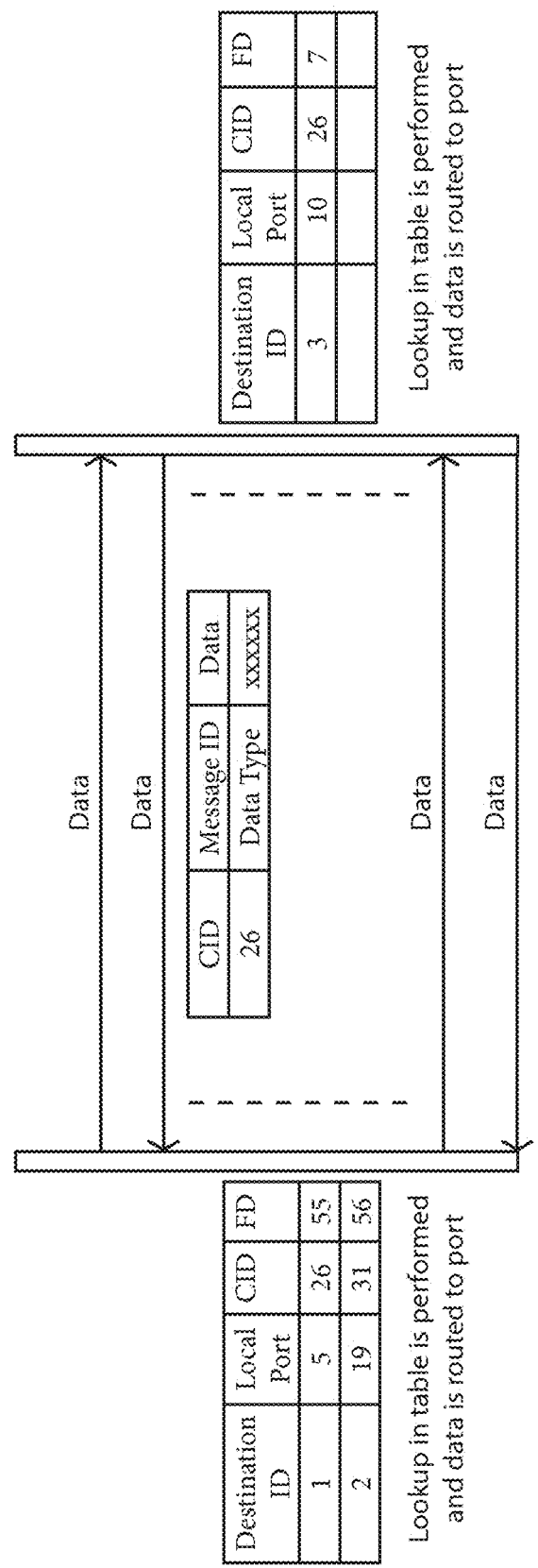
FIG. 6 illustrates an embodiment of a data exchange method implemented within the session layer.

FIG. 6 illustrates an embodiment of a data exchange method implemented within the session layer. Once the PMC receives acknowledgement from the UIC, the connection process is complete. At this time, both devices may exchange data using the agreed CID. When the session layer of PMC receives any data from the UIC with a valid CID, it performs a lookup in its internal table against the 'Destination ID' and 'CID' to resolve the port number where the packet is to be forwarded.

Figure 7:
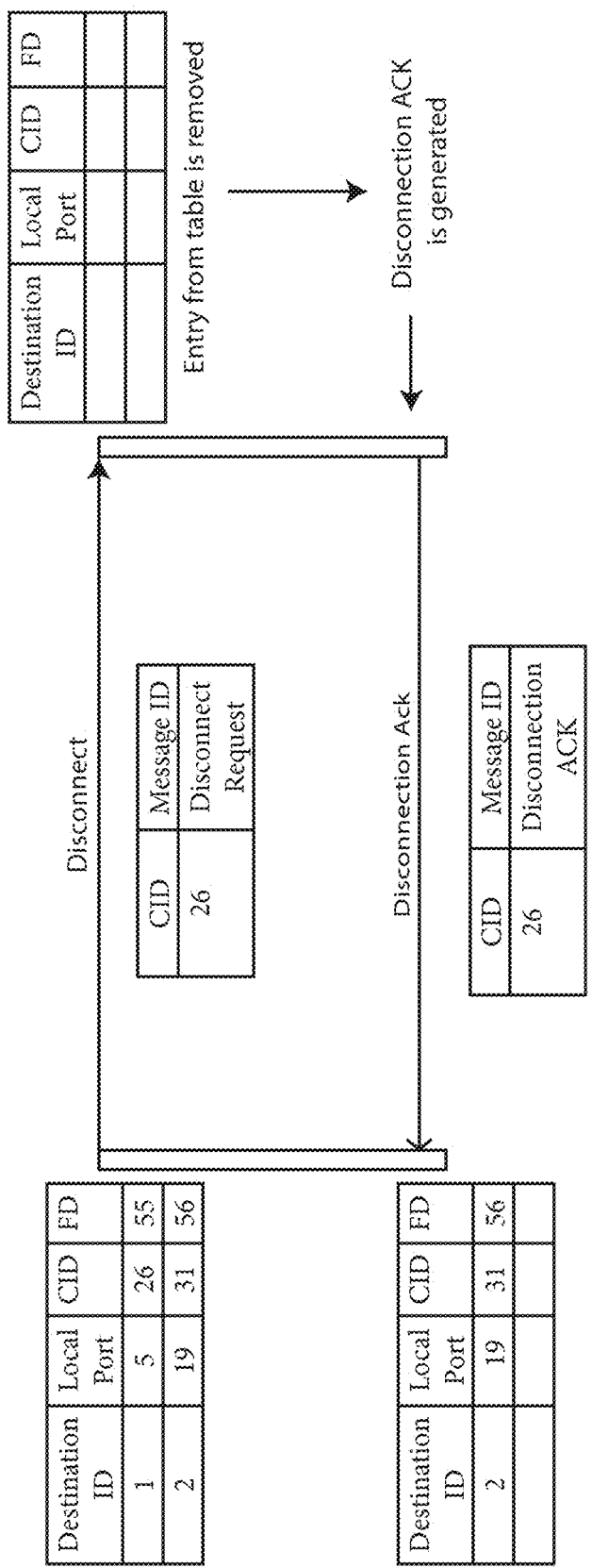
FIG. 7 illustrates an embodiment of a disconnection request method implemented within the session layer.

FIG. 7 illustrates an embodiment of a disconnection request method implemented within the session layer. On completion of data transmission, either of the communicating parties may request for a connection termination. As shown, the UIC initiates the process of connection termination. It sends a disconnect request to PMC with the respective CID. The PMC processes the request and if there is no active communication, the PMC will send an acknowledgement to the UIC and delete the CID entry from its table. On receipt of disconnection acknowledgement from PMC, the UIC also removes the CID entries from its table.

Although the general session layer communication protocol has been described above, a more in-depth description of the Session layer messages follows, according to one or more embodiments of the invention. The message structures utilized in one or more embodiments of the invention as described below are shown in FIGS. 10B-D.

Connection Request Message

For a connection-oriented communication session, when an application opens a socket to communicate over a port on some other device, a handshake is performed before the communication starts. The handshake begins with a connection request type message to the service provider. The "layer flag" is set for this message type. Therefore, the request packet is consumed by the session layer. The connection type may be initially set to "Unknown" suggesting that the data packet is neither connection-oriented nor connectionless. The message type is set to "Connection" as the command is used to establish new connection. The message is a request for establishing new connection; hence "Command" field has "Connection Request" set. The application requesting a connection specifies the destination's port address and also provides its own port address, hence the connection request packet has source and destination port address.

Connect Accept Message

On receipt of a connection request message, if the service provider has enough resource, it responds with a connection accept type of message. The service provider generates a CID for the communication and sends it to the requester as a part of this message. As the connection requesting entity has no information of the generated CID, the service provider sends source and destination port address as a part of this message to let the other end know about the generated CID.

Connection Acknowledgement Message

On receipt of a connection accept message, the requesting end updates its internal table with the received CID. In response to connection accept message, the requesting end sends an acknowledgement message to indicate the service provider about the receipt of CID and complete the handshake. It is possible that multiple applications on one module request to communicate with one application on another module on the same port number, e.g., many-to-one. To inform the service provider about the particular application that is sending an acknowledgement, "source port" is added to the acknowledgement message.

Connection Disconnect Message

Once the communication is completed, any one of the participating entities may request a connection disconnect for a graceful termination of the connection.

Connection Disconnect Acknowledgement Message

This message is sent as an acknowledgement on receipt of a disconnect message. The message is intended to ensure that a communication is not terminated if an active connection still exists. If a disconnection acknowledgement is not received within a certain time period, a disconnection attempt may be made again.

Connection Reject Message

If the service provider cannot accept any new connections, it sends a connection reject in response to a connection request message. In the connection reject message, it sends the reason for rejecting the request. On receipt of a connection reject message, the requester may retry after some time for example.

CID Info Request Message

Any participant involved in communication can request for status of CID. This message acts as a ping message to verify if the destination port is open and CID is an active CID.

CID Info Response Message

On receipt of a CID Info request, a CID Info Response is transmitted. This message contains the source and destination port addresses involved in communication, window size for transmission, etc., and also indicates if the CID is active or not.

Socket Status Request Message

This message is utilized to request socket related information such as the type of socket, purpose of opening this socket, etc.

Socket Status Response Message

This message is sent in response to Socket Status Request message. The message contains socket related information such as the type of socket, purpose of opening this socket etc.

Subscribe to Service Message

The communication protocol enables applications to provide a service, e.g. a broadcast service. For example, the PMC may have a service running that broadcasts PMC status periodically on a known port. If the UIC requests the PMC status, it may simply subscribe to this service with the PMC and receive the messages. Typically these services are one-way communication.

Subscribe to Service Acknowledgement Message

Once the service provider receives a subscription request, it has to provide a CID to the requester. The CID is delivered through an acknowledgement message.

Unsubscribe from Service Message

If a subscribed application no longer desires to be subscribed to a service, it may request to unsubscribe. On receipt of an unsubscribe service message, the service provider removes the entries from its internal CID table and sends an acknowledgement to the requester. If the service provider finds that there is no one subscribed to a service, it may decide to stop the broadcast service until it has at least one subscribed application.

Unsubscribe from Service Acknowledgement Message

On receipt of this message the application requesting to unsubscribe, removes entries of CID from its internal table and releases the involved sockets and ports.

Device Address Request Message

An application may request a logical address for a device using this message.

Device Address Response Message

On receipt of an "Address Request" message, a device sends its address as a part of the response message. Alternatively, a Device Address Response Message may be sent independently at anytime and may not necessarily be tied to a request message.

Device Type Request Message

This message is used to request name of a device. Every connected device has a unique address but may have non-unique names or no names. Device types can be PMC, CE, UIC, etc.

Device Type Response

This message is generally sent in response to "Device Type Request" message and contains the type of the device sending this message. Alternatively, a Device Type Response Message may be sent independently at anytime and may not necessarily be tied to a request message.

Connection-Oriented Data Message

At least one embodiment of the session layer adds just two bytes of header information when sending data between devices. The CID is generated and exchanged during the handshake process prior to data transfer.

Connectionless Data Message

Connectionless data transfer is used when no handshake is required to transfer data. As there is no handshake, there is no CID generated for the communication and hence both source and destination port numbers are utilized to ensure the delivery of data.

FIGS. 11A-B and 12A-B illustrate corresponding message structures for exemplary embodiments of the Transport layer and Data Link layer respectively and are described further below.

Figure 8:
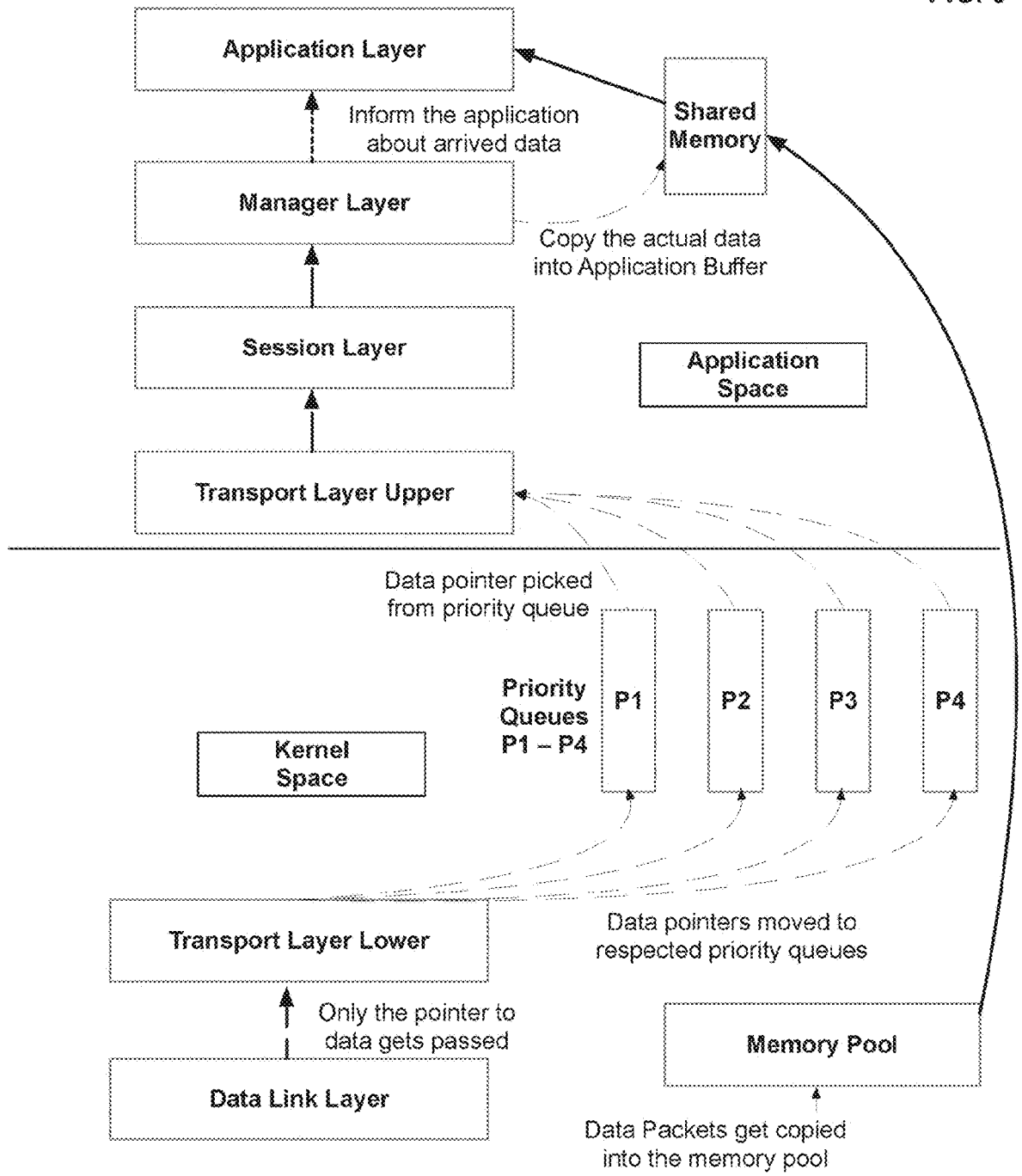
FIG. 8 illustrates a layer flow diagram that shows the flow of data within the various layers implemented in at least one embodiment of the invention.

FIG. 8 illustrates a layer flow diagram that shows the flow of data within the various layers implemented in at least one embodiment of the invention. Specifically, data flow up the protocol stack for incoming data is shown. The destination application buffer location is not known until the data frame moves up to manager layer. Hence, the fragment is stored in a memory pool until it reaches manager layer and once the target application is resolved, the data is copied from the memory pool into application buffer. In one or more embodiments, memory utilization may be minimized by returning a buffer to memory if the buffer is over a predefined age threshold.

Data Link Layer

Data Link layer controls one or more physical communications links, data buses. The layer filters the messages directed to the specific device and ignores other messages. The layer may compute a CRC on the received packet and verify it with the received CRC. Valid data frames are copied into a memory pool and pointer to these messages are forwarded to the transport layer.

The transport lower layer and data link layer run as an independent service and stores data in the designated priority queue, P1, P2, P3 or P4. The transport upper layer, session and manager layers execute in the application space, and the transport upper layer maintains pointers to the priority queues and Communication ID tables. In one or more embodiments, the memory pool, priority queues and CID tables are in shared memory space.

In one or more embodiments, the data link layer is further divided into two sub-layers, a link layer and a MAC layer. The MAC layer may interface with bus drivers and has a buffer for each underlying bus. As the data arrives on these buses, the data is copied into these buffers and then forwarded to link layer. The buffer may be implemented as a pair of buffers, while one buffer is used for receiving new data, other buffer is used to transfer previously received data.

The link layer copies the data from buffers into the memory pool. The memory pool is a contiguous memory block and each memory block may be implemented as a factor of frame length. As the application consumes data, the data is removed from the memory pool to make room for new data packets. As the application consumes data randomly, there may be memory holes in the memory pool. Hence, the link layer generally maintains a list of available memory locations in the memory pool. When memory is freed from the memory pool, the pointer to available location is added at the end of this list. When a new packet arrives, it is placed at the memory pointed by the first element in this list. If there is no element in the list, memory pool will be considered full and the packets will be dropped. In one or more embodiments of the invention a memory manager may be utilized to control access to memory from the various layers, including concurrent access control of memory from the various layers. Embodiments of the invention may minimize or altogether avoid multiple copying operations by maintaining one copy of data in the memory pool while passing pointers to the memory as the data moves up and down the stack. By controlling access to the memory during access, semaphores may be utilized to ensure data integrity while allowing multiple processes to effectively utilize the data in a concurrent manner. Avoiding multiple copy operations enables minimal memory utilization in embedded environments and minimizes processor utilization as well.

As the transmitter has tendencies to push data on buses, they can soon over-utilize the bus by transmitting too much data. The bus driver at the MAC layer in one or more embodiments may be implemented to handle such scenarios.

Transport Layer

In one or more embodiments, the transport layer may be divided into two sub-layers, a transport upper and a transport lower layer. The transport upper layer resides in application space whereas the transport lower layer resides in kernel space. These two layers together handle transport layer functionalities.

The transport layer is implemented in one or more embodiments to reassemble fragmented data and also to resolve data priority. When a new data packet is received by transport lower layer, a timer may be started for the data. If the data is not consumed before the timer expires, the data may be discarded and the memory freed from the memory pool. This avoids memory starvation if no application exists to consume received data. If the acknowledgement field was set, the transport layer sends a NAK, "timed out in priority queue" error code, for example.

The transport layer header has an acknowledgement flag and if the flag is set, the receiving transport layer will have to send some kind of acknowledgement for the received data fragment. If fragmented data is received, the acknowledgement is sent after receiving window size amount of data or a complete message. This flag is set for a connection-oriented data transfer to ensure delivery of data. This flag may also be set in a connectionless data transfer only if data fragmentation is utilized.

Fragmented Data Packet Handling

In case of fragmented data, before the transmitter starts sending any data fragments, the transport upper layer at the transmitter first requests a window size from the receiver. The window size may be exchanged once during first data transfer or may be obtained before every data transfer. Window size is the number of data fragments that can be sent before an acknowledgement can be expected. When receiver receives a window size request, transport upper layer at receivers end, computes the amount of free memory in application buffer and sends the response as window size in the 'window size response' message.

In one or more embodiments, the transport upper layer at the transmitter side initializes a data structure for the CID that requested a window size. In this structure, the transport layer stores the CID, last reported window size, last successfully received fragment number and the maximum allowed time period between two fragments, etc. Also, the transport upper layer at the receiver maintains same structure. The transport layer expects that the fragments will be sequentially numbered starting from 1 in one or more embodiments.

As the transmitter receives a window message, it calculates the number of fragments to be transmitted before expecting an acknowledgement. The transmitter starts sending data fragments in sequence starting from fragment number 1 for example.

When the receiver receives first fragment, the transport lower layer starts a timer on the received data frame and places the fragment it into the respective priority queue. The transport upper layer updates the structure and stores the sequence number of the fragment. If the fragment is delivered to the application buffer by upper layers, the upper layers inform the transport upper layer about the success. The transport upper layer updates its structure with the first fragment being delivered. Upper layers do not inform application about the available fragment until all the fragments constituting to a message are received. An application buffer is used for re-assembly of fragments to minimize memory footprint.

If the transport upper layer receives all the fragments for a window successfully, it waits for all the fragments to be delivered to application buffer successfully. Once all the fragments are sent to application buffer, the received fragment number and delivered fragment number match and the transport upper layer sends an acknowledgement for the last fragment in the sequence. The transmitter receives the acknowledgement at the transport upper layer.

Ideally, the transport layer accumulates all fragments, verifies that they are in sequence and merges them into one complete message before sending it up the stack. However, in one or more embodiments, the transport upper layer forwards the frames to the session layer as they are received, but ensures that the fragments are delivered in sequence. This optional implementation may be utilized to lower memory utilization. This is the case since the message does not have to be reconstructed in full within the stack until the full message is received in the application. As the fragment number in the transport header is 10 bits wide in one or more embodiments, the layer can support a maximum of 1023 fragments (fragment number 0 is reserved and represents a non fragment data frame) before the fragment numbering overflow. As each fragment has a maximum of 248 Bytes payload, hence a total of 253,704 Bytes is required at the receiver end for each active connection to accommodate all the fragments. Any other size of fragment number field may be utilized to increase the overall size as one skilled in the art will recognize.

At the receiver, as the fragments are received, transport upper layer updates the last fragment number in its structure. Before updating, it verifies that the received fragment is in sequence with previously received fragment. If it detects a missing fragment, the layer still forwards the fragments up the stack, but in their respective token puts an offset value. Metadata along with a pointer to the received data fragment is called a token. This offset value is used by manager layer to provide a gap while accommodating other fragments around the missing one, so that the gap can be filled once the missing fragment is received. For example to create an empty space in memory so that when the missing frame is finally received, it will be accommodated in this empty space to complete the final message. Meanwhile, transport upper layer waits for the fragments to arrive and then looks for any missing fragment in the sequence. Once the layer generates a list of all missing fragments, it requests for retransmission of fragments from the transmitter. Once the missing fragments are received, they are forwarded to upper layers so that they can be used for filling the empty spaces in final message.

When retransmission is required, transport upper layer at receiver end, sends retransmission request message with the desired fragment number in it. The receiving end maintains a list of missing fragments and as the missing fragments are received, their entry is removed from this list.

If the transmitter retransmits an already transmitted fragment, the receiver compares the fragment number with last received fragment number and will detect that there has been a retransmission. The layer checks if the retransmission was requested by the receiver explicitly or not. If the retransmission was intentional, the fragment is consumed else the fragment is dropped assuming a false retransmission of data.

Once the transmitter sends one window size worth of fragments, it starts a timer and waits for an acknowledgement on the last fragment in the sequence. The transmitter may send any further fragments only when it receives an acknowledgement. If the acknowledgement is delayed and the timer expires, the transmitter may send a "window size" request message before retransmitting the fragments. A receiver may fail to send an acknowledgement if the receiver is too busy or its buffers are full. Hence, a "window size" message is sent because it serves two purposes, the first being that a response to this message implies that the receiver is ready for accepting messages, and the second being that the new responded window size buffer is available at receiver so that chances of getting an acknowledgement increases.

In case of missing fragments, the receiver sends a retransmission request instead of an acknowledgement. A retransmission request can only be sent if the last fragment in the sequence was either received successfully or was found missing. Hence, the transmitter considers a retransmission request message as an implied acknowledgement and no more waits for an explicit acknowledgement, but may wait on acknowledgement for retransmitted fragment.

Missing fragments can be of three types, the first fragment missing, any fragment(s) missing between first and the last fragment of a complete message, and the last fragment itself missing. If the first fragment is missing and the receiver starts receiving from fragment number 2, it accumulates all the messages till it receives window size messages and explicitly requests for the 1st fragment. The same technique is used for requesting any missing fragment between 1st and last fragment.

Missing the last fragment of a complete message may be a complicated scenario because transmitter never informs the receiver about total number of fragments needed to send a message and hence, there is no way for receiver to know when the message completes. Missing "last" fragments can be of two types, missing the last fragment from a window and missing the last fragment of a message. In the case of missing the last fragment from a window, it is easy to detect. Every time a fragment is received, the receiver starts a timer and waits for next fragment to be receive before the timer expires. The transmitter sends the last message for the window and waits for an acknowledgement. If this message is lost, the receiver waits for this last fragment to arrive. The timer at the receiver expires earlier than the timer at the transmitter. As the receiver keeps track of fragment sequences and window size, it realizes that the last fragment was not received on time and hence sends a retransmission request for the last fragment.

A more difficult problem occurs when the last fragment of a message is lost. As the receiver has no idea about how many fragments will constitute a message, it looks for the fragment with 'last fragment' flag set. This fragment indicates the receiver that it was the last fragment from the message. If this fragment is lost, the receiver has no idea when to stop reassembling fragments. To ensure delivery of this last fragment, the transmitter can use following two approaches.

In the first approach, the transmitter knows that the last fragment is approaching. It explicitly reduces the window size to make sure that the last fragment of the message becomes the last fragment of the window as well. As the receiver can detect the last fragment from a window, if the last fragment from a message is lost, the receiver may request retransmission.

In the second approach, the transmitter will send the last fragment with 'last fragment' flag set, followed by few fragments with random payload but with incremental fragment number. If the last fragment of the message is missing, the receiver will detect the missing fragment as there will be gap in sequence numbers and will request for retransmission. When the receiver attempts to arrange the fragments in sequence, it detects the fragment with 'last fragment' flag set and hence discards all fragments following this fragment.

Non-Fragmented Data Packet Handling

For a non-fragmented data frame, it is first received by transport lower layer, which starts a lifetime timer on this frame and puts the frame in appropriate priority queue. The frame is picked from the priority queue by transport upper layer, which forwards it to other layers, for example Session layer.

Session Layer

Session layer major responsibilities are to ensure application-to-application delivery of data and generate unique CID's within a system. The stack works on the principle of service provider and service consumer. The application providing service generates unique CID's for the engaged participants. The CID is unique within the system running the service provider application in one or more embodiments. The CID may be thought of as a key used to hide the information about source and destination ports engaged in communication.

The session layer may be implemented in a lightweight or a very thin layer to a connectionless communication because a connectionless data packet will contain the source and destination port addresses as part of their headers and hence does not utilize a CID.

Packets reaching the session layer may be divided into two categories, namely data and control. Further, the incoming data can be connection-oriented or connectionless and fragmented or non-fragmented.

Connection-Oriented Data Transfer

Connection-oriented data transfer makes use of a connection through a handshake process. After an initial handshake process is complete as is described further below, data exchange occurs. In connection-oriented data transfer, embodiments of the invention utilize a data header with an acknowledgement flag set and connection type set to 01, for example. Data being exchanged may be fragmented or non-fragmented based on the size of the data and the underlying packet size supported by the physical medium.

Fragmented Data

When an application writes to a virtual port, the session layer adds a session layer header to the data and forwards it down the stack. In one or more embodiments, the session layer header is 2 bytes wide. Hence, if fragmentation is needed at the transport layer, the first fragment is set to contain the CID from the session layer while the rest of the fragments may contain only application data. The session layer at the receiving end forwards the first fragment that contains the session layer header, but is unsure as to where to forward other fragments from the sequence as there is no CID information in subsequent headers. Also, if two or more applications on one device want to send data to one device, it is not possible without further information in general at the receiving end to aggregate fragmented data because there is no way to uniquely identify which application is sending what data fragment. To resolve this issue, the transport layer copies session layer header to all the related fragments. As all the fragments will now contain CID, they can be uniquely identified at the receiving end.

The session layer header contains an acknowledgement flag that is utilized in the case of complete messages. As the session layer ensures application-to-application delivery of data, it sets the acknowledgement flag for the receiver to acknowledge successful delivery of data. As the header is copied in each fragment, the session layer will look at the flag and will acknowledge the transmitter every time a fragment is delivered which is not what acknowledgements are generally for, i.e., a complete message acknowledgement.

To avoid this issue, the transport upper layer at the receiver end appends metadata to packets as they are sent up the stack. Metadata along with pointer to received data fragment is called a token and instead of passing data, transport layer passes a token to session layer. In the case of exceptions in behavior of the session layer, metadata provides guidelines for the session layer to follow. For example, the session layer will not send any acknowledgements for data fragments, and when the transport upper layer receives a fragment with a "last fragment" flag set, it updates the metadata so that session layer knows that it needs to send an acknowledgement to the transmitter regarding the receipt of a complete message.

Flow of Control

As the fragments move through the session layer, session layer extracts the CID from the fragments, performs a lookup in the Communication ID table based on CID and the sources logical address obtained from the metadata. The session layer determines the associated file descriptor source and destination ports for the CID. Once the file descriptor is known, it removes all the headers and modifies the metadata to communicate the file descriptor detail to manager layer.

Once the fragment arrives at the manager layer, the manager layer extracts the file descriptor information from metadata and forwards the fragment to respective application. Before the manager layer forwards the message to the application, it determines if the file descriptor is still in use and in the state of accepting data. If conditions are favorable, the message is copied into the application buffer and a "message received" flag in file descriptor is set. If the current operation on the file descriptor is a blocking read, the read function call returns with number of bytes available in application buffer. If the current operation is a non blocking call, the application either checks the flag and if set, reads data from buffer, or the manager layer may make an asynchronous function call on receiving data.

After delivering the data to the application, the manager layer returns the token to session layer. This token contains information about the state of the previously passed message. Depending on the state of token, the session layer performs activities such as sending a session-to-session layer acknowledgement.

If the data is fragmented, session layer further modifies this token and sends it down to transport layer, otherwise the session layer consumes the token. The transport layer determines if the fragments were delivered in sequence they were sent and accordingly controls acknowledgements and window sizes.

Non-Fragmented Data

If a message size is less than the Maximum Transmission Unit (MTU), no fragmentation is required and the complete message is sent in one frame. As the frame moves up the stack, transport upper layer adds very little information to the metadata as complete information for the session layer is already available in the frames header. The session layer reads the header and extracts the data type. If the data type is connection-oriented data, the session layer extracts the CID and performs a lookup in the CID table to determine source and destination ports. The session layer removes all the headers from the datagram, updates the metadata with the destination file descriptor, and forwards it to the manager layer.

Connectionless Data Transfer

As mentioned above, in a connectionless data transfer, the session layer may be implemented in a lightweight or very thin layer. As connectionless data transfer does not utilize a handshake, no CID is generated. Due to the absence of the CID, the protocol header utilizes source and destination port addresses. The session layer reads the destination port address and determines the associated file descriptor and forwards the message to that port. As connectionless data transmission does not guarantee delivery of data, the acknowledgement flag on the frames is set to false.

If a connectionless data frame is larger than the MTU, the transport upper layer fragments the data into manageable sizes without setting the transport layer acknowledgement flag as would be done in connection based communications. During reassembly, if transport layer sees any missing fragments, it discards the complete message. Through a token, the transport layer informs upper layers to discard previously accumulated fragments in application buffer.

Manager Layer

Manager layer handles file descriptors and forwards packets from lower layers to appropriate file handlers. The manager layer also performs the copying of data from the memory pool into the application buffer. The manager layer knows the size of the application buffer and the application buffer size may be smaller than one frame length.

If the application buffer is large enough, the manager layer copies the complete message into application buffer. If the application buffer is not large enough, the manager layer copies data in a sequential manner. The manager layer fills the application buffer with data and waits for the application to read the data before copying the next portion of data. Once data is successfully delivered to the application, depending on the token, the manager layer informs the session layer regarding success.

Control Flow Up the Stack

The flow of control is now described as data moves up the stack from the lowest layer to the application layer.

Data Link Layer

The data link layer control is described with respect to the two sub-layers that make up the data link layer, namely the link layer and the MAC layer. The MAC layer controls the physical bus drivers.

MAC Layer

As the datagram arrives on the physical bus, the bus driver copies the datagram into a buffer. Once the complete datagram is available in the buffer, the MAC layer calls an API in Link Layer to copy the available data into the memory pool.

The link layer API returns a value to indicate the outcome of the copy operation. The operation may succeed or fail. The returned error code provides the reason for any failure. The MAC layer waits for the API to finish the operation before storing newly available data into the buffer.

Link Layer

As discussed in the sections above, the memory pool may be fragmented due to applications consuming data at random rates, resulting in holes in the memory pool. In one or more embodiments, the link layer maintains a link list, or a doubly link list, or bit map or any other data structure capable of storing available memory locations in the memory pool. When a memory location is made available, a pointer to the memory location is added to the tail of the list. When a new datagram is available, it gets copied at the memory pointed by pointer in the head of the list. Though the received message can be of any size and wherein a maximum size exists, for example 256 bytes, the size of the memory pool is selected to be an integral multiple of the maximum datagram size. This simplifies memory management, as the stack is aware of the size of allocated memory given the pointer to that memory. There may be instances when a datagram is available at the time when memory is made available in the memory pool. In this case, both the copy and the delete processes will try to access the list simultaneously leading to concurrency issues. In one or more embodiments, the memory pool may include non-uniform size buffers for a more flexible buffer implementation at the cost of memory management complexity as one skilled in the art will recognize.

When the MAC layer calls an API to copy the data from hardware buffer to memory pool, the API first checks the list for any available memory location in the pool. If memory is available, the API copies the datagram to the memory location pointed by the head of the list and deletes the pointer from the list. If no space is available, for example the link list is empty, or error occurs during the copying to memory pool, the API returns respective error code.

After successfully copying the datagram, the API adds the pointer to the datagram in a list with a number of timer ticks remaining before the data should be delivered to application. This API may be reentrant as the MAC layer may be riding over multiple bus architectures and the data may be available in multiple buffers at the same time resulting in calling this API while the layer is still servicing the previous call.

The protocol stack may be implemented with a time limit within which a datagram is to be used by an application, or else the datagram is dropped from the memory pool. To enable this feature, embodiments may implement a global list containing pointers to each datagram with the timer count on each pointer. As the new packets arrive, an API adds the pointer to this packet at the end of this list. The API adds "time to live" value to the current timer count and generates a timer count that represents an expiration time for the packets. When timer count changes, an API looks at the timer count starting from top most element in the list and starts deleting datagram if their timer counts are less than or equal to current timer count.

Once the data is consumed by the application or the data times out, an API is called to remove the datagram from the memory pool and add the pointer to the available memory list. This API may be reentrant as the data may expire at the same time it was consumed by the application. Both processes may attempt to delete the same datagram, therefore semaphores/locks may be utilized to effectively serialize control.

When data gets copied to memory pool, the link layer generates a token for the packet. The token contains the pointer to the datagram and length of the datagram. This token is forwarded to the transport layer through a transport layer API for further processing.

Transport Layer

After the transport lower layer receives a token, the transport lower layer determines if the frame is a transport-layer-to-transport layer message. If the 'layer flag' is set, then these types of messages are layer-to-layer messages and hence are not forwarded to upper layers. If the flag is not set, transport lower layer looks at the priority of the message and places the token into appropriate priority queue.

In one or more embodiments, the transport upper layer receives the token from the priority queue and determines if the 'extended flag' is set or not. If the flag is set, it indicates that a large volume of data is to be expected and informs the API that an extra byte has been used in header for sequencing large number of fragments.

The layer also reads the "Last Fragment" flag. A set 'last fragment' flag indicates to the layer that the current datagram fragment is the last fragment in the sequence of fragments and hence the end of one message. If there is any fragmentation, at least one fragment will have this flag set.

The layer further reads the acknowledgement flag. If the transmitter requests or otherwise is to be sent an acknowledgement for delivery of the datagram to the receiver's transport layer, the layer will set this flag and the receiver will acknowledge the receipt of the packet. If the devices engaged in communication have agreed on a window size for acknowledgements, then the transport layer acknowledges after receiving window size messages else the layer acknowledges each datagram.

The transport upper layer adds more information to the data token and forwards it to session layer. The transport upper layer informs the session layer if the message is a complete message or not. In case of fragmented message, the transport layer informs the session layer about receiving the last fragment, so that session layer may send an acknowledgement if needed.

Session Layer

From the data pointer in the token, the session layer accesses the frame and extracts session layer header. From the header, session layer first determines if the message is a layer-to-layer message or needs to be forwarded up the stack. If the message is a layer-to-layer type message, then the message is consumed by session layer.

If the layer flag is not set, the frame is forwarded up the stack. The session layer reads the 'Connection Type' field and determines if the message is of unknown connection type or connection-oriented or connectionless. An unknown connection type is generally for the messages exchanged during handshake process, whereas a connectionless message does not need an acknowledgement for delivery, and connection-oriented messages are the ones that use an acknowledgement on successfully delivery.

The session layer further looks into the message type field to determine the type of frame. The frame type is used to determine the purpose of the frame, and only 'Data' type frames are forwarded up the stack and the control type frames are consumed at session layer.

The CID is generated by the application providing a service. Any application that wants to use the service will request a communication ID. CID is unique within one module, for example all of the CID's generated by the UIC are unique within a particular UIC. The CID is generated through a handshake process, where the application using the service sends the details required for uniquely identifying an active connection and receives the CID in response.

The CID specifics and details may be stored in a CID table located in a shared memory region in one or more embodiments, so that the session layers of all the applications may access the CID. In a connectionless data frame, there is no CID information as there is no handshake utilized to establish a connection. Hence connectionless frames contain both source and destination port address in the header.

In a connection-oriented data transfer, there exists a CID in the session layer header. Once the session layer determines the CID from the header, the layer combines the information with the source logical address available in the data token to uniquely identify an entry in CID table. From this table, the session layer determines the source and destination port address and the file descriptors handling the port. The source logical address of the received frame is set by the data link layer along with the file handler information and is forwarded in the data token to the manager layer.

If the received frame is connection-oriented and is a complete message, the session layer maintains a record of the message and forwards the data token to the manager layer. Once the manager layer copies the frame from memory pool into the application buffer, the manager layer notifies the session layer about the successful delivery of data. On receipt of notification, the session layer sends an acknowledgement to the transmitter session layer regarding the successful delivery of data. If the delivery was unsuccessful, as a part of the acknowledgement, the session layer forwards the error message returned from the manager layer to the transmitter.

Manager Layer

The session layer calls an API in manager layer and passes the data token to the manager layer. The manager layer copies the data from memory pool into the application buffer and notifies the session layer regarding the copy. The manager layer notifies the lower layer about the delivery of message by modifying the data token and sending the data token back to the session layer. Once the data is successfully copied, the manager layer removes the frame pointer from the list of frames monitored by the timer and deletes the frame from the memory pool to make room for new packets.

It may happen that the application buffer is smaller in size than the received data frame, in such cases the manager layer will fill the application buffer with what it can hold and wait for the application to consume it. Once the application consumes the message, the remaining portion of the message is copied and the process is repeated until the complete frame is consumed. Before starting the progress of copying messages in small sizes, the manager layer removes the pointer to the frame from the timer-monitored list because the timer may expire and corrupt the message. Also, the manager layer notifies the lower layer regarding successful delivery of data only when a complete message is sent to the application. At the end of the sequential copy process, the manager layer deletes the frame from the memory pool.

In the case of fragmented data, as the fragments are received by this layer, it copies the fragments into the application buffer and notifies the session layer. The session layer forwards the notification to the transport layer. The transport layer, after receiving notifications for a window size number of messages, sends an acknowledgement to the transmitter about receiving the messages. When the last fragment is successfully delivered to the application, it implies that one complete message was delivered. In such cases, the manager layer notifies the session layer of success, and the session layer sends an acknowledgement message to the transmitter regarding the success, thus providing guaranteed delivery of data.

Data Flow Down the Stack

Assuming that in case of a connection-oriented data transfer, the handshake process has already been done and a valid CID has been already generated, the application copies data into an application buffer and passes a pointer to the API exposed by the manager layer for sending data over virtual ports. The application also specifies the file descriptor that handles the communication and the size of data to be written on the virtual port.

The priority of a message is determined by the priority of the virtual port being used or priority can be set for the message passing through. Hence, through a set of API's, the manager layer informs the session layer about the priority of data, size of data, file descriptor for the communication, pointer to application buffer, and if data is connection-oriented or connectionless. If the data is connectionless, the session layer looks into the file descriptor table and determines the port number associated with the file descriptor. The session layer then adds source and destination port addresses as header to the data. If the transfer is to be connection-oriented, the session layer performs a lookup in the CID table and determines CID associated with the file descriptor and adds this CID as header to the data. The session layer then forwards this pointer to the transport layer and waits for an acknowledgement from the receiver.

The transport upper layer determines the size of the data and determines if fragmentation is required or not. If fragmentation is needed, the transport upper layer breaks the data into manageable sizes and adds information to the header so that the data can be reassembled at the receiver's transport upper layer. If fragmentation is not needed, the transport upper layer still adds some information in one or more embodiments. For example, the transport upper layer copies the data from application buffer into transmitter memory pool and depending on the priority of data, stores the pointer into appropriate message queues.

The transport lower layer eventually reads the pointer from the priority queue and forwards it to the link layer. The link layer determines the destination logical address and adds it to the data header, computes a CRC on the frame and adds it to the frame before sending it. The MAC layer determines the bus over which the destination is available and sends the data over that bus.

Flow of Data Up the Stack

As the data frame arrives at the underlying bus, the MAC layer determines if the frame is for the subsystem or for some other subsystem. If it is for some other subsystem, the MAC layer drops the data frame. The MAC layer copies valid data frames into a shared memory region and calls an API in the Link layer to inform it about arrival of new data. Throughout the stack, only the pointer to this data is updated to reduce multiple copying of fragments.

The link layer computes the CRC on the received frame and compares the computed CRC with the CRC on the received frame. Frames with invalid CRC's are dropped. Pointers to valid frames are forwarded to the transport lower layer.

The transport lower layer reads the priority of the frame and adds a pointer to the frame to the respective priority queue. The pointer to the frame remains in the queue and waits for appropriate application to consume it. Eventually, the target application's transport upper layer reads the pointer to the frame from the priority queue.

The transport upper layer looks at the headers to determine if the data is fragmented or a complete message. If the data is fragmented, the layer reassembles all the messages from the sequence and then forwards it to the application layer. If the data is not fragmented, it directly forwards the pointer to the frame to the session layer through appropriate API calls.

The session layer looks at the frame headers and determines if the message is of type connectionless or connection-oriented. If the message is connectionless, the session layer looks at the destination port number and determines the file descriptor handling that port. The session layer forwards the pointer to the manager layer with appropriate file descriptor information. If the frame is connection-oriented, the session layer reads the CID and determines the file handler handling that communication. The session layer then forwards the file descriptor information to the manager layer and waits for an acknowledgement from the manager layer. The manager layer sends an acknowledgement indicating whether the data was delivered to the application or not. This information is used by the session layer to acknowledge receipt of data.

The manager layer may be implemented with a lightweight or thin layer and is responsible for copying the data from the memory pool into the application buffer and freeing the memory pool. Once the data gets copied into the application memory, the manager layer informs the application about data being available. The manager layer sends an acknowledgement to the session layer. Thus, to the applications, the manager layer offers synchronous and asynchronous methods for reading and writing to virtual ports.

FIG. 9 illustrates an activity diagram showing routing between various devices. As shown, Device A is connected directly to Device B, which is directly connected to Device C. Device A is not directly connect to Device C. When Device A attempts to send a message to Device C, it sends the message out and Device B reads the message, determines that the message is not for the device and checks to see if there is a path to the device in Device B's destination table. If so, Device B forwards the message to Device C, which processes the data. Hence, embodiments of the invention enable routing and daisy chain or multi-bus configurations that are generally not as flexibly possible in medical devices such as infusion pumps.

An embodiment of the manager layer API is detailed below. The manager layer provides the API to enable socket programming over the protocol stack. The manager layer API calls are utilized by any application that wishes to transfer data using an embodiment of the invention.

pro_socket—creates an unbound socket in a communication domain, and returns a file descriptor that can be used in later function calls that operate on sockets.
int16 pro_socket (ConnectionType type, uint8 *pSocket)
Arguments:
type: specifies the type of socket to be created (CONNECTIONTYPE and CONNECTIONLESSTYPE for connection oriented and connection-less data exchange).
pSocket: integer pointer to return newly created socket.

```
typedef enum ConnType
{
    CONNECTIONTYPE=1,
    CONNECTIONLESSTYPE=2,
    RAWTYPE=3
} ConnectionType;
```

On successful completion, the function shall return a SUCCESS; else appropriate error code is returned. The API returns allocated socket in the reference variable pSocket passed as a parameter.

pro_bind—assigns a local address to a socket identified by file descriptor socket.
int16 pro_bind (uint8 uint8Socket, const ProSockaddr * pAddress)

```
typedef struct pro_sockaddr
{
    uint8 address;
    uint8 portNo;
    uint8 priority;
    uint8 flags;
    uint32 timeout;
    datafilter *filter;
} ProSockaddr;
``` address: holds logical address of device
portNo: holds port number for connection
priority: holds the priority of the port. All the data passing through this port inherits ports priority
flags: holds configuration flags for changing behavior of socket
TIMEOUT: flag is set, waits for an operation to complete within a given period of time, else returns.
SO_LINGER: set flag indicates that a connection will be terminated only when all the data pending to be sent is sent successfully.
FILTER_DATA: set flag indicates that the data matching supplied filter pattern will only be forwarded to callback function registered to handle it. If flag is reset, data matching the filter will be sent to both, regular socket handler as well as to the registered callback function.
timeout: If the TIMEOUT flag is set, timeout value is specified here. A timeout value of 0 returns immediately.
filter: link list of datafilter type structure defining the filter to be applied on received data. More than one element in this link list will have an ORing property. As an example, if an application wants to process data either from PMC, or UIC, or CE or all three, it will create three nodes in this link list one for each PMC, UIC and CE.

Datafilter structure is used to allow applications to select what messages they want to receive, and which function should handle what type of messages. A regular expression pattern is used to create a filter on received data and once a match is found, data is forwarded to registered callback function.

```
typedef struct
{
    char *regEx;
    uint8 index;
    uint8 length;
    void *callback;
    datafilter *filter;
} datafilter;
``` regEx: pointer to regular expression to be used for matching.
index: location to start looking for match in the data section of received message. A '0' in this field indicates that the match will start from the beginning.
length: staring from the provided index, indicates the length of data section to be considered for regular expression matching. If index contains '0' and length contains '0', match will be performed over the entire data section.
callback: function to be called in case of a successful match. If this field is set to null, all the matching data packets will be dropped depending on FILTER_DATA flag.
filter: linklist of any additional filter to be added over existing filter. If this filed is contains additional filters, on a successful match, callback is made to the function specified in the structure containing this linklist. This link list of filters has anding properties, i.e. a match is successful only if all the regEx specified in all the filters match. As an example, if an application wants to process data containing expressions PMC, UIC and CE, it will instantiate this filter for PMC and have a link list containing filters for UIC and CE respectively.

One or more embodiments support three priority levels for messages namely high, medium and low. The enum defining message priority is as follows.

```
Typedef enum ProPriority
{
    HIGHPRIORITYTYPE = 1,
    MEDIUMPRIORITYTYPE = 2,
    LOWPRIORITYTYPE = 3
} MessagePriority;
```

Arguments:
uint8Socket: file descriptor of socket to be bound
pAddress: pointer to ProSockaddr struct containing address to be bound to the socket.

Return Value:

Upon successful completion, the function shall return SUCCESS, otherwise appropriate error code.

pro_connect—attempts to connect a socket to the specified address.

int16 pro_connect (uint8 uint8Socket, const ProSockaddr *pAddress)

Arguments:

uint8Socket: socket to be connected to specified address.

pAddress: pointer to structure pro_sockaddr containing peer address.

Return Value:

Upon successful completion, the function shall return SUCCESS; otherwise returns appropriate error code pro_listen—marks the socket referred to by "socket" as a passive socket, that is, as a socket that will be used to accept incoming connection requests using accept( )

int16 pro_listen (uint8 uint8Socket, uint8 uint8Backlog)

Arguments:

uint8Socket: file descriptor of a socket that needs to be put in accepting connections mode.

uint8Backlog: set a limit on number of outstanding connections in the socket's listen queue. A zero would set the queue length to system defined minimum queue length.

Return Value:

Upon successful completion, the function shall return SUCCESS; otherwise, appropriate error code is returned.

pro_accept—extracts the first connection on the queue of pending connections, creates a new connected socket with same socket type protocol and address family as the specified socket, and returns a new file descriptor for the socket.

int16 pro_accept (uint8 uint8Socket, ProSockaddr *pAddress, uint8 *pClientSocket)

Arguments:

uint8Socket: file descriptor associated with socket.

pAddress: Either a NULL pointer, or a pointer to ProSockaddr struct where the address of connecting socket shall be returned.

pClientSocket: pointer to an unsigned integer for returning file descriptor associated with the newly created socket.

Return Value:

Upon successful completion SUCCESS is returned along with an associated file descriptor for the newly created socket, on failure, returns appropriate error code.

pro_send—initiates transmission of a message from the specified socket to its peer. The pro_send( ) function sends a message when the socket is connected.

int16 pro_send (uint8 uint8Socket, const void *pBuffer, uint32 intLength, uint32 *pBytesSent)

Arguments:

uint8Socket: socket's file descriptor pBuffer: points to buffer containing the message to send.

intLength: length of message in bytes.

pBytesSent: pointer to an integer for returning actual number of bytes sent.

Return Value:

Upon successful completion, the API returns SUCCESS else appropriate error code is returned.

pro_recv—receives a message from a connection-mode or connectionless-mode socket. It is normally used with connected sockets because and does not provide the source address of received data to the application.

int16 pro_recv (uint8 uint8Socket, void *pBuffer, uint32 uintLength, uint32 *pBytesReceived)

Arguments:

uint8Socket: file descriptor of socket.

pBuffer: pointer to the buffer where message should be stored.

uintLength: length in bytes of the message to be received.

pBytesReceived: pointer to an integer for returning number of bytes actually received.

Return Value:

Upon successful completion, SUCCESS is returned along with number of bytes in the reference passed as a parameter, else returns appropriate error code.

pro_close—deallocates the file descriptor and makes the file descriptor available for functions which allocate file descriptors. All outstanding record locks owned by the process on the file associated with the file descriptor are removed. Causes the socket to be destroyed. If the socket is in connection-oriented, and the SO_LINGER option is set for the socket with non-zero linger time, and the socket has un-transmitted data, then pro_close( ) blocks for up to the current linger interval for all pending data to be transmitted.

int16 pro_close (uint8 uint8Socket)

Arguments:

uint8Socket: file descriptor of socket that needs to be closed.

Return Value:

Upon successful completion, function shall return SUCCESS; otherwise appropriate error code shall be returned.

One skilled in the art will recognize that in addition to the exemplary API illustrated above for the Manager Layer, API's for the Session, Transport and Data Link Layers may be implemented as desired to communicate the messages shown in FIGS. 10A-D, 11A-B and 12A-B depending on the desired application.

Figure 13A:
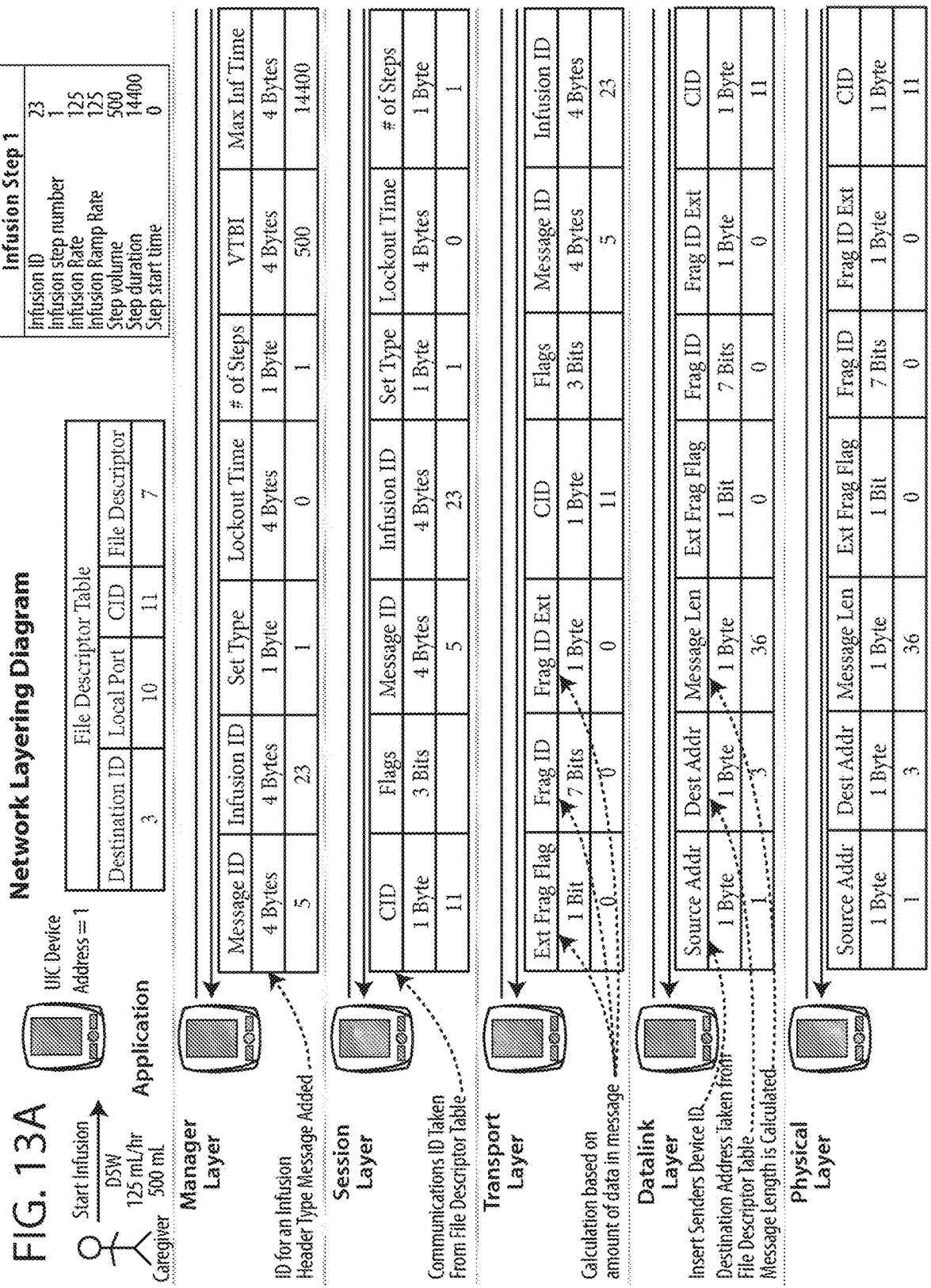
FIGS. 13A-B illustrate an exemplary message transfer of a medical function using exemplary values within the messages to demonstrate the system and method according to at least one embodiment of the invention.
Figure 13B:
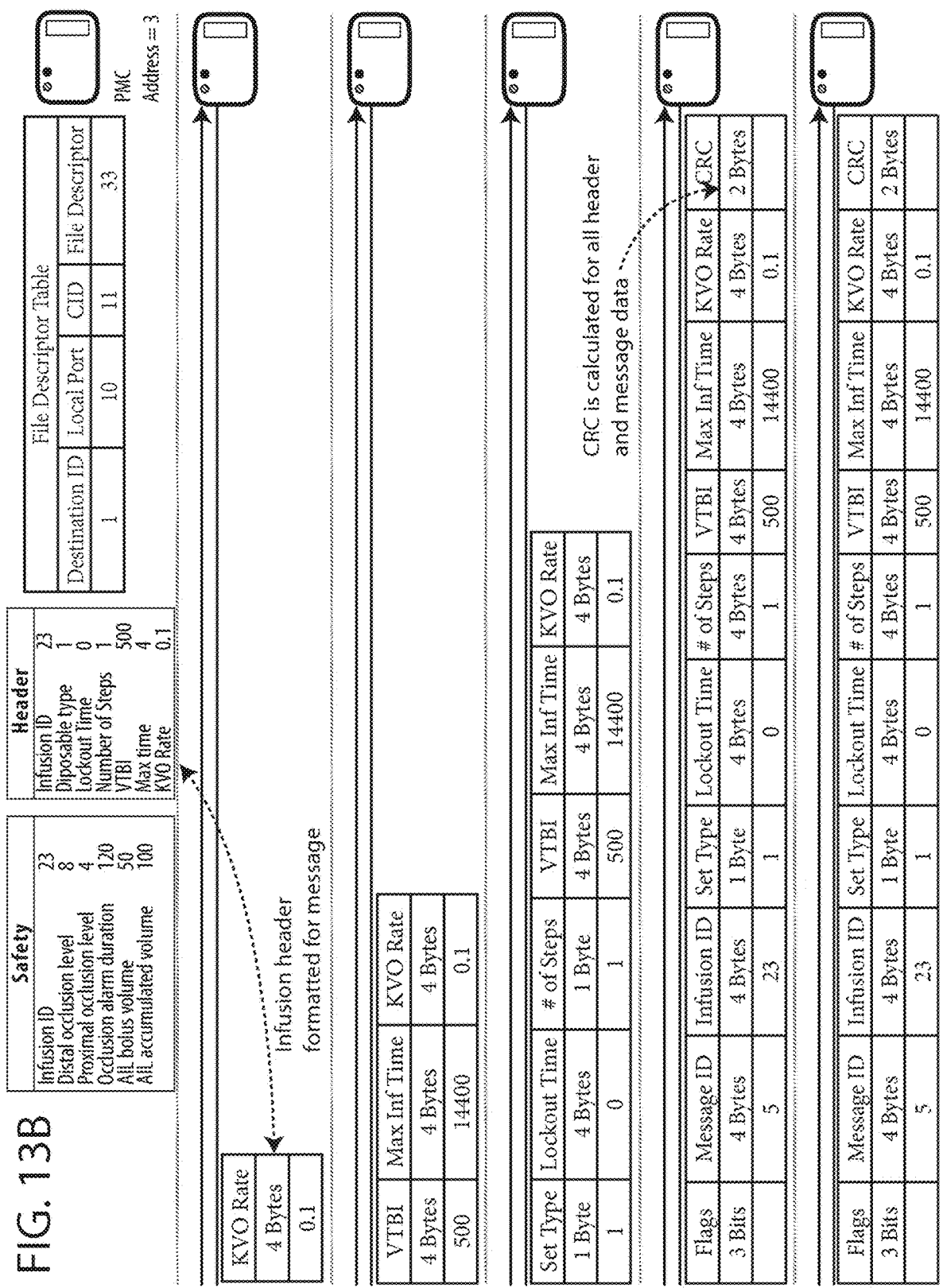

One or more embodiments of the invention may be implemented as a system or method. For example at least one embodiment may include a medical device communication method that includes accepting a request by a programmable device to obtain a device identifier associated with a transmitting device associated with the request, a connection type of connection-oriented or connectionless-oriented, and a receiving device number associated with a receiving device to transmit a message to. The method may also include determining a port number of a port to transmit said message to, for example either via a requesting programmable device or the programmable device that receives the request. Embodiments may also include generating a communication identifier or CID for at least the advantages stated throughout this disclosure. Embodiments may also include accepting a request associated with a medical function, inserting the CID and the medical function into the message, determining if the connection type is connection-oriented or connectionless and transmitting the message to a medical device. This scenario is shown with exemplary values to demonstrate the previous message formatting and transfer in FIGS. 13A and 13B, which are intended to couple with one another on the right side of FIG. 13A and the left side of FIG. 13B.

Embodiments may also include transmitting the message to the receiving device even if the receiving device is not directly connected to the transmitting device. This enables built in routing that allows for devices to pass through messages without requiring a master to control all phases of communication for example.

Embodiments may also include accepting a multicast request configured to enable multiple receiving devices to receive the message. Embodiments may further include accepting a priority parameter configured to enable prioritized handling of the message. This enables messages with high priority to be delivered before other lower priority messages and in one or more embodiments may be implemented with a plurality of message data structures such as queues, linked lists or any other data structure or structures. Embodiments may include transmitting messages from a high priority message queue before transmitting data from a low priority message queue. Other embodiments may apply any type of strategy pattern to the delivery process, and may for example change strategies depending on the type of messages that are likely to be received in particular time periods. This enables predictive handling and processing of messages to provide intelligent and robust delivery of medical functions.

Embodiments may also include determining if a size of data to transfer is larger than a predetermined fragmentation value and packing the data in a plurality of messages to facilitate transfer. Embodiments may efficiently utilize memory and for example reduce latency by copying a pointer to the message between a plurality of message layers without copying the message itself. This is the case since the message does not have to be reconstructed in full within the stack until the full message is received in the application. Furthermore, embodiments of the invention may utilize optimized memory management that includes requesting memory from a buffer that includes non-uniform sizes to further increase efficiency of data memory utilization and lower overall required memory. When sending data packets or message that are larger than the maximum size allowed by the underlying hardware, embodiments may include setting a last fragmentation flag in a final message of fragmented message, starting a timer for an acknowledgement and retransmitting the final message if said timer expires. Further increases in efficiency may be achieved by embodiments that include receiving a request to change a window size for receipt of fragmented messages and adjusting memory usage based thereon, for example having lower window sizes for more reliable communication links. Embodiments may also include providing the device identifier to a new medical device that replaces the medical device after hot-swapping the new medical device for the original medical device, i.e., if a failure occurs. This allows embodiments of the invention to provide robust functionality and transparent replacement of hardware without interrupting medical functions or at least minimizing the interruptions. Embodiments may also include providing a pointer to a complete message after receipt of multiple fragmented messages without copying received message data after receipt thereof. This enables incoming data to be inserted into a buffer once and given to the application after the data is received without extraneous copying for example, which reduces memory utilization and programmable device processing required. One or more embodiments of the invention may include accepting an infusion request associated with an infusion related medical function. Any other type of medical function is in keeping with the spirit of the invention.

Embodiments of the system may include a programmable device configured to accept a request to obtain a device identifier associated with a transmitting device associated with the request, a connection type of connection-oriented or connectionless-oriented, a receiving device number associated with a receiving device to transmit a message to. Embodiments of the system may further determine a port number of a port to transmit said message to, generate a communication identifier or CID and accept a request associated with a medical function. The system may also insert the CID and the medical function into the message, determine if the connection type is connection-oriented or connectionless and transmit the message to a medical device. Embodiments of the system may also implement all functionality of the method previously described and may utilize any of the data structures or API's described herein in combination.

While the invention herein disclosed has been described by means of specific embodiments and applications thereof, numerous modifications and variations could be made thereto by those skilled in the art without departing from the scope of the invention set forth in the claims.

What is claimed is:

1. A medical device communication system for connecting a first medical device system with a second medical device system, the medical device communication system comprising a controller configured to:
   receive a first message comprising a request for an address from a first medical device system;
   determine in a stored table that there is no entry corresponding to the first medical device system;
   generate a connection identifier for the first medical device system based on the determination; and
   transmit the connection identifier to the first medical device system, wherein the first medical device system is further configured to update its identity with the connection identifier.

2. The communication system of claim 1, wherein the controller is further configured to facilitate transmission of a second message from the first medical device system to an additional hardware, wherein the first medical device system and the additional hardware are not directly connected.

3. The communication system of claim 2, wherein the second message is transferred between a plurality of message layers by copying a pointer and without copying said second message itself.

4. The communication system of claim 2, wherein a session layer communication is made independent of bus topology.

5. The communication system of claim 1, wherein the controller is further configured to transmit the connection identifier to a second medical device system that replaces the first medical device system.

6. The communication system of claim 1, wherein a fragmented message is reassembled into a complete message in an application buffer.

7. The communication system of claim 1, wherein the controller is further configured to:
   determine that a size of data to transfer is larger than a predetermined fragmentation value; and
   pack said data in a plurality of messages independent of an underlying data bus width.

8. The communication system of claim 1, wherein the controller is further configured to request memory from a buffer comprising non-uniform sizes.

9. The communication system of claim 1, wherein the first medical device system is connected with the controller without altering an application of the first medical device system.

10. The communication system of claim 1, wherein the controller manages connection requests from a plurality of medical device systems.

11. A method for connecting hardware components of an medical device system, the method comprising:
- transmitting a first connection identifier to a controller of a first medical device system responsive to a first message corresponding to a first request for an address from the first medical device system;
- receiving a second message corresponding to a second request for an address from a second medical device system;
- determining that the second medical device system has replaced the first medical device system;
- changing an association of the first connection identifier from the first medical device system to the second medical device system;
- transmitting the first connection identifier to the second medical device system, wherein the second medical device system is further configured to update its identity with the first connection identifier.

12. The method of claim 11, further comprising facilitating transmission of a second message from the first medical device system to an additional hardware, wherein the first medical device system and the additional hardware are not directly connected.

13. The method of claim 11, further comprising transmitting messages between hardware components by copying a pointer and without copying the messages.

14. The method of claim 11, wherein a session layer communication is made independent of bus topology.

15. The method of claim 11, wherein a fragmented message is reassembled into a complete message in an application buffer.

16. The method of claim 11, further comprising determining that a size of data to transfer is larger than a predetermined fragmentation value and packing said data in a plurality of messages independent of an underlying data bus width.

17. The method of claim 11, further comprising requesting memory from a buffer comprising non-uniform sizes.

* * * * *